(12) United States Patent
Maeda et al.

(10) Patent No.: US 9,701,977 B2
(45) Date of Patent: Jul. 11, 2017

(54) PREPHENATE DEHYDROGENASES AND AROGENATE DEHYDROGENASES THAT ARE INSENSITIVE TO EFFECTOR FEEDBACK INHIBITION AND METHODS OF USING THE SAME

(71) Applicant: Wisconsin Alumni Research Foundation, Madison, WI (US)

(72) Inventors: Hiroshi A. Maeda, Madison, WI (US); Craig Albert Schenck, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/548,216

(22) Filed: Nov. 19, 2014

(65) Prior Publication Data

US 2015/0150157 A1    May 28, 2015

Related U.S. Application Data

(60) Provisional application No. 62/058,457, filed on Oct. 1, 2014, provisional application No. 61/906,252, filed on Nov. 19, 2013.

(51) Int. Cl.
*C12N 15/82* (2006.01)
*C12N 9/04* (2006.01)
*C12N 9/02* (2006.01)

(52) U.S. Cl.
CPC ......... *C12N 15/8251* (2013.01); *C12N 9/001* (2013.01); *C12N 15/8274* (2013.01); *C12Y 103/01013* (2013.01); *C12Y 103/01078* (2013.01); *C07K 2319/60* (2013.01)

(58) Field of Classification Search
None
See application file for complete search history.

(56) References Cited

U.S. PATENT DOCUMENTS

| | | | | |
|---|---|---|---|---|
| 7,569,389 | B2 * | 8/2009 | Feldmann | C07K 14/415 435/419 |
| 2013/0333061 | A1 * | 12/2013 | Wu | C07K 14/415 800/260 |

OTHER PUBLICATIONS

Rubin, J. L. et al., "Enzymology of L-Tyrosine Biosynthesis in Mung Bean (*Vigna radiata* [L.] Wilczek)," 1979 Plant Physiol. 64:727-734.
Schenck, C. A. et al., "Non-plastidic, Tyrosine-Insensitive Prephenate Dehydrogenases from Legumes," 2015 Nature Chemical Biology 11:52-57 Published online Nov. 17, 2014, doi:10.1038/nchembio.1693.
Siehl, D.L., "The Biosynthesis of Tryptophan, Tyrosine, and Phenylalanine from Chorismate," 1999 Plant Amino Acids: Biochemistry and Biotechnology, Edited by Bijay K. Singh, pp. 171-204.

* cited by examiner

*Primary Examiner* — Brent Page
(74) *Attorney, Agent, or Firm* — Andrus Intellectual Property Law, LLP

(57) ABSTRACT

Prephenate dehydrogenases and arogenate dehydrogenase polynucleotide and polypeptide sequences are provided herein. These polypeptides are all insensitive to effector based feedback inhibition. Polypeptides with these activities and lacking feedback inhibition by the product were not previously identified and characterized from plants. The polypeptides may be used to generate constructs and transgenic cells or plants. Methods of increasing production of products of the tyrosine or HPP pathway by increasing expression of the polynucleotides provided herein in plants or cells overexpressing the polypeptides are provided. In addition overexpression of the polypeptides in plant cells increases resistance to herbicides.

24 Claims, 15 Drawing Sheets

Fig. 2
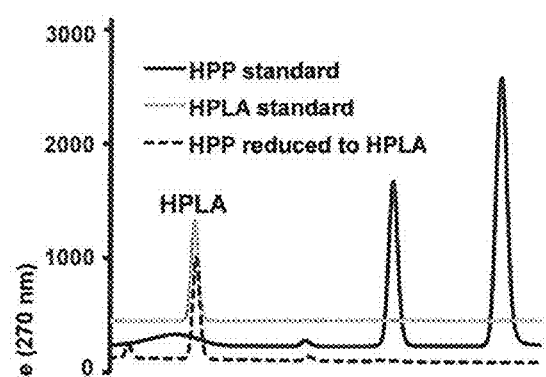
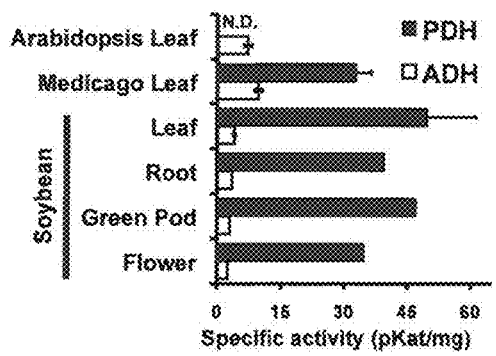
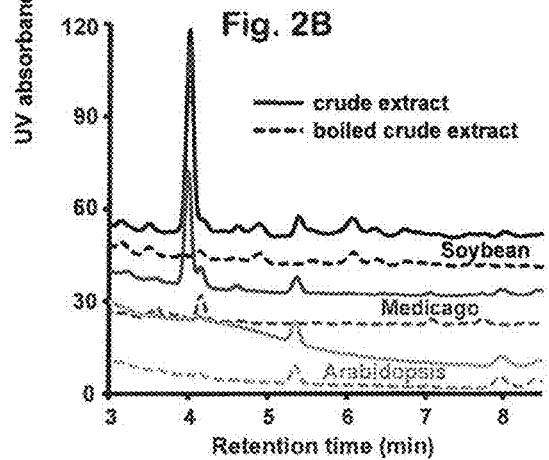

Fig. 3
Fig. 3A
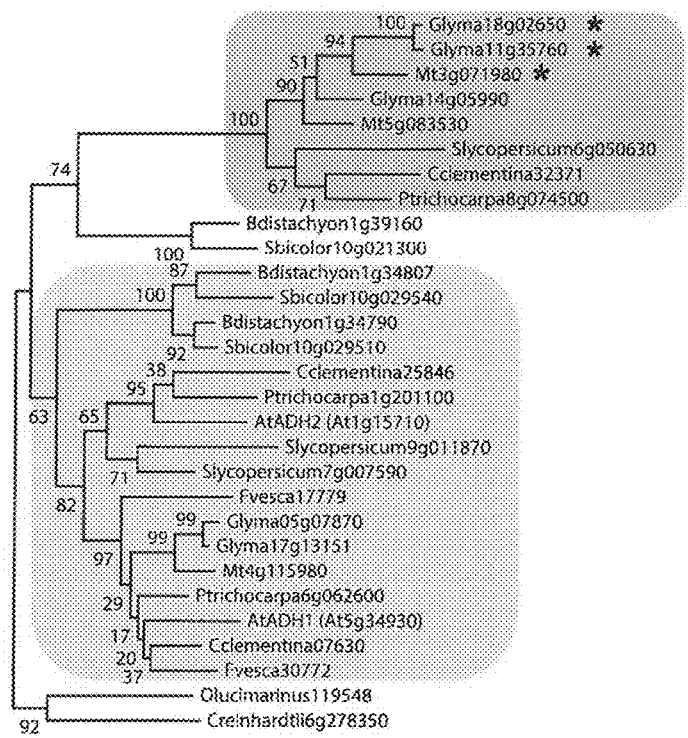
Fig. 3B
Fig. 3C
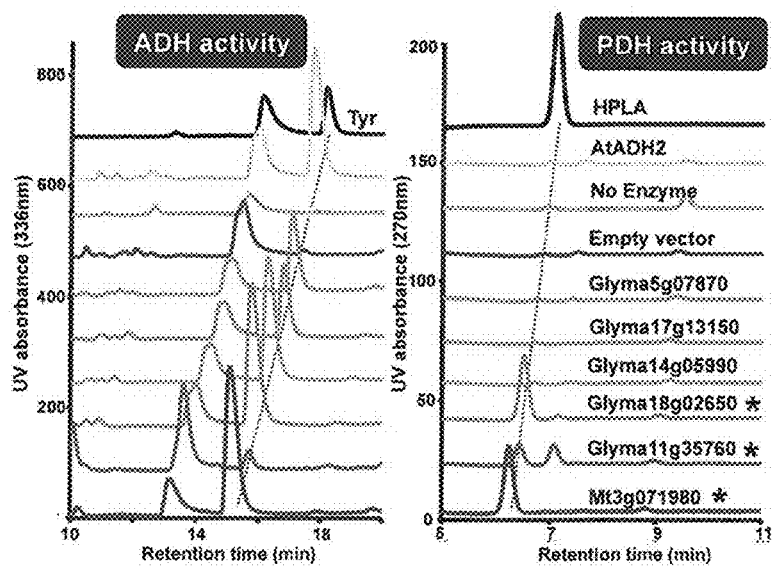

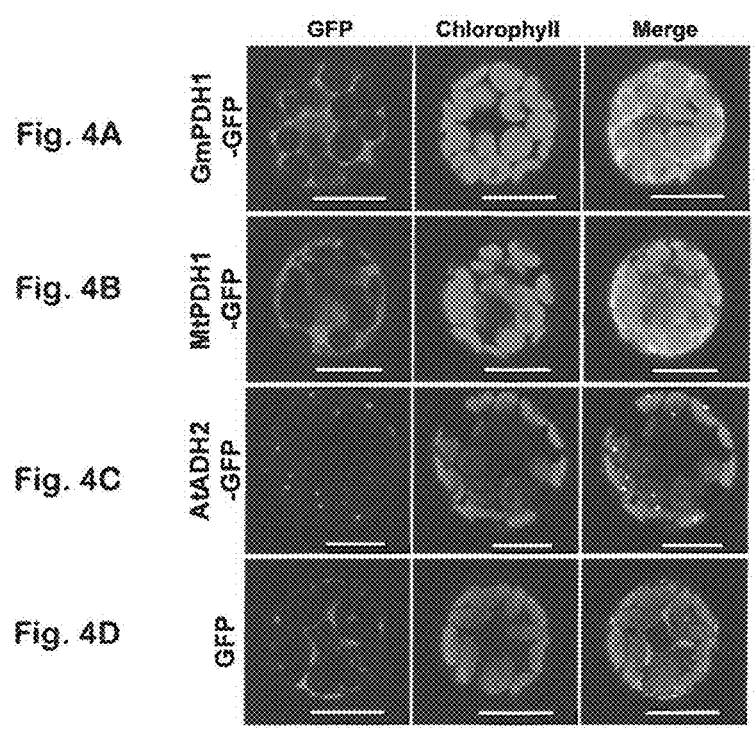

Fig. 4
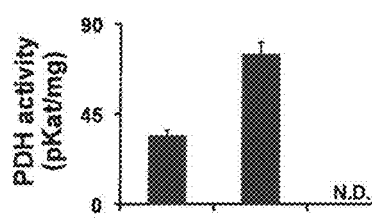
Fig. 4E
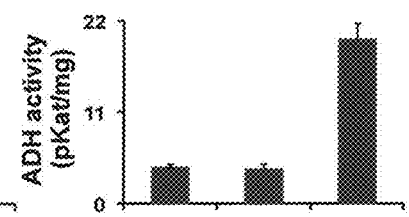
Fig. 4F
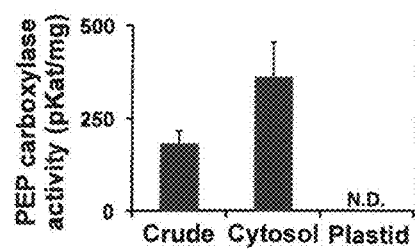
Fig. 4G
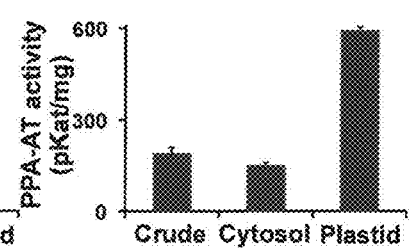
Fig. 4H
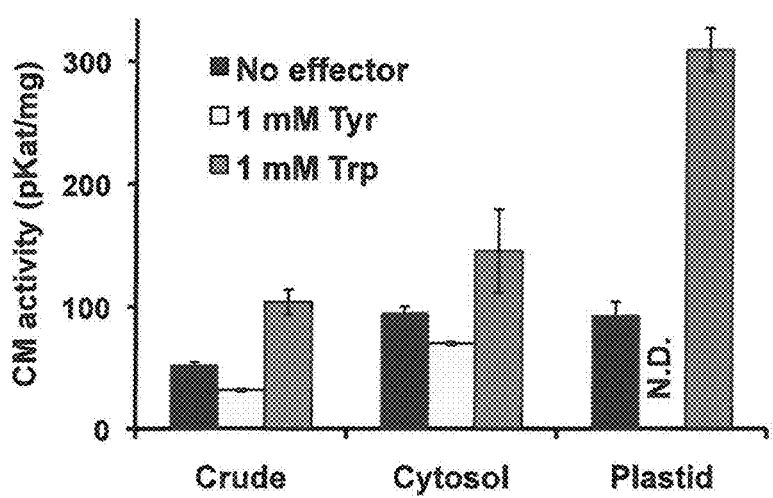
Fig. 4I Fig. 5
Fig. 5A
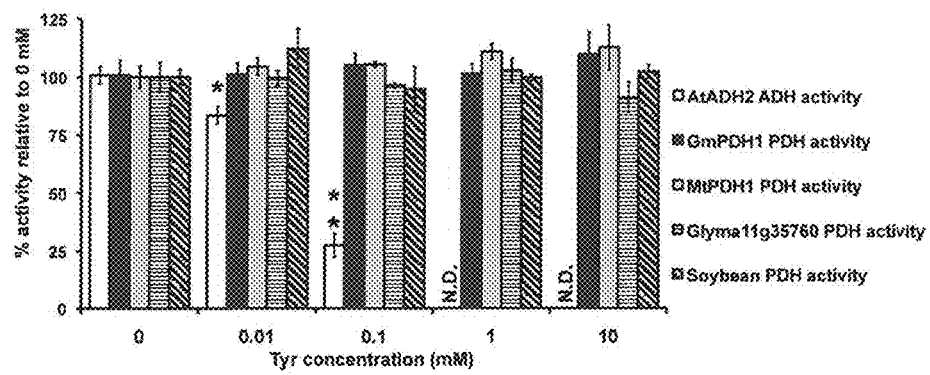
Fig. 5B
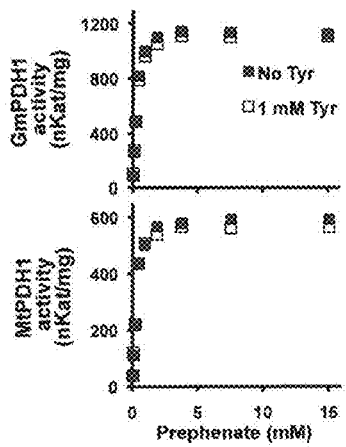
Fig. 5C
Fig. 5D
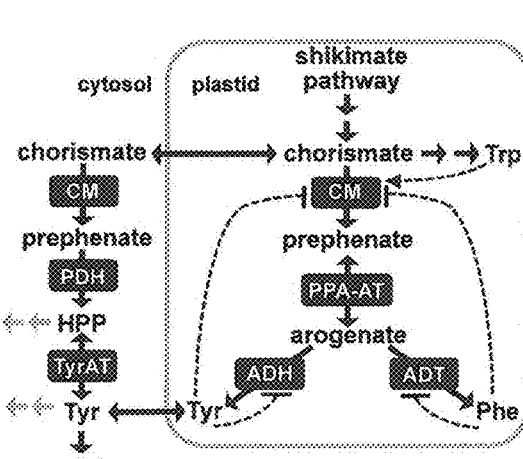

Fig. 7
Fig. 7A
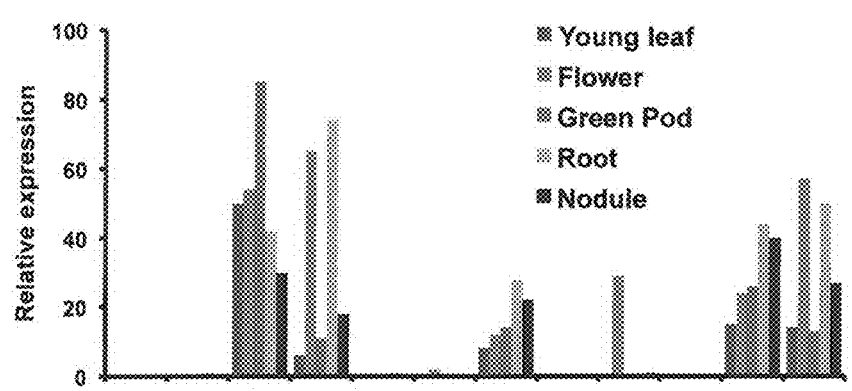
Fig. 7B
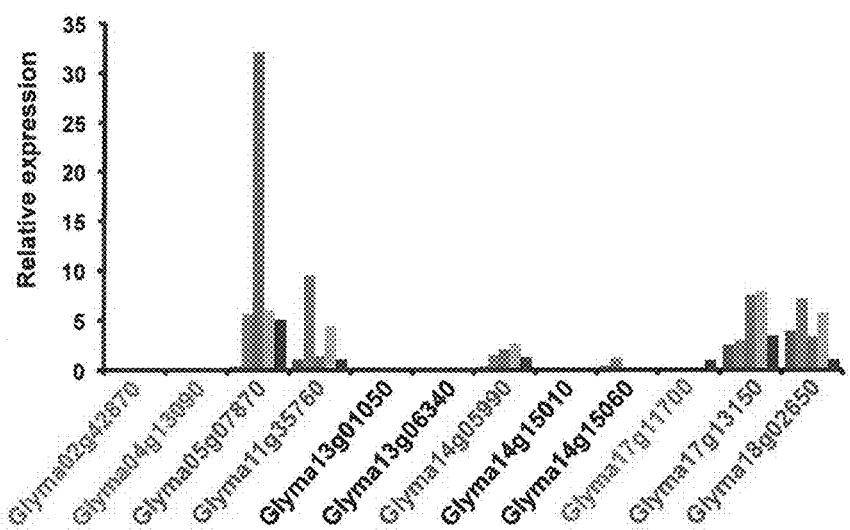

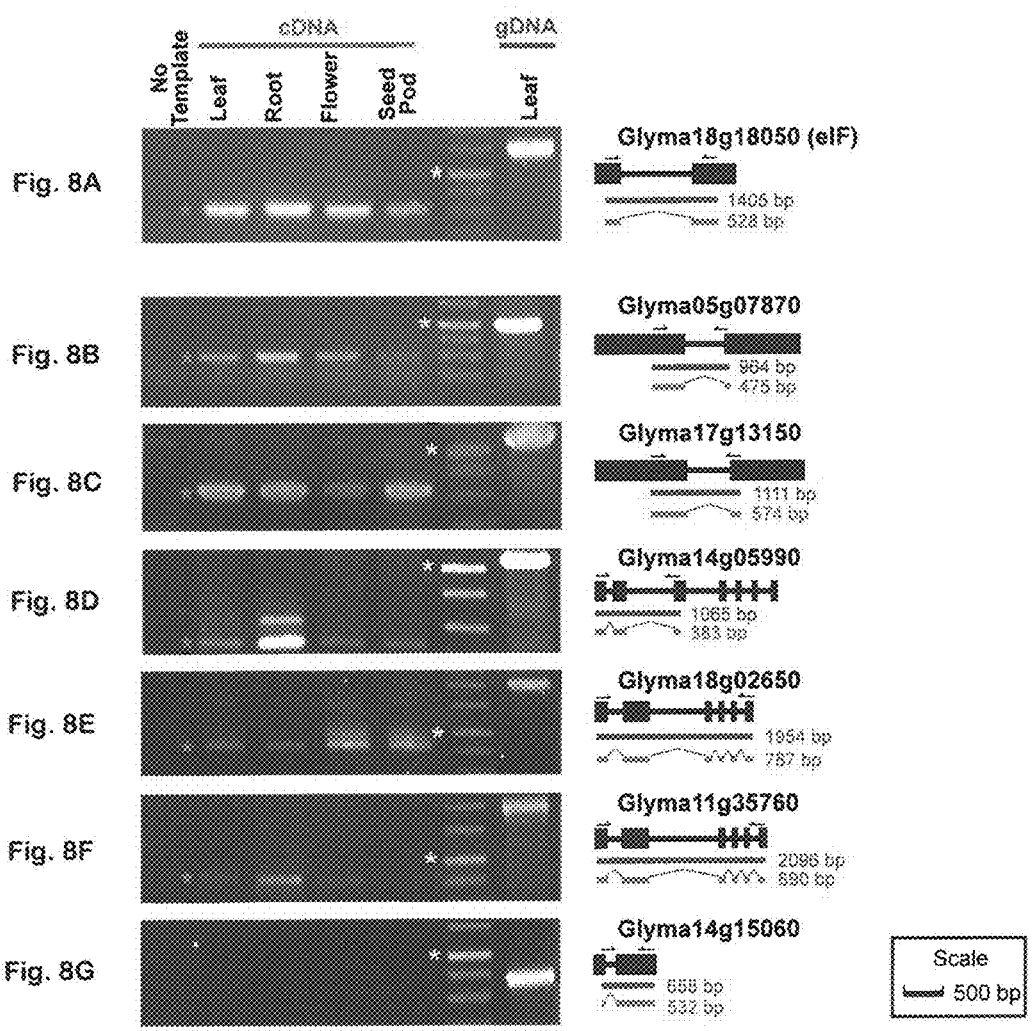

Fig. 11
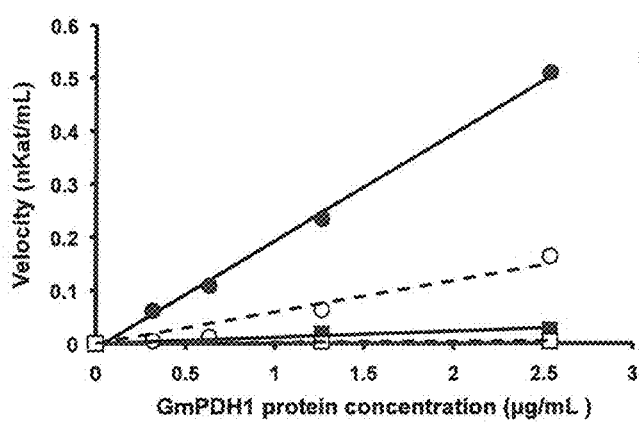
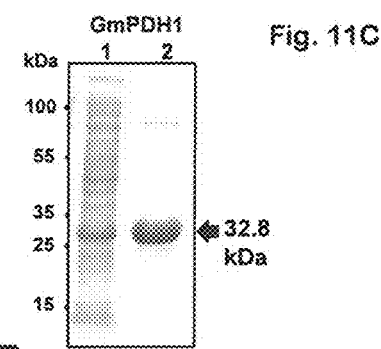
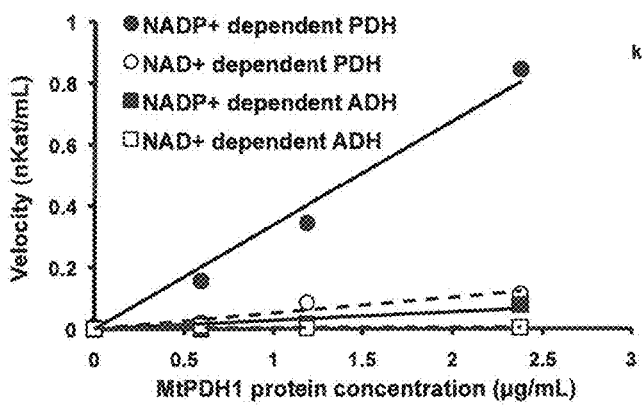
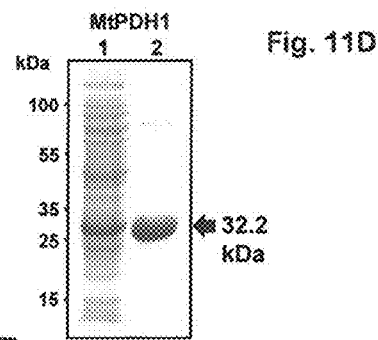

Fig. 12
Fig. 12A
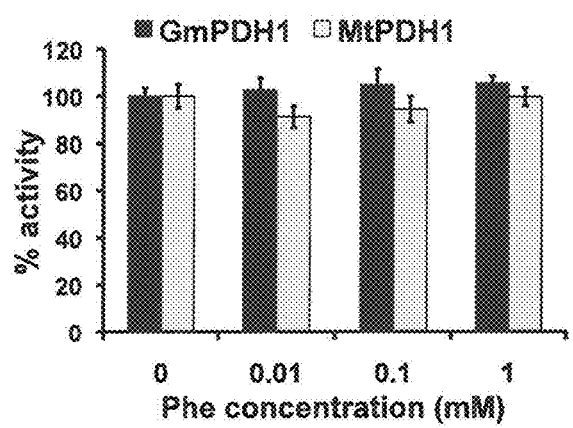
Fig. 12B
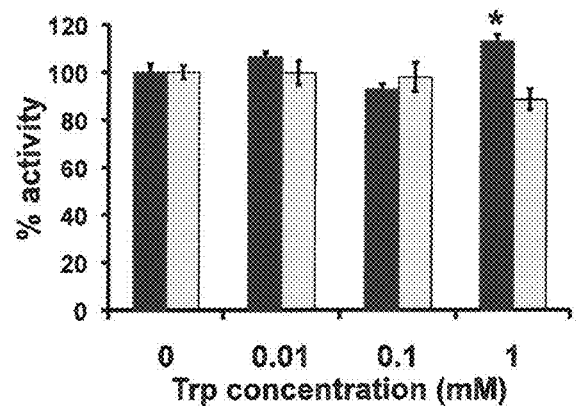
Fig. 12C
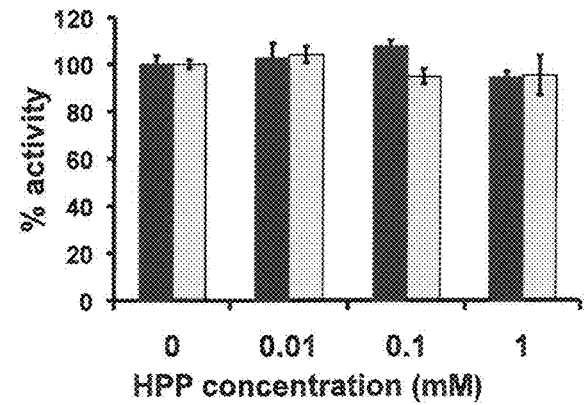

SEQUENCE LISTING

```
<160> NUMBER OF SEQ ID NOS: 62

<210> SEQ ID NO 1
<211> LENGTH: 816
<212> TYPE: DNA
<213> ORGANISM: Glycine max

<400> SEQUENCE: 1
atgtcaacct catcctcttc ccaaagcctc aaaattggca tagttggatt cggcaacttt      60
ggccagtttc tggccaagac aatgataaaa caaggccaca ctctcacagc aacttctcga     120
tctgattact ctgaactttg tctccaaatg ggcatccatt ttttcaggga tgtcagcgca     180
ttccttaccg cagacataga tgtcatagtg ttgtgcacat cgatattatc gctatccgag     240
gttgtcgggt caatgccact cacctccctg aagcgaccaa cgctctttgt tgatgttctt     300
tctgtcaaag agcacccaag agagcttcta ctgcgagagt tgccagagga ttcggacata     360
ctctgcacgc acccaatgtt tggtcctcag actgccaaga atggatggac agatcacact     420
ttcatgtatg acaaagttcg gataagagac gaagttatct gctctaattt catccaaatt     480
tttgctactg agggttgcaa gatggtacag atgtcctgtg aggaacatga cagagcagct     540
gctaagagcc aatttatcac tcacacaatt ggcaggacac tgggagaaat ggatattcaa     600
tccacaccta ttgacactaa gggcttcgag acacttgtta aattgaagga gacgatgatg     660
agaaatagtt ttgatttgta tagtggatta ttcgtgtata acagattcgc cagacaagag     720
ctggaaaacc ttgaacatgc cttgcacaaa gtcaaagaaa cgctgatgat acaaaggacg     780
aatggggagc agggtcataa aagaactgaa agttga                               816
```

```
<210> SEQ ID NO 2
<211> LENGTH: 271
<212> TYPE: PRT
<213> ORGANISM: Glycine max

<400> SEQUENCE: 2

Met Ser Thr Ser Ser Ser Ser Gln Ser Leu Lys Ile Gly Ile Val Gly
1               5                   10                  15

Phe Gly Asn Phe Gly Gln Phe Leu Ala Lys Thr Met Ile Lys Gln Gly
            20                  25                  30

His Thr Leu Thr Ala Thr Ser Arg Ser Asp Tyr Ser Glu Leu Cys Leu
        35                  40                  45

Gln Met Gly Ile His Phe Phe Arg Asp Val Ser Ala Phe Leu Thr Ala
    50                  55                  60

Asp Ile Asp Val Ile Val Leu Cys Thr Ser Ile Leu Ser Leu Ser Glu
65                  70                  75                  80

Val Val Gly Ser Met Pro Leu Thr Ser Leu Lys Arg Pro Thr Leu Phe
                85                  90                  95

Val Asp Val Leu Ser Val Lys Glu His Pro Arg Glu Leu Leu Leu Arg
            100                 105                 110

Glu Leu Pro Glu Asp Ser Asp Ile Leu Cys Thr His Pro Met Phe Gly
        115                 120                 125

Pro Gln Thr Ala Lys Asn Gly Trp Thr Asp His Thr Phe Met Tyr Asp
    130                 135                 140

Lys Val Arg Ile Arg Asp Glu Val Ile Cys Ser Asn Phe Ile Gln Ile
145                 150                 155                 160

Phe Ala Thr Glu Gly Cys Lys Met Val Gln Met Ser Cys Glu Glu His
                165                 170                 175

Asp Arg Ala Ala Ala Lys Ser Gln Phe Ile Thr His Thr Ile Gly Arg
            180                 185                 190

Thr Leu Gly Glu Met Asp Ile Gln Ser Thr Pro Ile Asp Thr Lys Gly
        195                 200                 205

Phe Glu Thr Leu Val Lys Leu Lys Glu Thr Met Met Arg Asn Ser Phe
    210                 215                 220

Asp Leu Tyr Ser Gly Leu Phe Val Tyr Asn Arg Phe Ala Arg Gln Glu
225                 230                 235                 240

Leu Glu Asn Leu Glu His Ala Leu His Lys Val Lys Glu Thr Leu Met
                245                 250                 255

Ile Gln Arg Thr Asn Gly Glu Gln Gly His Lys Arg Thr Glu Ser
            260                 265                 270

<210> SEQ ID NO 3
<211> LENGTH: 825
<212> TYPE: DNA
<213> ORGANISM: Glycine max

<400> SEQUENCE: 3
atgacaacca tgtcaacctc atcctcttcc caaagcctca aaattggcat tgttggattc      60
ggcaactttg gccagttttct ggccaagaca atgattaaac aaggccacac tctcacagca    120
acttctcgat ctgattactc tcaactttgt ctccaaatgg ggatccattt tttcagggat     180
gtcagcgcat tcctcgccgc agacatagat gttatagtgt tgtgcacatc gatattatcg    240
ctatccgagg ttgtagggtc aatgccactc acttccctga agcgaccaac gctctttgtt    300
gatgttcttt ctgtgaaaga gcacccaaga gagcttctac tacgagagtt gccagaggat    360
tcagacatac tctgcacgca cccaatgttt ggtcctcaga ctgccaataa tggatggaca    420
```

```
gatcacactt tcatgtatga caaagttcgg ataagagacg aagctacttg ctctagtttc      480
atccaaatct ttgctactga gggttgcaag atggtacaga tgtcctgtga ggaacatgac      540
agagcggctg ctaagagcca atttatcaca cacacaattg gcaggacatt gggagaaatg      600
gatattcaat ccacacctat tgacactaag ggctttgaga cacttgttaa attgaaggag      660
actatgatga gaaatagttt tgatttgtac agtggattat tcgtgtataa cagattcgcc      720
agacaagagt tggaaaacct tgaacatgcc ttttacaaag tcaaagaaac gctgatgata      780
caaaggtcga atggggagca gggtcataaa agaaccgaaa gttga                      825
```

<210> SEQ ID NO 4
<211> LENGTH: 274
<212> TYPE: PRT
<213> ORGANISM: Glycine max

<400> SEQUENCE: 4

```
Met Thr Thr Met Ser Thr Ser Ser Ser Gln Ser Leu Lys Ile Gly
1               5                   10                  15

Ile Val Gly Phe Gly Asn Phe Gly Gln Phe Leu Ala Lys Thr Met Ile
                20                  25                  30

Lys Gln Gly His Thr Leu Thr Ala Thr Ser Arg Ser Asp Tyr Ser Gln
            35                  40                  45

Leu Cys Leu Gln Met Gly Ile His Phe Phe Arg Asp Val Ser Ala Phe
        50                  55                  60

Leu Ala Ala Asp Ile Asp Val Ile Val Leu Cys Thr Ser Ile Leu Ser
65                  70                  75                  80

Leu Ser Glu Val Val Gly Ser Met Pro Leu Thr Ser Leu Lys Arg Pro
                85                  90                  95

Thr Leu Phe Val Asp Val Leu Ser Val Lys Glu His Pro Arg Glu Leu
            100                 105                 110

Leu Leu Arg Glu Leu Pro Glu Asp Ser Asp Ile Leu Cys Thr His Pro
        115                 120                 125

Met Phe Gly Pro Gln Thr Ala Asn Asn Gly Trp Thr Asp His Thr Phe
    130                 135                 140

Met Tyr Asp Lys Val Arg Ile Arg Asp Glu Ala Thr Cys Ser Ser Phe
145                 150                 155                 160

Ile Gln Ile Phe Ala Thr Glu Gly Cys Lys Met Val Gln Met Ser Cys
                165                 170                 175

Glu Glu His Asp Arg Ala Ala Ala Lys Ser Gln Phe Ile Thr His Thr
            180                 185                 190

Ile Gly Arg Thr Leu Gly Glu Met Asp Ile Gln Ser Thr Pro Ile Asp
        195                 200                 205

Thr Lys Gly Phe Glu Thr Leu Val Lys Leu Lys Glu Thr Met Met Arg
    210                 215                 220

Asn Ser Phe Asp Leu Tyr Ser Gly Leu Phe Val Tyr Asn Arg Phe Ala
225                 230                 235                 240

Arg Gln Glu Leu Glu Asn Leu Glu His Ala Phe Tyr Lys Val Lys Glu
                245                 250                 255

Thr Leu Met Ile Gln Arg Ser Asn Gly Glu Gln Gly His Lys Arg Thr
            260                 265                 270

Glu Ser
```

<210> SEQ ID NO 5
<211> LENGTH: 801

```
<212> TYPE: DNA
<213> ORGANISM: Glycine max

<400> SEQUENCE: 5
atgtcaacat ggtctctgaa aattggcgta gttgggtttg gttccttcgg gcaatttctg      60
gcaaagacta tgatcaaaca aggccacact ctaaggcaa cttctcgtac tgactactcc     120
ctcttatgcc tcccaatggg tatccaattc ttcagggatg ttgctgcatt ccttgaggct     180
gacaacgatg tcatactcgt atgtacgtcc atcctatctc tctccgaggt tctcagctct     240
atgccactca cttgtctcaa agatcaaca ctctttgttg atgtcctttc agttaaagag      300
cacccaagaa atcttctaat taaggtattg ccagaggagt cagacatact gtgcacacac     360
ccaatgtttg gaccagatag tgggaaggat gggtggcaag atctaacatt cgtatatgat     420
aaagttcgaa tccgagatga agctatctgc tctagcttcc tccacatttt tgcaagtgag     480
ggctgcagga tgctacaaat gtcttgtgag gaacatgata aaatagctgc caagagtcaa     540
tttattacac acactatagg caggacattg gcagaaatgg atatcaagtc cacacctatt     600
gatacaaaag ctttcattc acttgttcaa ttgaaggaca ccaccatcag agatagtttt      660
gacttgtaca gtggattatt cttacataat aggtttgctg tacaagagtt ggagaatctt     720
gaacatgcct tgcacaaagt caagaaatg ctggttcaaa ggaagagtga ggagctgggt      780
ctagaaaaaa ctgaatgttg a                                               801

<210> SEQ ID NO 6
<211> LENGTH: 266
<212> TYPE: PRT
<213> ORGANISM: Glycine max

<400> SEQUENCE: 6

Met Ser Thr Trp Ser Leu Lys Ile Gly Val Val Gly Phe Gly Ser Phe
1               5                   10                  15

Gly Gln Phe Leu Ala Lys Thr Met Ile Lys Gln Gly His Thr Leu Arg
            20                  25                  30

Ala Thr Ser Arg Thr Asp Tyr Ser Leu Leu Cys Leu Pro Met Gly Ile
        35                  40                  45

Gln Phe Phe Arg Asp Val Ala Ala Phe Leu Glu Ala Asp Asn Asp Val
    50                  55                  60

Ile Leu Val Cys Thr Ser Ile Leu Ser Leu Ser Glu Val Leu Ser Ser
65                  70                  75                  80

Met Pro Leu Thr Cys Leu Lys Arg Ser Thr Leu Phe Val Asp Val Leu
                85                  90                  95

Ser Val Lys Glu His Pro Arg Asn Leu Leu Ile Lys Val Leu Pro Glu
            100                 105                 110

Glu Ser Asp Ile Leu Cys Thr His Pro Met Phe Gly Pro Asp Ser Gly
        115                 120                 125

Lys Asp Gly Trp Gln Asp Leu Thr Phe Val Tyr Asp Lys Val Arg Ile
    130                 135                 140

Arg Asp Glu Ala Ile Cys Ser Ser Phe Leu His Ile Phe Ala Ser Glu
145                 150                 155                 160

Gly Cys Arg Met Leu Gln Met Ser Cys Glu Glu His Asp Lys Ile Ala
                165                 170                 175

Ala Lys Ser Gln Phe Ile Thr His Thr Ile Gly Arg Thr Leu Ala Glu
            180                 185                 190

Met Asp Ile Lys Ser Thr Pro Ile Asp Thr Lys Gly Phe His Ser Leu
        195                 200                 205
```

Val Gln Leu Lys Asp Thr Thr Ile Arg Asp Ser Phe Asp Leu Tyr Ser
    210                 215                 220

Gly Leu Phe Leu His Asn Arg Phe Ala Val Gln Glu Leu Glu Asn Leu
225                 230                 235                 240

Glu His Ala Leu His Lys Val Lys Glu Met Leu Val Gln Arg Lys Ser
                245                 250                 255

Glu Glu Leu Gly Leu Glu Lys Thr Glu Cys
            260                 265

<210> SEQ ID NO 7
<211> LENGTH: 807
<212> TYPE: DNA
<213> ORGANISM: Medicago truncatula

<400> SEQUENCE: 7

| | | |
|---|---|---|
| atgtcatcat cttccaaaag tctgaaaatt ggcatagttg ggtttggcac ctttggccaa | 60 |
| ttttttgcaa atacaatgat taaacaaggt catactctaa ctgcaactag tagaacagat | 120 |
| tactctcaac tttgtgatca aatgggaatc catttcttca gggatattac agcattcctt | 180 |
| gatgctgata tggatgtcat attgttatgc acatctattt catcactatc tgaggttgtc | 240 |
| ggatcgatgc cactcgcttg tctgaagcga ccaacacttt ttgttgatgt tctttcagtc | 300 |
| aaagagcacc caaagaacct tctattaaag gtattgccag aggagtcaga tactctgc | 360 |
| acgcacccaa tgtttggacc agtgagtggg aaaaacggct ggcaaaatct gactttcatg | 420 |
| tttgataaag ttcgaataaa ggatgaagtt acatgctcta aatttcttca aatttttgca | 480 |
| agtgagggtt gcaagatggt agaaatgtca tgtgaggaac atgacaaagc agctgcaaag | 540 |
| agtcaattta tcacacacac aataggaagg acattggcag aaatggatat taaatccact | 600 |
| cctattgaca ccaagggctt tcaaacactt gttgagttga aaaaacctgt catgggttgt | 660 |
| agttttgatc tgtatagtgg attattcgtg tacaacagat cgccagaca agagctggaa | 720 |
| aaccttgaac atgctctaca caaagtcaaa gagatgctcg tccaaaggat cgatgaagga | 780 |
| cagaacccag aaagaactga gagttga | 807 |

<210> SEQ ID NO 8
<211> LENGTH: 268
<212> TYPE: PRT
<213> ORGANISM: Medicago truncatula

<400> SEQUENCE: 8

Met Ser Ser Ser Lys Ser Leu Lys Ile Gly Ile Val Gly Phe Gly
1               5                   10                  15

Thr Phe Gly Gln Phe Leu Ala Asn Thr Met Ile Lys Gln Gly His Thr
            20                  25                  30

Leu Thr Ala Thr Ser Arg Thr Asp Tyr Ser Gln Leu Cys Asp Gln Met
        35                  40                  45

Gly Ile His Phe Phe Arg Asp Ile Thr Ala Phe Leu Asp Ala Asp Met
    50                  55                  60

Asp Val Ile Leu Leu Cys Thr Ser Ile Ser Ser Leu Ser Glu Val Val
65                  70                  75                  80

Gly Ser Met Pro Leu Ala Cys Leu Lys Arg Pro Thr Leu Phe Val Asp
                85                  90                  95

Val Leu Ser Val Lys Glu His Pro Lys Asn Leu Leu Leu Lys Val Leu
            100                 105                 110

Pro Glu Glu Ser Asp Ile Leu Cys Thr His Pro Met Phe Gly Pro Val

```
            115                 120                 125
Ser Gly Lys Asn Gly Trp Gln Asn Leu Thr Phe Met Phe Asp Lys Val
    130                 135                 140

Arg Ile Lys Asp Glu Val Thr Cys Ser Lys Phe Leu Gln Ile Phe Ala
145                 150                 155                 160

Ser Glu Gly Cys Lys Met Val Glu Met Ser Cys Glu Glu His Asp Lys
                165                 170                 175

Ala Ala Ala Lys Ser Gln Phe Ile Thr His Thr Ile Gly Arg Thr Leu
            180                 185                 190

Ala Glu Met Asp Ile Lys Ser Thr Pro Ile Asp Thr Lys Gly Phe Gln
            195                 200                 205

Thr Leu Val Glu Leu Lys Lys Pro Val Met Gly Cys Ser Phe Asp Leu
    210                 215                 220

Tyr Ser Gly Leu Phe Val Tyr Asn Arg Phe Ala Arg Gln Glu Leu Glu
225                 230                 235                 240

Asn Leu Glu His Ala Leu His Lys Val Lys Glu Met Leu Val Gln Arg
                245                 250                 255

Ile Asp Glu Gly Gln Asn Pro Glu Arg Thr Glu Ser
            260                 265

<210> SEQ ID NO 9
<211> LENGTH: 291
<212> TYPE: PRT
<213> ORGANISM: Glycine max

<400> SEQUENCE: 9

Met Gly Ser Ser His His His His His Ser Ser Gly Leu Val Pro
1               5                   10                  15

Arg Gly Ser His Met Ser Thr Ser Ser Ser Gln Ser Leu Lys Ile
                20                  25                  30

Gly Ile Val Gly Phe Gly Asn Phe Gly Gln Phe Leu Ala Lys Thr Met
            35                  40                  45

Ile Lys Gln Gly His Thr Leu Thr Ala Thr Ser Arg Ser Asp Tyr Ser
    50                  55                  60

Glu Leu Cys Leu Gln Met Gly Ile His Phe Phe Arg Asp Val Ser Ala
65                  70                  75                  80

Phe Leu Thr Ala Asp Ile Asp Val Ile Val Leu Cys Thr Ser Ile Leu
                85                  90                  95

Ser Leu Ser Glu Val Val Gly Ser Met Pro Leu Thr Ser Leu Lys Arg
            100                 105                 110

Pro Thr Leu Phe Val Asp Val Leu Ser Val Lys Glu His Pro Arg Glu
        115                 120                 125

Leu Leu Leu Arg Glu Leu Pro Glu Asp Ser Asp Ile Leu Cys Thr His
    130                 135                 140

Pro Met Phe Gly Pro Gln Thr Ala Lys Asn Gly Trp Thr Asp His Thr
145                 150                 155                 160

Phe Met Tyr Asp Lys Val Arg Ile Arg Asp Glu Val Ile Cys Ser Asn
                165                 170                 175

Phe Ile Gln Ile Phe Ala Thr Glu Gly Cys Lys Met Val Gln Met Ser
            180                 185                 190

Cys Glu Glu His Asp Arg Ala Ala Ala Lys Ser Gln Phe Ile Thr His
        195                 200                 205

Thr Ile Gly Arg Thr Leu Gly Glu Met Asp Ile Gln Ser Thr Pro Ile
    210                 215                 220
```

```
Asp Thr Lys Gly Phe Glu Thr Leu Val Lys Leu Lys Glu Thr Met Met
225                 230                 235                 240

Arg Asn Ser Phe Asp Leu Tyr Ser Gly Leu Phe Val Tyr Asn Arg Phe
            245                 250                 255

Ala Arg Gln Glu Leu Glu Asn Leu Glu His Ala Leu His Lys Val Lys
        260                 265                 270

Glu Thr Leu Met Ile Gln Arg Thr Asn Gly Glu Gln Gly His Lys Arg
    275                 280                 285

Thr Glu Ser
    290

<210> SEQ ID NO 10
<211> LENGTH: 294
<212> TYPE: PRT
<213> ORGANISM: Glycine max

<400> SEQUENCE: 10

Met Gly Ser Ser His His His His His His Ser Ser Gly Leu Val Pro
1               5                   10                  15

Arg Gly Ser His Met Thr Thr Met Ser Thr Ser Ser Ser Ser Gln Ser
            20                  25                  30

Leu Lys Ile Gly Ile Val Gly Phe Gly Asn Phe Gly Gln Phe Leu Ala
        35                  40                  45

Lys Thr Met Ile Lys Gln Gly His Thr Leu Thr Ala Thr Ser Arg Ser
50                  55                  60

Asp Tyr Ser Gln Leu Cys Leu Gln Met Gly Ile His Phe Phe Arg Asp
65                  70                  75                  80

Val Ser Ala Phe Leu Ala Ala Asp Ile Asp Val Ile Val Leu Cys Thr
                85                  90                  95

Ser Ile Leu Ser Leu Ser Glu Val Val Gly Ser Met Pro Leu Thr Ser
            100                 105                 110

Leu Lys Arg Pro Thr Leu Phe Val Asp Val Leu Ser Val Lys Glu His
        115                 120                 125

Pro Arg Glu Leu Leu Leu Arg Glu Leu Pro Glu Asp Ser Asp Ile Leu
    130                 135                 140

Cys Thr His Pro Met Phe Gly Pro Gln Thr Ala Asn Asn Gly Trp Thr
145                 150                 155                 160

Asp His Thr Phe Met Tyr Asp Lys Val Arg Ile Arg Asp Glu Ala Thr
                165                 170                 175

Cys Ser Ser Phe Ile Gln Ile Phe Ala Thr Glu Gly Cys Lys Met Val
            180                 185                 190

Gln Met Ser Cys Glu Glu His Asp Arg Ala Ala Ala Lys Ser Gln Phe
        195                 200                 205

Ile Thr His Thr Ile Gly Arg Thr Leu Gly Glu Met Asp Ile Gln Ser
210                 215                 220

Thr Pro Ile Asp Thr Lys Gly Phe Glu Thr Leu Val Lys Leu Lys Glu
225                 230                 235                 240

Thr Met Met Arg Asn Ser Phe Asp Leu Tyr Ser Gly Leu Phe Val Tyr
                245                 250                 255

Asn Arg Phe Ala Arg Gln Glu Leu Glu Asn Leu Glu His Ala Phe Tyr
            260                 265                 270

Lys Val Lys Glu Thr Leu Met Ile Gln Arg Ser Asn Gly Glu Gln Gly
        275                 280                 285

His Lys Arg Thr Glu Ser
    290
```

<210> SEQ ID NO 11
<211> LENGTH: 286
<212> TYPE: PRT
<213> ORGANISM: Glycine max

<400> SEQUENCE: 11

```
Met Gly Ser Ser His His His His His Ser Ser Gly Leu Val Pro
1               5                   10                  15

Arg Gly Ser His Met Ser Thr Trp Ser Leu Lys Ile Gly Val Val Gly
            20                  25                  30

Phe Gly Ser Phe Gly Gln Phe Leu Ala Lys Thr Met Ile Lys Gln Gly
        35                  40                  45

His Thr Leu Arg Ala Thr Ser Arg Thr Asp Tyr Ser Leu Leu Cys Leu
    50                  55                  60

Pro Met Gly Ile Gln Phe Phe Arg Asp Val Ala Ala Phe Leu Glu Ala
65                  70                  75                  80

Asp Asn Asp Val Ile Leu Val Cys Thr Ser Ile Leu Ser Leu Ser Glu
                85                  90                  95

Val Leu Ser Ser Met Pro Leu Thr Cys Leu Lys Arg Ser Thr Leu Phe
            100                 105                 110

Val Asp Val Leu Ser Val Lys Glu His Pro Arg Asn Leu Leu Ile Lys
        115                 120                 125

Val Leu Pro Glu Glu Ser Asp Ile Leu Cys Thr His Pro Met Phe Gly
    130                 135                 140

Pro Asp Ser Gly Lys Asp Gly Trp Gln Asp Leu Thr Phe Val Tyr Asp
145                 150                 155                 160

Lys Val Arg Ile Arg Asp Glu Ala Ile Cys Ser Ser Phe Leu His Ile
                165                 170                 175

Phe Ala Ser Glu Gly Cys Arg Met Leu Gln Met Ser Cys Glu Glu His
            180                 185                 190

Asp Lys Ile Ala Ala Lys Ser Gln Phe Ile Thr His Thr Ile Gly Arg
        195                 200                 205

Thr Leu Ala Glu Met Asp Ile Lys Ser Thr Pro Ile Asp Thr Lys Gly
    210                 215                 220

Phe His Ser Leu Val Gln Leu Lys Asp Thr Thr Ile Arg Asp Ser Phe
225                 230                 235                 240

Asp Leu Tyr Ser Gly Leu Phe Leu His Asn Arg Phe Ala Val Gln Glu
                245                 250                 255

Leu Glu Asn Leu Glu His Ala Leu His Lys Val Lys Glu Met Leu Val
            260                 265                 270

Gln Arg Lys Ser Glu Glu Leu Gly Leu Glu Lys Thr Glu Cys
        275                 280                 285
```

<210> SEQ ID NO 12
<211> LENGTH: 288
<212> TYPE: PRT
<213> ORGANISM: Medicago truncatula

<400> SEQUENCE: 12

```
Met Gly Ser Ser His His His His His Ser Ser Gly Leu Val Pro
1               5                   10                  15

Arg Gly Ser His Met Ser Ser Ser Lys Ser Leu Lys Ile Gly Ile
            20                  25                  30

Val Gly Phe Gly Thr Phe Gly Gln Phe Leu Ala Asn Thr Met Ile Lys
        35                  40                  45
```

Gln Gly His Thr Leu Thr Ala Thr Ser Arg Thr Asp Tyr Ser Gln Leu
            50                  55                  60

Cys Asp Gln Met Gly Ile His Phe Phe Arg Asp Ile Thr Ala Phe Leu
 65                  70                  75                  80

Asp Ala Asp Met Asp Val Ile Leu Leu Cys Thr Ser Ile Ser Ser Leu
                 85                  90                  95

Ser Glu Val Val Gly Ser Met Pro Leu Ala Cys Leu Lys Arg Pro Thr
                100                 105                 110

Leu Phe Val Asp Val Leu Ser Val Lys Glu His Pro Lys Asn Leu Leu
            115                 120                 125

Leu Lys Val Leu Pro Glu Glu Ser Asp Ile Leu Cys Thr His Pro Met
        130                 135                 140

Phe Gly Pro Val Ser Gly Lys Asn Gly Trp Gln Asn Leu Thr Phe Met
145                 150                 155                 160

Phe Asp Lys Val Arg Ile Lys Asp Glu Val Thr Cys Ser Lys Phe Leu
                165                 170                 175

Gln Ile Phe Ala Ser Glu Gly Cys Lys Met Val Glu Met Ser Cys Glu
            180                 185                 190

Glu His Asp Lys Ala Ala Ala Lys Ser Gln Phe Ile Thr His Thr Ile
        195                 200                 205

Gly Arg Thr Leu Ala Glu Met Asp Ile Lys Ser Thr Pro Ile Asp Thr
    210                 215                 220

Lys Gly Phe Gln Thr Leu Val Glu Leu Lys Lys Pro Val Met Gly Cys
225                 230                 235                 240

Ser Phe Asp Leu Tyr Ser Gly Leu Phe Val Tyr Asn Arg Phe Ala Arg
                245                 250                 255

Gln Glu Leu Glu Asn Leu Glu His Ala Leu His Lys Val Lys Glu Met
            260                 265                 270

Leu Val Gln Arg Ile Asp Glu Gly Gln Asn Pro Glu Arg Thr Glu Ser
        275                 280                 285

<210> SEQ ID NO 13
<211> LENGTH: 322
<212> TYPE: PRT
<213> ORGANISM: Medicago truncatula

<400> SEQUENCE: 13

Met Ser Asn Ser Pro Ser Leu Lys Ile Gly Ile Val Gly Phe Gly Ser
 1               5                  10                  15

Phe Gly Gln Phe Leu Ala Lys Thr Met Ile Lys Gln Gly His Thr Leu
            20                  25                  30

Thr Ala Thr Ser Arg Thr Asp Tyr Ser His Thr Cys Leu Gln Leu Gly
        35                  40                  45

Ile Gln Phe Phe Arg Asp Val Gly Thr Phe Ile Glu Ala Asn Asn Asp
    50                  55                  60

Val Ile Leu Ile Cys Thr Ser Ile Met Ser Phe Thr Lys Val Leu Ser
 65                  70                  75                  80

Ser Met Pro Leu Ala Cys Leu Lys Lys Pro Thr Thr Leu Phe Val Asp
                 85                  90                  95

Val Leu Ser Val Lys Glu His Pro Arg Glu Val Leu Leu Arg Val Ile
                100                 105                 110

Leu Tyr Tyr Phe Phe Lys Leu Leu Ser Met Ser Cys Leu Met Ser Val
            115                 120                 125

Cys Ala Leu His Ser Leu Arg Asp Ile Met Phe Gly Ile Met Val Asp

```
           130                 135                 140
Phe Asp Lys Thr Arg Arg Lys Phe Lys His Ala Leu Ile Leu Leu Trp
145                 150                 155                 160

Pro Met Phe Ala Leu Gln Val Leu Pro Glu Glu Ser Asp Ile Leu Cys
                165                 170                 175

Thr His Pro Met Phe Gly Pro Glu Ser Gly Lys Asn Gly Trp Lys Asp
            180                 185                 190

Leu Asn Phe Met Tyr Asp Lys Val Arg Ile His Asp Glu Ala Thr Cys
                195                 200                 205

Ser Asn Phe Leu His Ile Phe Ala Ser Glu Gly Cys Lys Met Leu Gln
        210                 215                 220

Met Ser Cys Glu Glu His Asp Lys Ile Ala Ala Lys Ser Gln Phe Ile
225                 230                 235                 240

Thr His Thr Ile Gly Arg Thr Leu Ala Glu Met Asp Ile Glu Ser Thr
                245                 250                 255

Pro Ile Asp Thr Lys Gly Phe Gln Thr Leu Thr Gln Leu Lys Asn Thr
            260                 265                 270

Thr Met Arg Asp Ser Phe Asp Leu Tyr Ser Gly Leu Phe Val His Asn
        275                 280                 285

Arg Phe Ala Lys Gln Glu Leu Glu Asn Leu Gln Arg Ala Leu Asp Arg
    290                 295                 300

Val Lys Glu Met Leu Val Gln Arg Met Arg Glu Glu Leu Gly Pro Glu
305                 310                 315                 320

Lys Asp

<210> SEQ ID NO 14
<211> LENGTH: 282
<212> TYPE: PRT
<213> ORGANISM: Populus trichocarpa

<400> SEQUENCE: 14

Met Ala Val Ser Ser Ser Ser Ser Ser Ser Ser Ser Ser Ser Ser Ser
1               5                   10                  15

Ser Pro Ser Arg Asn Leu Lys Ile Gly Ile Val Gly Phe Gly Pro Phe
            20                  25                  30

Ala Gln Phe Leu Ala Lys Ile Met Ile Lys Gln Gly His Thr Leu Arg
        35                  40                  45

Ala Thr Ser Arg Ser Asp His Ser Ser Leu Cys Gln Asp Leu Gly Ile
    50                  55                  60

Ser Phe Phe Arg Asp Thr Gly Thr Phe Leu Glu Ala Asn Asn Asp Val
65                  70                  75                  80

Ile Leu Ile Cys Thr Ser Ile Leu Ser Leu Ser Lys Val Leu Asn Thr
                85                  90                  95

Met Pro Leu His Cys Leu Lys Arg Ser Pro Leu Phe Val Asp Val Leu
            100                 105                 110

Ser Val Lys Glu Tyr Pro Arg Asp Ile Leu Leu Lys Val Leu Pro Glu
        115                 120                 125

Glu Leu Asp Val Leu Cys Thr His Pro Met Phe Gly Pro Glu Ser Gly
    130                 135                 140

Lys Asn Gly Trp Lys Asp Leu Ala Phe Met Tyr Glu Arg Val Arg Ile
145                 150                 155                 160

Lys Asp Glu Ala Thr Cys Ser Ser Phe Leu Arg Ile Phe Glu Thr Glu
                165                 170                 175

Gly Cys Arg Met Leu Glu Met Ser Cys Glu Glu His Asp Met Val Ala
```

```
                    180                 185                 190
Ala Arg Ser Gln Phe Leu Thr His Thr Ile Gly Arg Ile Leu Ser Glu
                195                 200                 205

Met Glu Val Lys Pro Thr Ser Met Ser Thr Lys Gly Phe Glu Thr Leu
            210                 215                 220

Ile His Leu Lys Glu Ser Thr Met Lys Asp Ser Asp Leu Phe Ser
225                 230                 235                 240

Gly Leu Phe Val Tyr Asn Arg Phe Ala Lys Gln Glu Leu Lys Asn Leu
                245                 250                 255

Glu Leu Ser Leu Glu Lys Val Lys Gln Met Leu Gln Asp Lys Met Thr
            260                 265                 270

Glu Glu Gln Asn Leu Asn Glu Ser Lys Phe
            275                 280

<210> SEQ ID NO 15
<211> LENGTH: 272
<212> TYPE: PRT
<213> ORGANISM: Solanum lycopersicum

<400> SEQUENCE: 15

Met Ser Ser Ser Ser Cys Gln Pro Lys Thr Leu Arg Ile Gly Ile
1               5                   10                  15

Ile Gly Phe Gly Pro Phe Ala Gln Phe Leu Ala Lys Thr Met Met Lys
                20                  25                  30

Gln Gly His Cys Ile His Val Thr Ser Arg Ser Asp Tyr Ser Glu Leu
            35                  40                  45

Cys Thr Asp Leu Gly Ile Leu Phe Phe Arg Asp Met Gly Ala Phe Leu
        50                  55                  60

Glu Ser Asp Asn Glu Val Ile Met Ile Ser Thr Ser Ile Leu Ser Leu
65                  70                  75                  80

Ser Gln Val Val Glu Ser Ile Pro Phe Asn Cys Leu Lys Arg Pro Thr
                85                  90                  95

Leu Phe Val Asp Val Leu Ser Val Lys Glu His Pro Lys Asp Val Leu
                100                 105                 110

Leu Arg Met Met Pro Arg Glu Cys Asp Leu Leu Cys Thr His Pro Met
            115                 120                 125

Phe Gly Pro Glu Ser Gly Lys Asp Gly Trp Glu Asp Leu Thr Phe Met
        130                 135                 140

Tyr Asp Met Val Arg Ile Arg Asp Gln Pro Leu Cys Ser Ser Phe Leu
145                 150                 155                 160

His Ile Phe Ser Ser Glu Gly Cys Lys Met Leu Glu Met Thr Cys Glu
                165                 170                 175

Lys His Asp Arg Leu Ala Ala Gln Ser Gln Phe Leu Thr His Thr Ile
            180                 185                 190

Gly Arg Ile Leu Ser Glu Met Glu Val Glu Pro Thr Pro Ile Asp Thr
        195                 200                 205

Lys Gly Phe Gln Lys Leu Val Gln Val Lys Glu Ser Ser Val Lys Asp
    210                 215                 220

Ser Phe Asp Leu Phe Ser Gly Leu Phe Ile His Asn Arg Phe Ala Arg
225                 230                 235                 240

Gln Gln Met Lys Asn Leu Glu Val Ala Leu Glu Lys Thr Lys Glu Lys
                245                 250                 255

Leu Gln Glu Arg Ser Lys Glu Leu Gln Asp Pro Ile Ile Ser Lys Phe
            260                 265                 270
```

<210> SEQ ID NO 16
<211> LENGTH: 345
<212> TYPE: PRT
<213> ORGANISM: Ricinus communis

<400> SEQUENCE: 16

Met Ser Pro Pro Ser Ser Thr Thr Arg Ser Leu Lys Ile Gly
1               5                   10                  15

Ile Ile Gly Phe Gly Arg Phe Gly Gln Phe Leu Ala Lys Thr Met Ile
            20                  25                  30

Lys Gln Gly His Thr Leu Arg Ala Thr Ser Arg Ser Asp His Ser His
        35                  40                  45

Leu Cys Glu Asp Leu Gly Ile Ser Tyr Phe Arg Asp Val Ile Lys Phe
    50                  55                  60

Leu Glu Ala Asp Asn Asp Val Ile Leu Ile Cys Thr Ser Ile Leu Ser
65                  70                  75                  80

Leu Gln Glu Val Leu Asn Ser Met Pro Leu His Ser Leu Lys Arg Gln
                85                  90                  95

Arg Thr Leu Phe Ala Asp Val Leu Ser Val Lys Glu Tyr Pro Arg Asp
            100                 105                 110

Val Leu Thr Lys Val Leu Pro Glu Glu Ser Asp Ile Leu Cys Thr His
        115                 120                 125

Pro Met Phe Gly Pro Glu Ser Gly Lys His Gly Trp Lys Asp Leu Ala
    130                 135                 140

Phe Val Tyr Asp Lys Val Arg Val Arg Asp Glu Ala Thr Cys Ser Ser
145                 150                 155                 160

Phe Leu Lys Ile Phe Glu Thr Glu Gly Cys Arg Met Leu Glu Met Ser
                165                 170                 175

Cys Glu Glu His Asp Arg Met Ala Ala Lys Ser Gln Phe Leu Thr His
            180                 185                 190

Thr Ile Gly Arg Ile Phe Ser Glu Met Glu Ile Lys Ser Thr Pro Met
        195                 200                 205

Ser Thr Lys Gly Phe Glu Thr Leu Val Arg Leu Lys Asp Asp Thr Thr
    210                 215                 220

Lys Asp Ser Phe Asp Leu Phe Ser Gly Leu Phe Leu Cys Asn Arg Phe
225                 230                 235                 240

Ala Lys Gln Glu Leu Lys Asn Leu Glu Leu Ala Leu Glu Lys Lys Thr
                245                 250                 255

Phe Arg Tyr His Ser Ile Gly His Ser Tyr Ala Ser Lys Leu Cys Leu
            260                 265                 270

Ala Leu Lys Phe Gln Thr Gln Thr Gly His Gln Thr Gly Lys Gly Ala
        275                 280                 285

Glu Ser Lys Asp Thr Gly Ile Ala Phe Ser Asp Gly Asn Leu Ile Pro
    290                 295                 300

Lys Arg Gln Leu Glu Phe Gly Phe His Gly Ala Lys Ser Gly Leu Thr
305                 310                 315                 320

Lys Gly His Lys Phe Trp Glu Lys His Leu Thr Ile Leu Val Phe Ile
                325                 330                 335

Gly Arg Thr Lys Val Gln Arg Asp Ile
            340                 345

<210> SEQ ID NO 17
<211> LENGTH: 269
<212> TYPE: PRT
<213> ORGANISM: Phaseolus vulgaris

<400> SEQUENCE: 17

```
Met Ser Ser Ser Ser Ser Ser Gln Ser Leu Lys Ile Gly Ile Val
1               5                   10                  15

Gly Phe Gly Thr Phe Gly Gln Phe Leu Ala Lys Thr Met Ile Lys Gln
            20                  25                  30

Gly His Ser Leu Thr Ala Thr Ser Arg Ser Asp Tyr Ser Asp Leu Cys
            35                  40                  45

Leu Gln Met Gly Ile His Phe Tyr Gly Asp Val Thr Ala Phe Leu Ala
    50                  55                  60

Ser Asp Ile Asp Val Ile Val Leu Cys Thr Ser Ile Leu Ser Leu Ser
65                  70                  75                  80

Glu Val Val Gly Ser Met Pro Leu Ala Ser Leu Lys Arg Pro Thr Leu
                85                  90                  95

Phe Val Asp Val Leu Ser Val Lys Glu His Pro Arg Glu Leu Leu Leu
            100                 105                 110

Arg Glu Leu Pro Glu His Ser Asp Ile Leu Cys Thr His Pro Met Phe
            115                 120                 125

Gly Pro Val Ser Gly Lys Asn Gly Trp Lys Gly Leu Thr Phe Met Tyr
    130                 135                 140

Asp Lys Val Arg Ile Arg Asn Glu Ala Ile Cys Ser Ser Phe Ile Gln
145                 150                 155                 160

Ile Phe Ala Ser Glu Gly Cys Lys Met Val Gln Met Thr Cys Glu Glu
                165                 170                 175

His Asp Lys Ala Ala Lys Ser Gln Phe Ile Thr His Thr Ile Gly
            180                 185                 190

Arg Thr Leu Ala Glu Met Asp Ile Lys Ser Thr Pro Ile Asp Thr Lys
            195                 200                 205

Gly Phe Glu Glu Leu Val Lys Leu Lys Glu Thr Met Ile Gly Asn Ser
    210                 215                 220

Phe Asp Leu Phe Ser Gly Leu Phe Val Tyr Asn Arg Phe Ala Arg Gln
225                 230                 235                 240

Glu Leu Glu Asn Leu Glu His Ala Leu Gln Lys Val Lys Glu Thr Leu
                245                 250                 255

Val Glu Arg Lys Asn Glu Glu Gln Gly Gln Glu Lys Asn
            260                 265
```

<210> SEQ ID NO 18
<211> LENGTH: 270
<212> TYPE: PRT
<213> ORGANISM: Gossypium raimondii

<400> SEQUENCE: 18

```
Met Ser Ser Ser Ser Ser Leu Pro Leu Gln Thr Leu Lys Ile Gly Ile
1               5                   10                  15

Val Gly Phe Gly Thr Phe Gly Gln Phe Leu Ala Lys Thr Met Ile Lys
            20                  25                  30

Gln Gly His Thr Thr Arg Ala Thr Ser Arg Thr Asp Tyr Ser Gln Leu
        35                  40                  45

Cys His Gln Leu Asp Val Pro Phe Phe Arg Asp Val Ile Pro Phe Leu
    50                  55                  60

Glu Ala Asp Asn Asp Val Ile Leu Ile Cys Thr Ser Ile Leu Ser Leu
65                  70                  75                  80

Ser Glu Val Leu Asn Ser Met Pro Leu Arg Arg Leu Lys Arg His Thr
                85                  90                  95
```

```
Leu Phe Val Asp Val Leu Ser Val Lys Glu His Pro Arg Asn Val Leu
            100                 105                 110

Leu Gln Val Leu Pro Glu Asn Met Asp Val Leu Cys Thr His Pro Met
        115                 120                 125

Phe Gly Pro Glu Ser Gly Lys Asn Gly Trp Lys Asp Leu Pro Leu Val
130                 135                 140

Tyr Glu Lys Val Arg Val Arg Asn Glu Thr Arg Cys Ser Ser Phe Leu
145                 150                 155                 160

His Ile Phe Glu Ser Glu Gly Cys Arg Met Val Glu Met Ser Cys Glu
                165                 170                 175

Glu His Asp Lys Val Ala Ala Arg Ser Gln Phe Leu Ser His Ser Ile
            180                 185                 190

Gly Arg Ile Leu Ala Glu Met Gly Ile Glu Ser Thr Ser Met Asn Thr
        195                 200                 205

Lys Ser Phe Glu Thr Leu Val Lys Leu Lys Glu Ser Ala Thr Asn Asp
    210                 215                 220

Ser Phe Asp Leu Phe Ser Gly Leu Phe Ile His Asn Arg Phe Ala Gln
225                 230                 235                 240

Gln Glu Leu Met Asn Leu Glu Gln Ser Phe Glu Lys Val Lys Gln Arg
                245                 250                 255

Leu Leu Lys Lys Met Ser Glu Gln Gln Ser Leu Ser Ser Val
            260                 265                 270

<210> SEQ ID NO 19
<211> LENGTH: 278
<212> TYPE: PRT
<213> ORGANISM: Theobroma cacao

<400> SEQUENCE: 19

Met Ser Ser Ser Ser Asp Ser Phe Ser Ser Leu Thr Leu Asn Ile Gly
1               5                   10                  15

Ile Val Gly Phe Gly Thr Phe Gly Gln Phe Leu Ala Lys Thr Met Ile
            20                  25                  30

Gln Gln Gly His Thr Ile Ser Ala Thr Ser Arg Thr Asp Tyr Ser Gln
        35                  40                  45

Leu Cys His Gln Leu Gly Ile Ser Phe Phe Arg Asp Val Ala Ala Phe
    50                  55                  60

Val Glu Ala Asp Asn Asp Val Ile Leu Ile Ser Thr Ser Ile Leu Ser
65                  70                  75                  80

Leu Ser Lys Met Leu Lys Ser Ile Pro Phe Arg Cys Leu Lys Arg Arg
                85                  90                  95

Thr Leu Phe Val Asp Val Leu Ser Val Lys Glu His Pro Arg Asp Val
            100                 105                 110

Leu Leu Gln Val Leu Pro Glu Glu Met Asp Leu Leu Cys Thr His Pro
        115                 120                 125

Met Phe Gly Pro Glu Ser Gly Lys Ser Gly Trp Glu Asp Leu Val Leu
    130                 135                 140

Met Tyr Asp Lys Val Arg Val Arg Asp Glu Ala Thr Cys Ser Ser Phe
145                 150                 155                 160

Leu Arg Ile Phe Glu Arg Gln Gly Cys Arg Met Met Gln Met Ser Cys
                165                 170                 175

Glu Glu His Asp Arg Leu Ala Ala Arg Ser Gln Phe Leu Thr His Ala
            180                 185                 190

Ile Gly Arg Ile Leu Ser Glu Thr Gly Ile Glu Ser Thr Ser Ile Asn
```

```
                    195                 200                 205
Thr Lys Ser Phe Glu Thr Leu Val Lys Leu Lys Glu Ser Thr Thr Asn
    210                 215                 220

Asp Ser Phe Asp Leu Phe Ser Gly Leu Phe Ile His Asn Arg Phe Ala
225                 230                 235                 240

Lys Gln Glu Leu Met Asn Leu Glu His Ala Phe Gln Met Val Lys Lys
                245                 250                 255

Lys Leu Leu Gln Thr Ala Asn Glu Glu Gln Ile Pro Asn Lys Ser Asn
            260                 265                 270

His Gln Met Asp Ser Cys
            275

<210> SEQ ID NO 20
<211> LENGTH: 275
<212> TYPE: PRT
<213> ORGANISM: Citrus sinensis

<400> SEQUENCE: 20

Met Ala Val Ser Ser Pro Ser Ser Ser Thr Leu Lys Ile Gly Ile
1               5                   10                  15

Ile Gly Phe Gly Pro Phe Gly Gln Phe Leu Ala Lys Thr Met Ile Lys
                20                  25                  30

Gln Gly His Ile Leu Arg Ala Thr Ser Arg Thr Asp His Ser Gln Leu
            35                  40                  45

Cys His Arg Ser Gly Ile Ser Phe Phe Ser Asp Lys Arg Ala Phe Leu
        50                  55                  60

Glu Ala Asp Asn Asp Val Ile Leu Ile Ser Thr Ile Leu Ser Leu
65                  70                  75                  80

Ser Glu Val Leu Asn Ser Leu Pro Val His Cys Leu Gln Arg Arg Thr
                85                  90                  95

Leu Ile Ala Asp Val Leu Ser Val Lys Glu Tyr Pro Arg Asn Val Leu
            100                 105                 110

Leu Gln Val Leu Pro Glu Glu Met Asp Val Leu Cys Thr His Pro Met
        115                 120                 125

Phe Gly Pro Glu Ser Gly Gln Asn Gly Trp Lys Asp Phe Ala Phe Val
    130                 135                 140

Tyr Glu Lys Val Arg Ile Arg Asp Glu Ala Thr Cys Ser Ser Phe Leu
145                 150                 155                 160

Arg Ile Phe Glu Ser Glu Gly Cys Lys Met Leu Glu Met Ser Cys Glu
                165                 170                 175

Glu His Asp Lys Val Ala Ala Lys Ser Gln Phe Leu Thr His Thr Ile
            180                 185                 190

Gly Arg Val Leu Ser Glu Leu Glu Ile Gln Ser Thr Ser Met Asn Thr
        195                 200                 205

Lys Gly Phe Glu Thr Leu Ile Arg Leu Lys Glu Ser Ser Val Asn Asp
    210                 215                 220

Ser Phe Asp Leu Phe Ser Gly Leu Tyr Ile His Asn Arg Phe Ala Lys
225                 230                 235                 240

Gln Glu Leu Leu Asp Leu Glu Ala Ala Phe Glu Lys Val Lys His Lys
                245                 250                 255

Leu Gln Gln Lys Met Glu Glu Val Gln Leu Glu Gln Ser Pro Asn Glu
            260                 265                 270

Ser Lys Leu
        275
```

<210> SEQ ID NO 21
<211> LENGTH: 275
<212> TYPE: PRT
<213> ORGANISM: Citrus clementina

<400> SEQUENCE: 21

```
Met Ala Val Ser Ser Pro Ser Ser Ser Thr Leu Lys Ile Gly Ile
 1               5                  10                  15

Ile Gly Phe Gly Pro Phe Gly Gln Phe Leu Ala Lys Thr Met Ile Lys
             20                  25                  30

Gln Gly His Ile Leu Arg Ala Thr Ser Arg Thr Asp His Ser Gln Leu
         35                  40                  45

Cys His Arg Ser Gly Ile Ser Phe Phe Ser Asp Lys Arg Ala Phe Leu
     50                  55                  60

Glu Ala Asp Asn Asp Val Ile Leu Ile Ser Thr Ser Ile Leu Ser Leu
 65                  70                  75                  80

Ser Glu Val Leu Asn Ser Leu Pro Val His Cys Leu Gln Arg Arg Thr
                 85                  90                  95

Leu Ile Ala Asp Val Leu Ser Val Lys Glu Tyr Pro Arg Asn Val Leu
            100                 105                 110

Leu Gln Val Leu Pro Glu Glu Met Asp Val Leu Cys Thr His Pro Met
        115                 120                 125

Phe Gly Pro Glu Ser Gly Gln Asn Gly Trp Lys Asp Phe Ala Phe Val
    130                 135                 140

Tyr Glu Lys Val Arg Ile Arg Asp Glu Ala Thr Cys Ser Ser Phe Leu
145                 150                 155                 160

Arg Ile Phe Glu Ser Glu Gly Cys Lys Met Leu Glu Met Ser Cys Glu
                165                 170                 175

Glu His Asp Lys Val Ala Ala Lys Ser Gln Phe Leu Thr His Thr Ile
            180                 185                 190

Gly Arg Val Leu Ser Glu Leu Glu Ile Gln Ser Thr Ser Met Asn Thr
        195                 200                 205

Lys Gly Phe Glu Thr Leu Ile Arg Leu Lys Glu Ser Ser Val Asn Asp
    210                 215                 220

Ser Phe Asp Leu Phe Ser Gly Leu Tyr Ile His Asn Arg Phe Ala Lys
225                 230                 235                 240

Gln Glu Leu Leu Asp Leu Glu Ala Ala Phe Glu Lys Val Lys His Lys
                245                 250                 255

Leu Gln Gln Lys Met Glu Glu Val Gln Leu Glu Gln Ser Pro Asn Glu
            260                 265                 270

Ser Lys Leu
        275
```

<210> SEQ ID NO 22
<211> LENGTH: 272
<212> TYPE: PRT
<213> ORGANISM: Eucalyptus grandis

<400> SEQUENCE: 22

```
Met Ser Ala Ser Val Pro Ala Ser Val Ser Ser Arg Ser Leu Lys
 1               5                  10                  15

Ile Gly Ile Val Gly Phe Gly Thr Phe Ser Gln Phe Leu Ala Lys Thr
             20                  25                  30

Met Ile Lys Gln Gly His Ser Leu Arg Ala Thr Ser Arg Thr Asp Tyr
         35                  40                  45
```

```
Ser Gln Leu Cys Ala Asp Met Gly Ile Ala Phe Phe Ser Asp Val Ala
    50                  55                  60

Ala Phe Leu Gly Ala Asp Asn Asp Val Ile Met Ile Cys Thr Ser Ile
65                  70                  75                  80

Leu Ser Leu Ser Gln Val Leu Arg Ser Met Pro Phe Thr Ala Leu Lys
                85                  90                  95

Gln Pro Ala Leu Phe Val Asp Val Leu Ser Val Lys Glu Tyr Ala Arg
            100                 105                 110

Asp Thr Leu Leu Gln Val Leu Pro Glu Asp Ser Asp Val Leu Cys Thr
            115                 120                 125

His Pro Met Phe Gly Pro Glu Ser Gly Lys His Gly Trp Arg Asp Leu
130                 135                 140

Asn Phe Met Tyr Glu Arg Val Arg Val Arg Asp Glu Thr Cys Ser
145                 150                 155                 160

Ser Phe Leu Lys Ile Phe Glu Ile Glu Gly Cys Arg Met Leu Glu Met
                165                 170                 175

Ser Cys Thr Glu His Asp Glu Leu Ala Ala Lys Ser Gln Phe Ile Thr
            180                 185                 190

His Thr Ile Gly Arg Phe Leu Ser Glu Met Asp Ile Glu Ser Thr Pro
            195                 200                 205

Ile Asp Thr Lys Gly Phe Glu Ala Leu Val Gln Leu Arg Lys Asn Thr
210                 215                 220

Glu Ser Asn Ser Phe Asp Leu Phe Ser Gly Leu Tyr Ile His Asn Arg
225                 230                 235                 240

Phe Ala Lys Gln Glu Leu Lys Asn Leu Glu Phe Ala Phe Glu Lys Leu
                245                 250                 255

Lys His Lys Leu Leu Lys Arg Asn Asp Glu Glu Gln Glu Val Asn Gln
            260                 265                 270

<210> SEQ ID NO 23
<211> LENGTH: 272
<212> TYPE: PRT
<213> ORGANISM: Vitis vinifera

<400> SEQUENCE: 23

Met Ala Val Ser Ser Ser Pro Leu Ser Arg Thr Leu Arg Ile Gly
1               5                   10                  15

Ile Val Gly Phe Gly Pro Phe Gly Gln Phe Leu Ala Lys Thr Met Met
                20                  25                  30

Lys Gln Gly His Thr Leu Thr Ala Thr Ser Arg Ser Asp His Ser Gln
            35                  40                  45

Leu Cys Ala Arg Leu Gly Ile Ser Phe Phe Arg Gly Met Asn Glu Phe
    50                  55                  60

Ile Glu Ala Glu Asn Asp Val Ile Met Leu Cys Thr Ser Ile Leu Ser
65                  70                  75                  80

Leu Thr Glu Val Leu Glu Ser Leu Pro Leu His Cys Leu Lys Arg Pro
                85                  90                  95

Thr Leu Phe Ala Asp Val Leu Ser Val Lys Glu Gly Pro Arg Glu Val
            100                 105                 110

Leu Leu Gln Val Leu Pro Glu Glu Ser Asp Val Leu Cys Thr His Pro
            115                 120                 125

Met Phe Gly Pro Glu Ser Gly Arg Asp Gly Trp Asn Gly Leu Ala Phe
130                 135                 140

Met Tyr Glu Arg Val Arg Ile Arg Asp Glu Ala Thr Cys Ser Ser Phe
145                 150                 155                 160
```

```
Leu His Ile Phe Glu Ser Gly Cys Arg Met Leu Glu Met Ser Cys
            165                 170                 175

Glu Glu His Asp Lys Leu Ala Ala Arg Ser Gln Phe Leu Thr His Thr
        180                 185                 190

Ile Gly Arg Ile Leu Ser Glu Met Glu Ile Glu Pro Thr Pro Ile Asp
            195                 200                 205

Thr Lys Gly Phe Gln Thr Leu Ile Gln Leu Lys Asp Ser Thr Ile Arg
    210                 215                 220

Asp Ser Phe Asp Leu Tyr Ser Gly Leu Phe Val His Asn Lys Phe Ala
225                 230                 235                 240

Lys Gln Glu Leu Asn Asn Leu Val Leu Ala Phe Glu Lys Val Lys Gln
            245                 250                 255

Lys Leu Glu Glu Met Asn Glu Lys Ser Asp Leu Ser Met Gln Pro Leu
        260                 265                 270
```

<210> SEQ ID NO 24
<211> LENGTH: 274
<212> TYPE: PRT
<213> ORGANISM: Solanum tuberosum

<400> SEQUENCE: 24

```
Met Ser Ser Ser Ser Ser Ser Ser Gln Pro Lys Thr Leu Arg Ile
1               5                   10                  15

Gly Ile Ile Gly Phe Gly Pro Phe Ala Gln Phe Leu Ala Lys Thr Met
            20                  25                  30

Met Lys Gln Gly His Phe Ile Arg Val Thr Ser Arg Ser Asp Tyr Ser
        35                  40                  45

Glu Leu Cys Thr Asn Leu Gly Ile Leu Phe Phe Arg Asp Met Gly Ala
    50                  55                  60

Phe Leu Glu Ser Asp Asn Glu Val Ile Met Ile Ser Thr Ser Ile Leu
65                  70                  75                  80

Ser Leu Ser Arg Val Val Glu Ser Ile Pro Phe Asn Cys Leu Lys Arg
            85                  90                  95

Pro Thr Leu Phe Val Asp Val Leu Ser Val Lys Glu His Pro Lys Asp
        100                 105                 110

Val Leu Leu Arg Ile Met Pro Glu Glu Cys Asp Leu Leu Cys Thr His
    115                 120                 125

Pro Met Phe Gly Pro Glu Ser Gly Lys Asp Gly Trp Thr Asp Leu Thr
130                 135                 140

Phe Met Tyr Asp Met Val Arg Ile Arg Asp Gln Pro Leu Cys Ser Ser
145                 150                 155                 160

Phe Leu His Ile Phe Ser Ser Glu Gly Cys Lys Met Leu Glu Met Thr
            165                 170                 175

Cys Glu Glu His Asp Arg Leu Ala Ala Gln Ser Gln Phe Leu Thr His
        180                 185                 190

Thr Ile Gly Arg Ile Leu Ser Glu Met Glu Val Glu Pro Thr Pro Ile
    195                 200                 205

Asp Thr Lys Gly Phe Gln Lys Leu Val Gln Val Lys Glu Ser Ala Val
210                 215                 220

Lys Asp Ser Phe Asp Leu Phe Ser Gly Leu Phe Ile His Asn Arg Phe
225                 230                 235                 240

Ala Arg Gln Gln Met Lys Asn Leu Glu Val Ala Leu Glu Lys Thr Lys
            245                 250                 255

Glu Lys Leu Gln Glu Arg Ser Lys Glu Leu Gln Asp Pro Ile Ile Ser
```

260                 265                 270

Lys Phe

<210> SEQ ID NO 25
<211> LENGTH: 263
<212> TYPE: PRT
<213> ORGANISM: Mimulus guttatus

<400> SEQUENCE: 25

Met Ser Ser Leu Pro Leu Lys Ile Gly Ile Ile Gly Phe Gly Pro Phe
1               5                   10                  15

Ala Gln Phe Leu Val Lys Thr Met Ile Lys Gln Gly His Ser Ile Arg
            20                  25                  30

Ala Asn Ser Arg Ser Asp Tyr Thr Asp Leu Cys Asn Gln Leu Gly Ile
        35                  40                  45

Ser Phe Phe Ser Asp Thr Thr Ala Phe Ile Glu Ser Gln Asn Asp Val
    50                  55                  60

Ile Leu Leu Cys Thr Ser Ile Leu Ser Leu Ser Lys Val Ile Lys Ser
65                  70                  75                  80

Leu Pro Leu Asp Cys Leu Lys Gln Pro Thr Leu Phe Val Asp Val Leu
                85                  90                  95

Ser Val Lys Glu His Pro Arg Asp Leu Met Leu Gln Val Leu Pro Arg
            100                 105                 110

Asp Ser Asp Val Leu Cys Thr His Pro Met Phe Gly Pro Glu Ser Gly
        115                 120                 125

Arg Asp Gly Trp Lys Asp Leu Ser Phe Met Tyr Asp Lys Val Arg Val
    130                 135                 140

Thr Asn Glu Ala Thr Cys Ser Ser Phe Leu Gln Ile Phe Ala Ser Glu
145                 150                 155                 160

Gly Cys Lys Met Met Glu Met Thr Cys Glu Glu His Asp Glu Leu Ser
                165                 170                 175

Ala Arg Ser Gln Phe Val Thr His Thr Val Gly Arg Val Leu Ala Glu
            180                 185                 190

Met Glu Ile Glu Ser Thr Pro Ile Asp Thr Lys Gly Phe Gln Lys Leu
        195                 200                 205

Val Gln Val Lys Glu Ser Ala Ser Arg Asp Ser Phe Asp Leu Phe Ser
    210                 215                 220

Gly Leu Phe Ile His Asn Arg Phe Ala Lys Gln Gln Leu Met Asn Ile
225                 230                 235                 240

Glu Leu Ala Phe Glu Thr Ile Lys Gln Gln Leu Val Lys Lys Thr Asn
                245                 250                 255

Glu Glu Asp Ser Glu Gln Ser
            260

<210> SEQ ID NO 26
<211> LENGTH: 268
<212> TYPE: PRT
<213> ORGANISM: Aquilegia coerulea

<400> SEQUENCE: 26

Met Asn Glu Thr Asn Asp Val Phe Ser Ser Thr Pro Leu Asn Ile
1               5                   10                  15

Gly Ile Ile Gly Phe Gly Pro Phe Ala Gln Phe Leu Ala Lys Thr Met
            20                  25                  30

Ile Lys Gln Gly His Ile Leu Phe Ala Thr Ser Arg Ser Asp His Ser
        35                  40                  45

-continued

Gln Leu Cys Ser Gln Leu Gly Val Lys Phe Phe Lys Glu Met Asp Pro
            50                  55                  60

Phe Leu Asp Ser Asn Asn Tyr Asp Val Ile Leu Ile Ser Thr Ser Ile
 65                  70                  75                  80

Leu Ser Leu Ser Gln Val Leu Ser Ser Ile Pro Phe His Leu Leu Arg
                85                  90                  95

Gln Arg Thr Leu Phe Val Asp Val Leu Ser Val Lys Glu Tyr Pro Arg
            100                 105                 110

Gln Leu Leu Gln Val Leu Pro Glu Glu Thr Asp Val Leu Cys Thr
            115                 120                 125

His Pro Met Phe Gly Pro Glu Ser Gly Lys Asn Gly Trp Glu Gly Leu
            130                 135                 140

Ala Phe Met Tyr Glu Lys Val Arg Ile Arg Asn Glu Asp Thr Cys Ser
145                 150                 155                 160

Arg Phe Leu Gln Ile Phe Arg Ser Glu Gly Cys Arg Met Val Glu Met
                165                 170                 175

Pro Cys Glu Glu His Asp Arg Gln Ala Ala Arg Ser Gln Phe Leu Thr
            180                 185                 190

His Thr Ile Gly Arg Val Leu Ala Glu Met Asp Ile Lys Ser Thr Ser
            195                 200                 205

Met Asp Thr Lys Gly Phe Glu Thr Leu Val Tyr Leu Lys Asn Asp Thr
210                 215                 220

Ile Lys Asn Ser Phe Asp Leu Tyr Ser Gly Leu Phe Leu His Asn Arg
225                 230                 235                 240

Phe Ala Lys Gln Glu Leu Lys Asn Leu Glu Leu Ala Phe Glu Thr Val
                245                 250                 255

Lys Gln Asn Leu Leu Asn Lys Met Thr Glu Thr Ser
            260                 265

<210> SEQ ID NO 27
<211> LENGTH: 20
<212> TYPE: DNA
<213> ORGANISM: Artificial Sequence
<220> FEATURE:
<223> OTHER INFORMATION: Synthetic T7 promoter

<400> SEQUENCE: 27
taatacgact cactataggg                                          20

<210> SEQ ID NO 28
<211> LENGTH: 19
<212> TYPE: DNA
<213> ORGANISM: Artificial Sequence
<220> FEATURE:
<223> OTHER INFORMATION: Synthetic T7 terminator

<400> SEQUENCE: 28
ctagttattg ctcagcggt                                           19

<210> SEQ ID NO 29
<211> LENGTH: 35
<212> TYPE: DNA
<213> ORGANISM: Artificial Sequence
<220> FEATURE:
<223> OTHER INFORMATION: Synthetic primer: Glyma5g07870 - F

<400> SEQUENCE: 29
cgcgcggcag ccatatggcc atcgacgcgg cccag                         35

<210> SEQ ID NO 30
<211> LENGTH: 41
<212> TYPE: DNA
<213> ORGANISM: Artificial Sequence
<220> FEATURE:
<223> OTHER INFORMATION: Synthetic primer: Glyma5g07870 - R

<400> SEQUENCE: 30
gacggagctc gaattcttat ttatcttcag atatcttagg c        41

<210> SEQ ID NO 31
<211> LENGTH: 34
<212> TYPE: DNA
<213> ORGANISM: Artificial Sequence
<220> FEATURE:
<223> OTHER INFORMATION: Synthetic primer: Glyma11g35760 - F

<400> SEQUENCE: 31
cgcgcggcag ccatatgaca accatgtcaa cctc        34

<210> SEQ ID NO 32
<211> LENGTH: 35
<212> TYPE: DNA
<213> ORGANISM: Artificial Sequence
<220> FEATURE:
<223> OTHER INFORMATION: Synthetic primer: Glyma11g35760 - R

<400> SEQUENCE: 32
gacggagctc gaattcgcat caactttcgg ttctt        35

<210> SEQ ID NO 33
<211> LENGTH: 40
<212> TYPE: DNA
<213> ORGANISM: Artificial Sequence
<220> FEATURE:
<223> OTHER INFORMATION: Synthetic primer: Glyma14g05990 - F

<400> SEQUENCE: 33
gatctagact cgagggtacc tatgtcaaca tggtctctga        40

<210> SEQ ID NO 34
<211> LENGTH: 38
<212> TYPE: DNA
<213> ORGANISM: Artificial Sequence
<220> FEATURE:
<223> OTHER INFORMATION: Synthetic primer: Glyma14g05990 - R

<400> SEQUENCE: 34
ctagtgcatg cggccgcaca ttcagttttt tctagacc        38

<210> SEQ ID NO 35
<211> LENGTH: 32
<212> TYPE: DNA
<213> ORGANISM: Artificial Sequence
<220> FEATURE:
<223> OTHER INFORMATION: Synthetic primer: Glyma17g13150 - F

<400> SEQUENCE: 35
cgcgcggcag ccatatggcc ctccgtattc gc        32

<210> SEQ ID NO 36
<211> LENGTH: 36
<212> TYPE: DNA
<213> ORGANISM: Artificial Sequence
<220> FEATURE:
<223> OTHER INFORMATION: Synthetic primer: Glyma17g13150 - R

```
<400> SEQUENCE: 36
gacggagctc gaattcagtc cgtgtttgtt gaactg                                  36

<210> SEQ ID NO 37
<211> LENGTH: 31
<212> TYPE: DNA
<213> ORGANISM: Artificial Sequence
<220> FEATURE:
<223> OTHER INFORMATION: Synthetic primer: Glyma18g02650 - F

<400> SEQUENCE: 37
cgcgcggcag ccatatgtca acctcatcct c                                       31

<210> SEQ ID NO 38
<211> LENGTH: 35
<212> TYPE: DNA
<213> ORGANISM: Artificial Sequence
<220> FEATURE:
<223> OTHER INFORMATION: Synthetic primer: Glyma18g02650 - R

<400> SEQUENCE: 38
gacggagctc gaattcaata tgcatcaact ttcag                                   35

<210> SEQ ID NO 39
<211> LENGTH: 32
<212> TYPE: DNA
<213> ORGANISM: Artificial Sequence
<220> FEATURE:
<223> OTHER INFORMATION: Synthetic primer: Mt3g071980 - F

<400> SEQUENCE: 39
cgcgcggcag ccatatgtca tcatcttcca aa                                      32

<210> SEQ ID NO 40
<211> LENGTH: 35
<212> TYPE: DNA
<213> ORGANISM: Artificial Sequence
<220> FEATURE:
<223> OTHER INFORMATION: Synthetic primer: Mt3g071980 - R

<400> SEQUENCE: 40
gacggagctc gaattctcaa ctctcagttc tttct                                   35

<210> SEQ ID NO 41
<211> LENGTH: 35
<212> TYPE: DNA
<213> ORGANISM: Artificial Sequence
<220> FEATURE:
<223> OTHER INFORMATION: Synthetic primer: At1g15710 - F

<400> SEQUENCE: 41
cgcgcggcag ccatatggca atcgacgccg cccaa                                   35

<210> SEQ ID NO 42
<211> LENGTH: 39
<212> TYPE: DNA
<213> ORGANISM: Artificial Sequence
<220> FEATURE:
<223> OTHER INFORMATION: Synthetic primer: At1g15710 - R

<400> SEQUENCE: 42
gctcgaattc ggatccttaa gatgatgatg atgatgatg                               39

<210> SEQ ID NO 43
```

```
<211> LENGTH: 41
<212> TYPE: DNA
<213> ORGANISM: Artificial Sequence
<220> FEATURE:
<223> OTHER INFORMATION: Synthetic primer: Glyma 18g02650 - F

<400> SEQUENCE: 43
gatctagact cgagggtacc tatgtcaacc tcatcctctt c                    41

<210> SEQ ID NO 44
<211> LENGTH: 39
<212> TYPE: DNA
<213> ORGANISM: Artificial Sequence
<220> FEATURE:
<223> OTHER INFORMATION: Synthetic primer: Glyma18g02650 - R

<400> SEQUENCE: 44
ctagtgcatg cggccgcact ttcagttctt ttatgaccc                      39

<210> SEQ ID NO 45
<211> LENGTH: 41
<212> TYPE: DNA
<213> ORGANISM: Artificial Sequence
<220> FEATURE:
<223> OTHER INFORMATION: Synthetic primer: Mt3g071980 - F

<400> SEQUENCE: 45
gatctagact cgagggtacc tatgtcatca tcttccaaaa g                   41

<210> SEQ ID NO 46
<211> LENGTH: 37
<212> TYPE: DNA
<213> ORGANISM: Artificial Sequence
<220> FEATURE:
<223> OTHER INFORMATION: Synthetic primer: Mt3g071980 - R

<400> SEQUENCE: 46
ctagtgcatg cggccgcact ctcagttctt tctgggt                         37

<210> SEQ ID NO 47
<211> LENGTH: 40
<212> TYPE: DNA
<213> ORGANISM: Artificial Sequence
<220> FEATURE:
<223> OTHER INFORMATION: Synthetic primer: At 1g 15710 - F

<400> SEQUENCE: 47
gatctagact cgagggtacc aatgctactc catttctctc                      40

<210> SEQ ID NO 48
<211> LENGTH: 38
<212> TYPE: DNA
<213> ORGANISM: Artificial Sequence
<220> FEATURE:
<223> OTHER INFORMATION: Synthetic primer: At 1g15710 - R

<400> SEQUENCE: 48
ctagtgcatg cggccgcaga tgatgatgat gatgatga                        38

<210> SEQ ID NO 49
<211> LENGTH: 20
<212> TYPE: DNA
<213> ORGANISM: Artificial Sequence
<220> FEATURE:
<223> OTHER INFORMATION: Synthetic primer: Glyma5g07870 - F

<400> SEQUENCE: 49
```

-continued cgaccacgat aagttcgctg                                               20

<210> SEQ ID NO 50
<211> LENGTH: 23
<212> TYPE: DNA
<213> ORGANISM: Artificial Sequence
<220> FEATURE:
<223> OTHER INFORMATION: Synthetic primer: Glyma5g07870 - R

<400> SEQUENCE: 50
cttggttttg tcatcagact ggt                                           23

<210> SEQ ID NO 51
<211> LENGTH: 20
<212> TYPE: DNA
<213> ORGANISM: Artificial Sequence
<220> FEATURE:
<223> OTHER INFORMATION: Synthetic primer: Glyma11g35760 - F

<400> SEQUENCE: 51
gcattgttgg attcggcaac                                               20

<210> SEQ ID NO 52
<211> LENGTH: 20
<212> TYPE: DNA
<213> ORGANISM: Artificial Sequence
<220> FEATURE:
<223> OTHER INFORMATION: Synthetic primer: Glyma11g35760 - R

<400> SEQUENCE: 52
ttttatgacc ctgctcccca                                               20

<210> SEQ ID NO 53
<211> LENGTH: 20
<212> TYPE: DNA
<213> ORGANISM: Artificial Sequence
<220> FEATURE:
<223> OTHER INFORMATION: Synthetic primer: Glyma13g01050 - F

<400> SEQUENCE: 53
gaacgccccg aagtcatttt                                               20

<210> SEQ ID NO 54
<211> LENGTH: 20
<212> TYPE: DNA
<213> ORGANISM: Artificial Sequence
<220> FEATURE:
<223> OTHER INFORMATION: Synthetic primer: Glyma13g01050 - R

<400> SEQUENCE: 54
ccactccacc catcttttgc                                               20

<210> SEQ ID NO 55
<211> LENGTH: 20
<212> TYPE: DNA
<213> ORGANISM: Artificial Sequence
<220> FEATURE:
<223> OTHER INFORMATION: Synthetic primer: Glyma14g05990 - F

<400> SEQUENCE: 55
attggcgtag ttgggtttgg                                               20

<210> SEQ ID NO 56
<211> LENGTH: 20
<212> TYPE: DNA

<213> ORGANISM: Artificial Sequence
<220> FEATURE:
<223> OTHER INFORMATION: Synthetic primer: Glyma14g05990 - R

<400> SEQUENCE: 56
agatcttgcc acccatcctt                                              20

<210> SEQ ID NO 57
<211> LENGTH: 26
<212> TYPE: DNA
<213> ORGANISM: Artificial Sequence
<220> FEATURE:
<223> OTHER INFORMATION: Synthetic primer: Glyma14g 15060 - F

<400> SEQUENCE: 57
caaataccat ctcttcttac aaaccc                                       26

<210> SEQ ID NO 58
<211> LENGTH: 20
<212> TYPE: DNA
<213> ORGANISM: Artificial Sequence
<220> FEATURE:
<223> OTHER INFORMATION: Synthetic primer: Glyma14g 1 5060 - R

<400> SEQUENCE: 58
tcaccggaac ttatcgtggc                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic primer: Glyma17g13150 - F

<400> SEQUENCE: 59
cctcggaatt ttcgccagag                                              20

<210> SEQ ID NO 60
<211> LENGTH: 22
<212> TYPE: DNA
<213> ORGANISM: Artificial Sequence
<220> FEATURE:
<223> OTHER INFORMATION: Synthetic primer: Glyma17g13150 - R

<400> SEQUENCE: 60
aagaaactga ccaaagttgc ca                                           22

<210> SEQ ID NO 61
<211> LENGTH: 20
<212> TYPE: DNA
<213> ORGANISM: Artificial Sequence
<220> FEATURE:
<223> OTHER INFORMATION: Synthetic primer: Glyma18g18050 - F

<400> SEQUENCE: 61
aggacgggaa caaggtgaag                                              20

<210> SEQ ID NO 62
<211> LENGTH: 18
<212> TYPE: DNA
<213> ORGANISM: Artificial Sequence
<220> FEATURE:

```
<223> OTHER INFORMATION: Synthetic primer: Glyma18g18050 - R

<400> SEQUENCE: 62
gcaaatcagg ctctctcg                                                    18
```

US 9,701,977 B2

PREPHENATE DEHYDROGENASES AND AROGENATE DEHYDROGENASES THAT ARE INSENSITIVE TO EFFECTOR FEEDBACK INHIBITION AND METHODS OF USING THE SAME

CROSS-REFERENCE TO RELATED APPLICATIONS

This patent application claims the benefit of priority of U.S. Provisional Patent Application No. 61/906,252, filed Nov. 19, 2013 and of U.S. Provisional Patent Application No. 62/058,457, filed Oct. 1, 2014, which is incorporated herein by reference in its entirety.

SEQUENCE LISTING

This application is being filed electronically via EFS-Web and includes an electronically submitted Sequence Listing in .txt format. The .txt file contains a sequence Listing entitled "2014-11-19_5671-00054_ST25.txt" created on Nov. 19, 2014 and is 66,676 bytes in size. The Sequence Listing contained in this .txt file is part of the specification and is hereby incorporated by reference herein in its entirety.

INTRODUCTION

Polynucleotides and polypeptides encoding prephenate dehydrogenases and arogenate dehydrogenases which are insensitive to feedback inhibition by tyrosine and other downstream products and methods of using the same are provided herein.

Tyrosine (Tyr) is an aromatic amino acid required for protein biosynthesis in all living cells. Because animals lack the aromatic amino pathways, Tyr is an essential nutrient in animal diets. In plants, Tyr and the Tyr pathway intermediate, 4-hydroxyphenylpyruvate (HPP), also serve as precursors of numerous important plant natural products. These compounds include the photosynthetic electron carrier, plastoquinone, antioxidant tocopherols (vitamin E), betalains and various defense compounds (e.g., isoquinoline alkaloids and cyanogenic glycoside), many of which have important nutritional and pharmacological activities in humans. The head group of plastoquinone is derived from HPP and plays an essential role as an electron carrier of the photosynthetic electron transport chain. Inhibition of plastoquinone biosynthesis at the biochemical reaction catalyzed by HPP dioxygenase (HPPD, FIG. 1) leads to bleaching and lethal phenotypes in plants. Thus, some of the widely used herbicides (e.g., isoxaflutole, sulcotrione) specifically inhibit the HPPD enzyme.

Detection of Tyr ammonia-lyase activity and labeling experiments also suggest that Tyr can be a precursor of lignin and other phenylpropanoid compounds in some plant species. Many of the Tyr pathway-derived plant-specialized metabolites have been co-opted by humans to serve nutritional and medicinal roles, such as lipid-soluble antioxidants, tocochromanols (vitamin E), and narcotic analgesics such morphine and codeine. Despite their importance in both plant and human physiology and metabolism, the biosynthetic pathways for Tyr and HPP remain elusive in plants.

SUMMARY

Polynucleotides and polypeptides encoding prephenate dehydrogenases and arogenate dehydrogenases which are insensitive to feedback inhibition by products of the tyrosine pathway are provided herein. In particular, the polypeptides are insensitive to feedback inhibition by at least one of tyrosine, tryptophan, phenylalanine and 4-hydroxyphenylpyruvate (HPP). The polypeptides include SEQ ID NOs: 2, 4, 6, 8, and 13-26 and polypeptides having at least 80, 85, 90, 95, 98 and 99% identity to these polypeptides.

The polynucleotides encoding the polypeptides provided herein may be used in constructs, such as expression constructs. The constructs may include a promoter operably connected to the polynucleotides to allow for the expression of the polynucleotides and production of the polypeptides provided herein in a cell or plant.

In another aspect, transgenic cells comprising the constructs or the polynucleotides encoding the polypeptides are provided herein. The transgenic cells may be plant cells and may be part of a transgenic plant. Seeds, parts, progeny and asexual propagates of the transgenic plants are also provided. The transgenic cells and plants or plant parts from these plants express higher levels of at least one of the polynucleotides or polypeptides provided herein as compared to a control.

In yet another aspect, methods of increasing resistance of a plant to an herbicide by increasing expression of, altering the expression pattern of or increasing the copy number of the polynucleotides encoding prephenate dehydrogenase or arogenate dehydrogenase or homologs, functional variants or combinations thereof in cells of the plant are provided. The increased expression of the polynucleotide in cells of the plant increases the resistance of the plant to the herbicide as compared to a control plant.

In a further aspect, methods of increasing production of at least one product of the tyrosine or HPP pathway in a plant by increasing expression of a polynucleotide encoding a prephenate dehydrogenase, an arogenate dehydrogenase or homologs, functional variants or combinations thereof in cells of the plant are provided. The increased expression of the polynucleotide in cells of the plant increases the production of at least one product of the tyrosine and HPP pathways.

BRIEF DESCRIPTION OF THE DRAWINGS

FIG. 2 is a set of graphs showing HPLC detection of PDH activity from plant tissues. FIG. 2A shows HPLC detection of HPP, HPLA and HPP after reduction to HPLA. A gray solid line represents an authentic standard of HPLA. The retention time of HPP reduced to HPLA is shown by a gray dotted line. FIG. 2B shows HPLC detection of PDH activity from legumes. PDH assays using leaf enzyme extracts from soybean, *Medicago* and *Arabidopsis* (solid lines) were compared with their respective boiled extract control (hashed lines). FIG. 2C shows quantification of PDH (black) and ADH (white) activity based on HPLC data (FIG. 2B and FIG. 6). ADH and PDH activity from leaf tissues are expressed in pKat mg protein$^{-1}$±s.e.m. (pmol sec$^{-1}$ mg protein$^{-1}$) of three biological replicates, whereas those from root, green pod and flower tissues were from a single experiment. N.D., below detection limit.

FIG. 3 is a set of figures showing the phylogeny and enzymatic activity of candidate legume PDHs. FIG. 3A shows the maximum likelihood phylogeny of soybean candidates together with ADHs and PDHs from plants. Two distinct eudicot clades are shaded in green and blue, with the former containing canonical plant ADH sequences (for example, *Arabidopsis* AtADH1 and AtADH2). ADH homologs from green algae were used as an outgroup. AtADH1 and AtADH2, *Arabidopsis thaliana* ADH1 and ADH2; Bdistachyon, *Brachypodium distachyon*; Celemintina, *Citrus clementina*; Creinhardtii, *Chlamydomonas reinhardtii*; Fvesca, *Fragaria vesca*; Glyma, *Glycine max*; Mt, *Medicago truncatula*, Olucimarinus, *Ostreococcus lacimarinus*; Ptrichocarpa, *Populus trichocarpa*; Sbicolor, *Sorghum bicolor*; Slycopersicum, *Solanum lycopersicum*. Gene numbers following names are based on those listed at http://www.phytozome.net/, except for *Arabidopsis* GI numbers shown in parentheses. Stars denote enzymes exhibiting PDH activity (based on the data in FIG. 3B and FIG. 3C). Extended phylogenetic analyses are presented in FIG. 9. FIG. 3B and FIG. 3C are a set of graphs showing qualitative detection of ADH (left; FIG. 3B) and PDH (right; FIG. 3C) activity from legume enzymes. *E. coli* cell lysates were incubated with 2 mM substrate (L-arogenate or prephenate) and 1 mM NPDH$^+$. PDH activity detected in Glyma18g02650, Glyma11g35760 and Mt3g071980 are marked with stars. The dotted lines indicate retention times of Tyr or HPLA peaks.

FIG. 4 is a set of figures showing, the localization of legume PDH enzymes, and PDH and CM activity. FIG. 4A-D is a set of photographs showing subcellular localization of GFP-fused legume PDHs. GFP was fused at the C-terminal of GmPDH1 (FIG. 4A) and MtPDH1 (FIG. 4B) and transiently expressed in *Arabidopsis* protoplasts. GFP-fused AtADH2 (FIG. 4C) and free GFP (FIG. 4D) were used as controls for plastidic and cytosolic localization, respectively. Representative images show GFP fluorescence and chlorophyll autofluorescence in green and purple, respectively. Scale bars, 10 μm. FIG. 4E-H is a set of graphs showing the subcellular localization of PDH (FIG. 4E) and ADH (FIG. 4F) activity in soybean tissue. Cytosolic and plastidic fractions were prepared from 4-week-old soybean leaf tissue. PEP carboxylase (FIG. 4G) and PPA-AT (FIG. 4H) were used as cytosolic and plastidic marker enzymes, respectively. Data show mean±s.e.m. of three independent experiments. N.D., below detection limit. FIG. 4I is a graph showing the subcellular localization of CM activity. CM activity was analyzed in crude soybean leaf extracts as well as cytosolic and plastidic fractions. Activity was tested with and without the addition of 1 mM L-Tyr (light gay) and 1 mM L-Trp (dark gray). CM activity is expressed as the mean of three independent experiments±s.e.m. in pKat mg protein$^{-1}$. N.D., below detection limit.

FIG. 5 is a set of figures showing the Tyr insensitivity of PDHs and proposed alternative Tyr biosynthetic routes in legumes. FIG. 5A is a graph showing L-Tyr sensitivity of PDH and ADH enzymes and activity. PDH or ADH activity was measured using increasing L-Tyr concentrations from purified recombinant enzymes, crude *E. coli* extract expressing Glyma11g35760 and crude soybean leaf extract. Data show mean±s.e.m. of three independent experiments (as summarized in Table 4) and are expressed as the percentage of respective control activity without L-Tyr (0 mM). Significant differences from the corresponding no L-Tyr control are indicated; *P≤0.05, **P≤0.01. N.D., below detection limit. FIG. 5B and FIG. 5C are a set of graphs showing PDH activity of GmPDH1 (FIG. 5B) and MtPDH1 (FIG. 5C) recombinant enzymes measured in the presence (open) or absence (filled) of L-Tyr (1 mM) with decreasing prephenate concentrations (15 mM to 59 μM). Assays were incubated at 37° C. for 15 min with 1 mM NADP+. The production of reduced cofactor (NADPH) was measured at 340 nm using a spectrophotometer. The presence of 1 mM L-Tyr had no effect on PDH activity of both GmPDH1 and MtPDH1 even under non-saturating substrate concentrations. FIG. 5D shows a revised model of the Tyr pathways in legumes having both plastidic ADH and cytosolic PDH routes. Activation and inhibition are indicated by dotted lines with an arrow and hashes, respectively. The gray box represents plastid envelopes. Only the predominant plant Phe pathway is shown. Abbreviations are indicated in FIG. 1, except for ADT, arogenate dehydratase.

FIG. 7 is a set of graphs showing the gene expression of soybean candidate genes in various tissues. Gene expression of the twelve PDH candidates from soybean were analyzed from diverse tissue types using two independent publically-available expression databases, soybase.org (FIG. 7A) and soybean eFPBrowser (FIG. 7B). Only five genes (Glyma05g07870, Glyma11g35760, Glyma14g05990, Glyma17g13150 and Glyma18g02650, indicated in blue letters) showed constitutive expression in all tissues, in which PDH activity was detected (FIG. 2C). One gene (Glyma14g15060) also showed expression in both databases but only in flower tissues. The three candidate genes lacking the NAD(P)+ binding domain (Glyma02g42870, Glyma04g13090, and Glyma17g11700, indicated in red letters) as well as the remaining three (Glyma13g01050, Glyma13g06340, and Glyma14g15010) showed no or inconsistent expression in these data sets.

FIG. 8 is a set of photographs and schematic drawings showing the RT-PCR analysis of six candidates in various soybean tissue types. To validate gene expression data gathered from two databases (FIG. 7), RT-PCR was performed using cDNA generated from various soybean tissues leaf, flower, root, and seed pod) where PDH activity was detected (FIG. 2C). All gene specific primers produced PCR amplicons of the expected size from genomic DNA (indicated in blue). FIG. 8A is a photograph showing expression of a housekeeping gene (Glyma18g18050, eukaryotic translation initiation factor 3 subunit G, eIF) was detected from all four cDNAs. FIG. 8B-F are photographs showing the PCR products (indicated by red asterisks) of the expected size were also produced from all cDNAs for five genes, Glyma05g07870, Glyma17g13150, Glyma14g05990, Glyma18g02650 and Glyma11g35760, respectively. FIG. 8G is a photograph showing the other candidate, Glyma14g15060, which showed some expression signals in flower (FIG. 7), did not produce any amplicons from any cDNAs. Corresponding gene-specific primers (Table 2) are indicated by the arrows above each gene diagram; the blue and red bars indicate the predicted genomic DNA and cDNA amplicons, respectively. The black boxes and lines denote exons and introns, respectively, according to phytozome.net. The white asterisks on the gels indicate the 1 kb marker.

FIG. 11 is a set of graphs and photographs showing substrate and electron acceptor preference of GmPDH1 and MtPDH1. Assays were conducted using varying enzyme concentrations of purified GmPDH1 (FIG. 11A) and MtPDH1 (FIG. 11B), with prephenate (circles) or L-arogenate (squares) as a substrate (1.5 mM) and NADP+ (filled) or NAD+ (open) as a cofactor (1 mM). Reactions were incubated at 37° C. for 15 min and the production of reduced cofactor. NAD(P)H, was measured at 340 am using a spectrophotometer. The slope of the lines represents the specific, activity for GmPDH1 and MtPDH1 under different reaction conditions. FIG. 11C and FIG. 11D are photographs of SDS-PAGE gels of the *E. coli* cell lysates (lane 1) and the purified, recombinant enzymes (lane 2) of GmPDH1 (FIG. 11C) and MtPDH1 (FIG. 11D).

FIG. 12 is a set of graphs showing the effects of Phe, Trp, and HPP on GmPDH1 and MtPDH1 activity. Sensitivity of GmPDH1 (black) and MtPDH1 (gray) purified recombinant enzymes was tested with the two other aromatic amino acids, L-Phe (FIG. 12A) and L-Trp (FIG. 12B), as well as the immediate product of the PDH reaction, HPP (FIG. 12C). Data are means±SE of three independent experiments and expressed as the percent of control activity without respective effector (0 mM). Significant differences from the corresponding, no effector control are labeled (*P≤0.05). None of the tested molecules significantly reduced PDH activity of GmPDH1 or MtPDH1.

DETAILED DESCRIPTION

Figure 1:
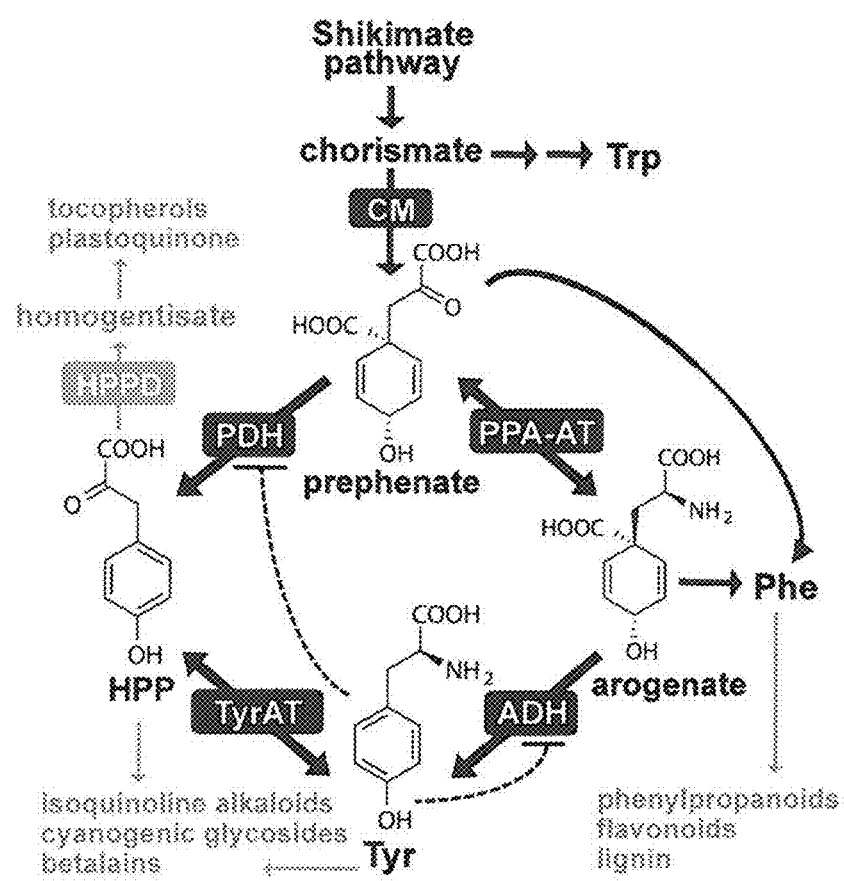
FIG. 1 is a diagram of the proposed pathways for tyrosine and 4-hydroxyphenylpyruvate biosynthesis and metabolism in plants. Tyrosine (Tyr) is synthesized from chorismate, the final product of the shikimate pathway, via either arogenate or 4-hydroxyphenylpyruvate (HPP). In plants, Tyr is further converted to a variety of natural products, such as pigments, vitamins, and alkaloids. Plant-specialized metabolism downstream of HPP, Tyr and Phe is indicated in gray. Black dotted lines denote potential feedback regulation by Tyr. ADH, arogenate dehydrogenase; CM, chorismate mutase; HPP-AT, HPP aminotransferase; HPPD, HPP dioxygenase PDH, prephenate dehydrogenase; PPA-AT, prephenate aminotransferase; Phe, phenylalanine; Trp, tryptophan.

Tyr is synthesized from the final product of the shikimate pathway, chorismate, which is converted into prephenate by chorismate mutase (CM; Enzyme Commission (EC) 5.4.99.5; FIG. 1). In enteric bacteria, where the pathway was first and extensively studied (for example, *Escherichia coli*), prephenate is first converted by prephenate dehydrogenase (TyrA$_p$ referred to as PDH hereafter; EC 1.3.1.13) to HPP, which is then transaminated to Tyr (the PDH pathway). In plants, prior biochemical evidence indicates that Tyr is synthesized in the plastids via the arogenate dehydrogenase (TyrA$_a$ referred to as ADH hereafter; EC 1.3.1.78) pathway, in which prephenate is first converted to arogenate by prephenate aminotransferase (PPA-AT; EC 2.6.1.7) and then to Tyr by ADH (See FIG. 1).

ADH and PDH enzymes, both belonging to the TyrA protein family, are located at the branch points between Phe and Tyr biosynthesis. They are generally inhibited by L-Tyr, making them key enzymes in regulating carbon flux into Tyr (FIG. 1). ADH activity has been detected in a broad range of plant species, all of which use NADP$^+$ as a cofactor except *Zea mays*, whose root ADH activity uses NAD$^+$, like most Microbial PDHs. To date, only two ADH genes have been identified (AtADH1 and AtADH2 in *Arabidopsis thaliana*), and their corresponding enzymes have been biochemically characterized in vivo. The encoded AtADH enzymes use NADP$^+$, localize to the plastids and are strongly inhibited by L-Tyr. Recombinant AtADH1 enzyme only accepts L-arogenate as a substrate, whereas AtADH2 also exhibits very weak PDH activity and strong ADH activity.

In contrast, PDH activity has only been detected in some legume species. See Seihl, in *Plant Amino Acids: Biochemistry and Biotechnology* (ed. Singh, B.) 171-204 (CRC Press, New York, 1999) and Rubin and Jensen, Plant Physiol 64:727-734 (1979) and Table 1. PDH activity partially purified from mung bean seedlings uses NADP but not NAD$^+$ cofactor, has similar K$_m$ values for prephenate and L-arogenate and has 2.9-fold higher PDH-specific than ADH-specific activity. These biochemical studies suggest that legumes can potentially use both the PDH and ADH pathways, though most plants synthesize Tyr via the ADH pathway. However, the molecular identity of plant PDH activity was unknown before the present invention.

Several of these sequences have already been demonstrated to encode enzymes that are also insensitive to product feedback inhibition.

TABLE 1

SUMMARY OF PDH AND ADH ACTIVITIES DETECTED IN PLANTS

| Species | Family | ADH activity | PDH activity | Cofactor | Reference |
|---|---|---|---|---|---|
| *Glycine max* (soybean) | Leguminosae | + | + | NAD(P)$^+$ | this study[1,2] |
| *Medicago truncatala* | Leguminosae | + | + | NAD(P)$^+$ | this study[1,3-5] |
| *Vigna radiata* (mung bean) | Leguminosae | + | + | NADP$^+$ | |
| *Phaseolus vulgaris* (bush bean) | Leguminosae | NT | + | NADP$^+$ | 4 |
| *Phaseolus coccineus* (runner bean) | Leguminosae | NT | + | NADP$^+$ | 4 |
| *Vicia faba* (broad bean) | Leguminosae | NT | + | NADP$^+$ | 4 |
| *Cassia obtusifolia* (sicklepod) | Leguminosae | + | + | NADP$^+$ | 3 |
| *Medicago sativa* (alfalfa) | Leguminosae | + | + | NADP$^+$ | 3 |
| *Sorghum bicolor* | Poaceae | + | − | NADP$^+$ | 6 |
| *Zea mays* (corn) | Poaceae | + | − | NAP$^+$ | 7 |
| *Arabidopsis thaliana* | Brassicaceae | + | − | NADP$^+$ | this study[a] |
| *Armoracia rusncana* (horseradish) | Brassicaceae | NT | − | NA | 2 |
| *Solanum tuberosum* | Solanaceae | NT | − | NA | 2 |
| *Nicotiana sylvestis* | Solanaceae | + | − | NADP$^+$ | 8 |
| *Rosa* sp. var. *scepter* | Rosaceae | NT | − | NA | 2 |
| *Pagopyrum esculentum* (buckwheat) | Polygonaceae | NT | − | NA | 2 |
| *Reseda luteola* | Resedaceae | NT | − | NA | 2 |

+: activity detected
−: activity not detected
NT: not tested
NA: not applicable
[a]PDH activity detected in AtADH2[9] but not AtADH1[10] purified enzyme, However, using HPLC-based PDH assay detection methods (see results), no PDH activity was detected in *Arabidopsis* crude leaf extracts.

Gene(s) responsible for the PDH activity uniquely present in legume were identified by searching the genomic sequence of *Glycine max* var. Williams 82 for genes with significant similarity to the *Arabidopsis* ADHs and microbial PDHs. Out of twelve potential soybean ADH/PDH candidates, a careful selection of candidate genes by expression and biochemical studies discovered two PDH genes and corresponding enzymes having strong preference toward prephenate over arogenate and, to our surprise and unlike other plant ADHs, the enzymes were completely insensitive to Tyr. The polypeptide sequences are provided as SEQ ID NO: 2 and 4. An ADH gene and enzyme were also identified and is provided as SEQ ID NO: 6. Subsequently, we also found that the PDH activity in soybean leaf and root tissue was not inhibited by Tyr. A related PDH gene was identified in *Medicago truncatula* and it was also found to be insensitive to Tyr feedback inhibition (See SEQ ID NO 8).

Related PDH and ADH genes with high sequence similarity were also identified using phylogenetic analyses. The sequences of these related polypeptides are provided in SEQ ID NOs: 13-26. These sequences share at least 65% amino acid sequence identity with the Glyma18g02650 polypeptide. For example, Mtruncatula3g071980 shares 86% identity with Glyma18g02650 and Mtruncatula5g083530.2 shares 68% identity with Glyma18g02650, Mtruncatula1a012047 and Celementina 1003237 share 75% identity with Glyma18g02650 and StuberosumPGSC0003DMG400023957 shares 76% identity with Glyma18g02650.

The polynucleotides and/or polypeptides described and used herein may encode the full-length or a functional fragment of Glyma18g02650, Glyma11g35760, Glyma14g05990, and/or Mtruncatula3g071980 (PDH1, PDH2, ADH1 and MtPDH1, respectively). Naturally occurring or engineered variants of Glyma18g02650, Glyma11g35760, Glyma14g05990, and/or Mtruncatula3g071980 or the homologs identified from other species of SEQ ID NOs: 13-26 are also encompassed. Polynucleotides or polypeptides derived from those of SEQ ID NOs: 3-26 are also encompassed and all or part of these may be based upon nucleotide or amino acid combinations similar to all or portions of Glyma18g02650, Glyma11g35760, Glyma14g05990 and/or Mtruncatula3g071980 or their encoded products. The polypeptide may be at least 65%, 70%, 75%, 80%, 85%, 90%, 95%, 97%, 98%, 99% or 100% identical to the sequences provided herein. The polynucleotides encoding the polypeptides may be at least 50%, 60%, 65%, 70%, 75%, 80%, 85%, 90%, 95% or 100% identical to the sequences available in the public soybean genetic sequence database and provided herein.

Additional polynucleotides encoding additional polypeptides may also be included in the constructs provided herein. The additional polypeptides may include polypeptides whose expression in combination with the PDH or ADH polypeptides provided herein provide for increased expression of a product of the tyrosine or HPP pathway such as vitamin E or increased resistance to an herbicide. Constructs including the polynucleotides and polypeptides provided herein may also include promoters or enhancers to promote transcription of the polynucleotides and expression of the polypeptides or polypeptides that label the polypeptides such as a fluorescent marker (i.e., GFP) or a marker that can be used to purify the polypeptides such as a his tag.

The polynucleotide sequences for Glyma18g02650, Glyma11g35760, Glyma14g05990 and Mtruncatula3g07980 are provided as SEQ ID NO: 1, SEQ ID NO: 3, SEQ ID NO: 5 and SEQ ID NO: 7, respectively. The polynucleotide sequences provided are the cDNA sequences. The corresponding genomic sequences are available publicly in the soybean or *Medicago* genomic databases. The polypeptide sequences for Glyma18g02650, Glyma11g35760, Glyma14g05990 and Mtruncatula3g071980 are provided as SEQ ID NO: 2, SEQ ID NO: 4, SEQ ID NO: 6 and SEQ ID NO: 8, respectively. Histidine tags were added to the polypeptides and these sequences are provided as SEQ ID NO: 9, SEQ ID NO: 10, SEQ ID NO: 11 and SEQ ID NO: 12, respectively. The polypeptides of SEQ ID NO: 2, SEQ ID NO: 4 and SEQ ID NO: 8 (and SEQ ID NO: 9, 10 and 12) encode proteins having predominately prephenate dehydrogenase activity. The polypeptide of SEQ ID NO: 6 and SEQ ID NO: 11 encode proteins having predominately arogenate dehydrogenase activity. Further homologs to these enzymes are provided as SEQ ID NOs: 13-26 and include both ADH and PDH enzymes. These enzymes are expected to lack tyrosine feedback inhibition as well based on sequence homology and phylogenetic analyses. We are in the process of cloning and testing each of these enzymes to confirm the sequence and phylogenetic analyses but those tested to date have the expected enzyme activity and are insensitive to feedback inhibition by tyrosine.

The polypeptides provided herein are insensitive to feedback inhibition by products of the tyrosine pathway. In particular, the polypeptides are insensitive to at least one of tyrosine, tryptophan, phenylalanine or 4-hydroxyphenylpyruvate. The polypeptides may be insensitive to all of the products of the pathway. The lack of sensitivity to feedback inhibition by the products produced by the enzyme activity may allow for increased production of downstream products of these pathways. For example, cells expressing a polypeptide provided herein may have increased levels of vitamin E, plastoquinone, cyanogenic glycosides, isoquinoline alkaloids, rosmarinic acid, betalains, suberins, lignins, flavonoids, tannin, tyrosine or other products of these pathways.

The expression of the polypeptides encoded by Glyma18g02650, Glyma11g35760, Glyma14g05990, Mtruncatula3g071980 and/or SEQ ID NOs: 2, 4, 6, 8, or 13-26 may be increased in cells or plants using recombinant biology techniques available to those of skill in the art. For example, the polynucleotides encoding the polypeptides of SEQ ID NO: 2, 4, 6, 8, or 13-26 may be included in a construct carried by transformed cells or alternatively a plant may be transgenic for the polynucleotides. Suitably the level of polypeptide is increased at least 1.2, 1.5, 1.7, 2, 3, 4, 5, 7, 10, 15, 20 or 25 fold in comparison to the untreated or other control plants or plant cells. Control cells or control plants are comparable plants or cells in which Glyma18g02650, Glyma11g35760, Glyma14g05990, Mtruncatula3g071980 and/or SEQ ID NOs: 2, 4, 6, 8, 13-26 expression has not been increased, such as a plant of the same genotype transfected with empty vector or plant transgenic for a distinct polynucleotide. The cells or plants may be soybean plants, but the polynucleotides and polypeptides may also be expressed in cells or plants other than soybean. For instance the polypeptides may be expressed in other legumes or cereal plants, including but not limited to along bean, rice, wheat, corn, barley, millet, oat, rye, or rapeseed. The polypeptides may also be expressed in other plants such as beets to increase production of betalains. These may be transgenic plants engineered to produce at least one of the polypeptides provided herein.

Also encompassed are seeds, cells, or other plant parts capable of expressing at least one of Glyma18g02650, Glyma11g35760, Glyma14g05990, Mtruncatula3g071980 or SEQ ID NOs: 2, 4, 6, 8, or 13-26 in increased amounts or non-natively. Plants grown from the seeds, cells or as asexually reproduced progeny of the plants are also encompassed. Methods for generating transgenic plants are well known in the art. The transgenic cells or plants express higher levels of the polynucleotides provided herein including at least one of Glyma18g02650. Glyma11g105760, Glyma14g05990. Mtruncatula3g071980, and/or the polypeptides encoded by the polynucleotides including SEQ ID NOs: 2, 4, 6, 8, or 13-26.

The expression levels are increased as compared to the levels in a non-transgenic or transgenic control plant. The expression of the polynucleotides or polypeptides may be increased in a single tissue within the plant, such as within the leaves, roots, flowers or seeds or may be increased throughout the plant. The expression may be regulated by the design of the construct used to produce the transgenic cell or plant such as the selection of promoter. For example, constitutive or inducible promoters may be used to drive expression of the polypeptides in the cells or transgenic plants or plant parts. Those of skill in the art are capable of choosing appropriate promoters and designing constructs for expression of polynucleotides. The expression of the polypeptide and the polynucleotides encoding the polypeptides in the transgenic plant is altered relative to the level of expression of the native polypeptides in a control plant, e.g., a control soybean plant.

In still other embodiments the polypeptides may be expressed in bacterial or fungal cells. As shown in the Examples at least PDH1 (Glyma18g02650) can use NAD$^+$ as an electron acceptor and thus this enzyme may be functional in bacterial cells as well as plant cells.

Also provided herein are constructs including a promoter operably linked to a Glyma18g02650, Glyma11g35760, Glyma14g05990, Mtruncatula3g071980 and/or a related polynucleotide encoding, a polypeptide comprising SEQ ID NOs: 2, 4, 6, 8, 13-26 or a fragment or functional variant thereof. Also included are homologs or variants of these sequences from other soybean varieties or other legumes. The constructs may be introduced into plants to make transgenic plants or may be introduced into plants, or portions of plants, such as plant tissue, plant calli, plant roots or plant cells. Suitably the promoter is a plant promoter, suitably the promoter is operational in leaf cells, seed, root or fruit cells or other tissues of the plant. The promoter may be tissue specific, inducible, constitutive, or developmentally regulated. The constructs may be an expression vector or a targeting vector for incorporation of the construct or a portion thereof into the cell. Constructs may be used to generate transgenic plants or transgenic cells. The polypeptide may be at least 80%, 85%, 90%, 95%, 97%, 98%, 99% or 100% identical to the sequences of SEQ ID NOs: 2, 4, 6, 8, or 13-26. The constructs may comprise more than one polynucleotide and may mediate expression of one or more polypeptides or may comprise only one, two, three or more of the polynucleotides encoding the polypeptides provided herein or other polypeptides of interest.

Transgenic plants including a non-native or exogenous polynucleotide encoding at least one of the three PDH and/or ADH polypeptides identified and described herein are also provided. Suitably the transgenic plants are legumes, suitably soybeans. The soybean and *Medicago* polynucleotides and polypeptides identified herein are PDH and ADH enzymes that are not feedback inhibited. These enzymes may also be used to generate transgenic plants other than soybeans capable of expressing the genes described herein. For example the plants may be other legumes or cereal crop plants. Alternatively, homologous genes or polypeptides from these plants may be identified by comparison to the genes and polypeptides identified herein and these genes may be used to generate transgenic plants. For example, SEQ ID NOs: 13-26 may be used to generate transgenic plants. The transgenic plants express increased levels of at least one of Glyma18g02650, Glyma11g35760, Glyma14g05990, Mtruncatula3g071980 and/or a polypeptide of SEQ ID NOs: 13-26 as compared to a control non-transgenic plant from the same line, variety or cultivar or a transgenic control expressing a polypeptide other than Glyma18g02650, Glyma11g35760, Glyma14g405990, Mtruncatula3g071980 and/or the polypeptides of SEQ ID NOs: 13-26.

Product based feedback inhibition of the ADH and PDH enzymes limits production of useful downstream natural products in plants. The PDH and ADH enzymes provided herein are insensitive to product feedback inhibition and thus may be useful to increase production of downstream natural products. Many of these downstream products are useful or have useful applications such that expression of the enzymes that are not feedback inhibited in plants or plant cells results in overproduction of these natural products. Non-limiting examples of downstream products of these pathways whose production may be increased by overexpression or transgenic expression of the polypeptides provided herein include vitamin E, plastoquinone, cyanogenic glycosides, isoquinoline alkaloids, rosmarinic acid, betalains, suberins, lignins, flavonoids, tannin, tyrosine or other products of these pathways.

Isoquinoline alkaloids are a large and diverse group of alkaloids with thousands of structures and a wide variety of biological activities. Morphine and codeine are narcotic analgesics, berberine and sanguinarine are used as antibiotics and noscapine may be useful for suppressing prostate cancer. These alkaloids are made via a complex pathway involving many enzymatic steps, but tyrosine feedback inhibition of PDH is one block point in these enzymatic pathways. Thus overproduction of an enzyme lacking feedback inhibition, such as those provided herein, may lead to enhanced production of these relevant isoquinoline alkaloids.

Enhanced production of HPP via expression of the enzymes provided herein may also lead to increased accumulation of HPP-derived compounds such as the tocopherols (Vitamin E). Biochemical synthesis of the tocopherols is difficult and expensive thus natural production is preferable. Vitamin E has been shown to be beneficial for radioprotection, reversing atherosclerosis and treating cancer as well as many other diseases or conditions. Attempts to overexpress genes in the tocopherol synthesis pathway have met with limited success. Overexpression of the enzymes provided herein may provide additional HPP and be useful in combination with overexpression of genes in the tocopherol synthesis pathway to result in overproduction of tocopherols. Consistent with this concept, overexpression of a CM-PDH enzyme from various microbes together with plant HPP dioxygenase increased flux into homogentisate (FIG. 1), resulting in an up to tenfold increase in its derived compounds, tocochromanols (vitamin E) in previous studies. These examples, however, used CM-PDH enzymes that are still inhibited by L-Tyr. Given that CM and TyrAT are already present in the cytosol of most, if not all, plant species, the identified legume PDH enzymes can be introduced into non-legumes to reconstruct a cytosolic PDH pathway that is not inhibited by HPP or L-Tyr and to further enhance the production of L-Tyr- and HPP-derived natural products.

The transgenic plants expressing the enzymes provided herein may also have increased resistance to herbicides and/or increased production of at least one product of the tyrosine or HPP pathway, as compared to a control plant. Increased HPP and plastoquinone synthesis may lead to enhanced resistance to HPPD (4-hydroxyphenypyruvate dioxygenase) herbicides. Plastoquinone is derived from HPP and plays an essential role as an electron carrier of the photosynthesis pathway and as a co-factor of carotenoid biosynthesis. Inhibition of plastoquinone biosynthesis at the HPPD-catalyzed reaction step leads to bleaching and lethal phenotypes in plants. Several herbicides work by inhibition of HPPD. Production of additional HPP by overexpression of an enzyme lacking feedback inhibition may lead to increased resistance to HPPD targeting herbicides. Non-limiting examples of herbicides to which the plants expressing the PDH or ADH enzymes described herein may be resistant to include the triketone class of herbicides such as sulcotrione, mesotrione, nitisnone, leptospermone, Mikado, fluorochloridone, and isoxaflutole.

Betalains are pigments produced by plants such as red beets which also have antioxidant activities and beneficial health-related properties. The betalains are a natural red pigment for use in food and cosmetic production. They also may be useful to protect against certain cancers. Betalains are extracted from the roots of red beets and increased production of the pigment is needed. Over-expression of the polypeptides provided herein may be useful to increase betalain production.

Portions or parts of these transgenic plants are also useful. Portions and parts of plants includes, but is not limited to, plant cells, plant tissue, plant progeny, plant asexual propagates, plant seeds. Transgenic plant cells comprising a polynucleotide encoding a polypeptide capable of increasing resistance to herbicides and/or increased production of at least one product of the tyrosine or HPP pathway are also provided. Suitably the plant cells are soybean or other legume or cereal plant cells, but beet or other plant cells are also encompassed. Suitably the cells are capable of regenerating a plant. The transgenic cells may be found in a seed. A plant, such as a soybean plant, may include the transgenic cells. The plant may be grown from a seed comprising transgenic cells or may be grown by any other means available to those of skill in the art. Chimeric plants comprising transgenic cells are also provided and encompassed.

The plant is suitably a soybean plant, or other legumes such as alfalfa or portions thereof. The polynucleotides may also be transferred into other legumes plants, or homologs of these polypeptides or polynucleotides encoding the polypeptides from other plants, or synthetic genes encoding products similar to the polypeptides encoded by Glyma18g02650, Glyma11g35760, Glyma14g05990 and/or Mtruncatula3g071980 or the polypeptides of SEQ ID NOs: 2, 4, 6, 8, or 13-26 may be overexpressed in those plants.

Other plants include but are not limited to cereal plants or other plants as discussed above. The overexpression of the genes may increase the resistance of plants to herbicides, such as isoxaflutole or sulcotrione, which target the HPP deoxygenase as discussed above.

The expression of the polynucleotides may be increased by increasing the copy number of the polynucleotide or the expression in the plant or in cells of the plant. These plants may then be used in traditional breeding. Alternatively the expression may be increased using recombinant DNA technology, e.g., by using a strong or inducible promoter to drive increased expression of one or more polynucleotides.

A plant includes any portion of the plant including but not limited to a whole plant, a portion of a plant such as a part of a root, leaf, stem, seed, pod, flower, cell, tissue or plant germplasm or any progeny thereof. Germplasm refers to genetic material from an individual or group of individuals or a clone derived from a line, cultivar, variety or culture. Plant refers to whole plants or portions thereof including, but not limited to, plant cells, plant protoplasts, plant tissue culture cells or calli. For example, soybean plant refers to whole soybean plant or portions thereof including, but not limited to, soybean plant cells, soybean plant protoplasts, soybean plant tissue culture cells or calli. A plant cell refers to cells harvested or derived from any portion of the plant or plant tissue culture cells or calli.

Expression of Glyma18g02650, Glyma11g35760, Glyma14g05990 and/or Mtruncatula3g071980 and/or the polypeptides of SEQ ID NOs: 2, 4, 6, 8, or 13-26 may be increased in a variety of ways including several apparent to those of skill in the art and may be include transgenic, non-transgenic and traditional breeding methodologies. For example, the expression of the polypeptide encoded by Glyma18g02650, Glyma11g35760, Glyma14g05990, Mtruncatula3g071980 and/or SEQ ID NOs: 13-26 may be increased by introducing a construct including a promoter operational in the plant operably linked to a polynucleotide encoding the polypeptide into cells of the plant. Suitably, the cells are root cells, leaf cells, seed pods or flowers.

Alternatively, the expression of the polypeptide encoded by Glyma11g02650, Glyma11g35760, Glyma14g05990, Mtruncatula3g071980 and/or the polypeptides of SEQ ID NOs: 2, 4, 6, 8, or 13-26 may be increased by introducing a transgene including a promoter operational in the plant operably linked to a polynucleotide encoding the polypeptide into cells of the plant. The promoter may be a constitutive or inducible promoter capable of inducing expression of a polynucleotide in all or part of the plant, plant roots, plant stems, plant leaves, flowers, seed pods or other plant parts or plant cells.

In another embodiment, the expression of Glyma18g02650, Glyma11g35760, Glyma14g05990, Mtruncatula3g071980 and/or the polypeptides of SEQ ID Nos: 2, 4, 6, 8, or 13-26 may be increased by increasing expression of the native polypeptide in a plant, specific portions or parts of the plant or in cells of the plant. In another embodiment, the expression of Glyma18g02650, Glyma11g35760, Glyma14g05990, Mtruncatula3g071980 and/or the polypeptides of SEQ ID NOs: 2, 4, 6, 8, or 13-26 may be increased by increasing expression of a recombinant or non-native polypeptide in a plant, in portions or parts of the plant or in cells of the plant. In another embodiment, expression may be increased b increasing the copy number of Glyma18g02650, Glyma11g35760, Glyma14g05990, Mtruncatula3g071980 and/or the polypeptides of SEQ ID NOs: 2, 4, 6, 8, or 13-26.

Other mechanisms for increasing the expression of Glyma18g02650, Glyma11g35760, Glyma14g05990, Mtruncatula3g071980 and/or the polypeptides of SEQ ID NOs: 2, 4, 6, 8, or 13-26 include, but are not limited to, increasing expression of a transcriptional activator, reducing expression of a transcriptional repressor, addition of an enhancer region capable of increasing expression of Glyma18g802650, Glyma11g35760, Glyma14g05990, Mtruncatula3g071980 and/or the polypeptides of SEQ ID NOs: 2, 4, 6, 8, or 13-26, increasing mRNA stability, altering DNA methylation, histone aceta or other epigenetic or chromatin modifications in the vicinity of the relevant genes, or increasing protein or polypeptide stability.

In addition to the use of transgenic technology to introduce additional copies or increase expression of the genes and mediate the increased expression of the polypeptides of Glyma18g02650, Glyma11g35760, Glyma14g05990, Mtruncatula3g071980 and/or the polypeptides of SEQ ID NOs: 2, 4, 6, 8, or 13-26 in plants, transgenic or non-transgenic technology may be used in other was to increase expression of the polypeptides. For example, plant tissue culture and regeneration, mutations or altered expression of plant genes other than Glyma18g02650, Glyma11g35760. Glyma14g05990, Mtruncatula3g071980 and/or the polypeptides of SEQ ID NOs: 2, 4, 6, 8, or 13-26 or transgenic technologies, can be used to create instability in the plant genome and the instability may create changes in copy number or gene expression behavior. The new copy number or gene expression behavior can then be stabilized by removal of the variation-inducing mutations or treatments, for example by further plant propagation or a conventional cross. Examples of transgenic technologies that might be used in this way include targeted zinc fingers, ribozymes or other sequence-targeted enzymes that create double stranded DNA breaks at or close to the genes of interest, the Cre/loxP system from bacteriophage lambda or other similar systems like frt/flp, Transcription Activator-Like Effector Nucleases (TALENs), artificial DNA or RNA sequences designed to recombine with the genes or close to the genes that can be introduced transiently, or enzymes that "shuffle" DNA such as the mammalian Rag1 enzyme or DNA transposases, Mutations or altered expression of endogenous plant genes involved in DNA recombination, DNA rearrangement and/or DNA repair pathways are additional examples.

Non-transgenic means of generating plant varieties carrying traits of interest such as increased resistance to herbicides or increased production of desirable products are available to those of skill in the art and include traditional breeding, chemical or other means of generating chromosome abnormalities, such as chemically induced chromosome doubling and artificial rescue of polyploids followed by chromosome loss, knocking-out DNA repair mechanisms or increasing the likelihood of recombination or gene duplication by generation of chromosomal breaks. Other means of non-transgenetically increasing the expression or copy number of Glyma18g02650, Glyma11g35760, Glyma14g05990, Mtruncatula3g071980 and/or the polypeptides of SEQ ID NOs: 2, 4, 6, 8, or 13-26 include the following: screening for mutations in plant DNA encoding miRNAs or other small RNAs, plant transcription factors, or other genetic elements that impact Glyma18g02650 Glyma11g35760, Glyma14g05990, Mtruncatula3g071980 and/or the polypeptides of SEQ ID NOs: 2, 4, 6, 8, or 13-26 expression; screening large field or breeding populations for spontaneous variation in copy number or sequence within the genes identified by screening of plants for the desired trait or protein expression traits as described in preceding paragraphs; crossing of lines that contain difference within the genes identified; chemical or radiation mutagenesis or plant tissue culture regeneration that creates chromosome instability or gene expression changes, followed by screening of plants gene or protein expression traits as described in preceding paragraphs; or introduction by conventional genetic crossing of non-transgenic loci that create or increase genome instability, followed by screening, of plants for the desired trait. Examples of loci that could be used to create genomic instability include active transposons (natural or artificially introduced from other species), loci that activate endogenous transposons (for example mutations affecting DNA methylation or small RNA processing such as equivalent mutations to met1 in *Arabidopsis* or mop1 in maize), mutation of plant genes that impact DNA repair or suppress illegitimate recombination such as those orthologous or similar in function to the Sgs1 helicase of yeast or RecQ of *E. coli*, or overexpression of genes such as RAD50 or RAD52 of yeast that mediate illegitimate recombination. Those of skill in the art may find and use other transgenic and non-transgenic methods of increasing expression of Glyma18g02650, Glyma11g35760, Glyma14g05990, Mtruncatula3g71980 and/or the polypeptides of SEQ ID NOs: 2, 4, 6, 8, or 13-26.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United. States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

Identification of ADH or PDH Enzyme Candidates from Soybean.

Figures 9, 9A:
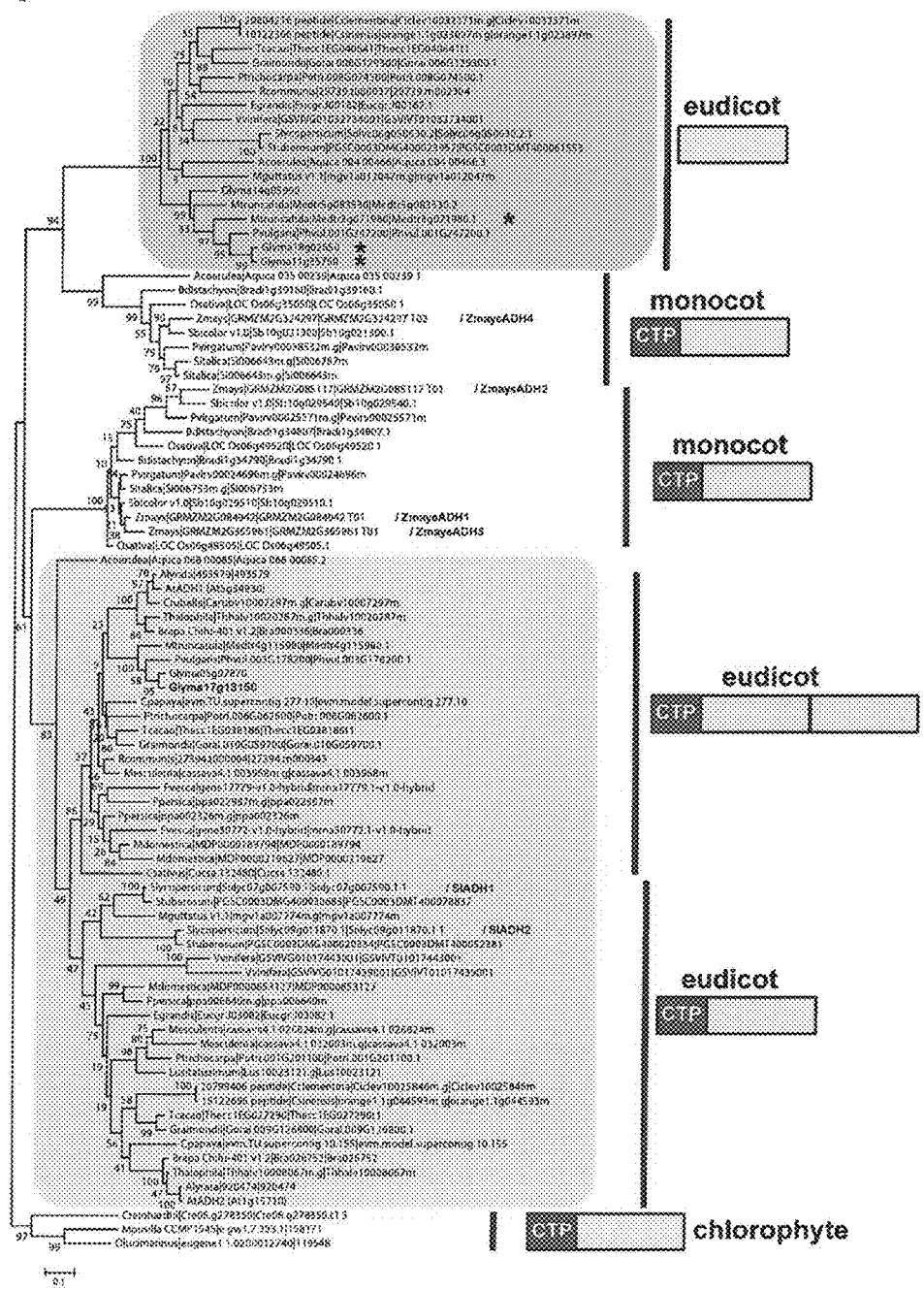
FIG. 9 shows the phylogenetic analysis of plant PDH and ADH enzymes.
FIG. 9A shows the maximum-likelihood phylogenetic analysis using candidate soybean PDHs together with ADH/PDH homologs in flowering plants and green algae, which were identified by blastp searches using GmPDH1 as the query against the phytozome database (www.phytozome.net). The percentage of replicate trees in which the associated sequences clustered together are indicated next to the branches. An eudicot clade (blue) distinct from that containing AtADHs (green) was formed. Homologs in green algae were used as the outgroup. Gene numbers following names are based on phytozome.net, except for *Arabidopsis* GI numbers shown in parentheses. Tomato and maize ADH homologs previously identified are shown next to gene numbers. Stars denote enzymes exhibiting PDH activity (FIG. 3C). Protein structure is shown next to the phylogeny with a green and gray box indicating a predicted CTP and a PDH/ADH domain, respectively.
Figures 9, 9B:
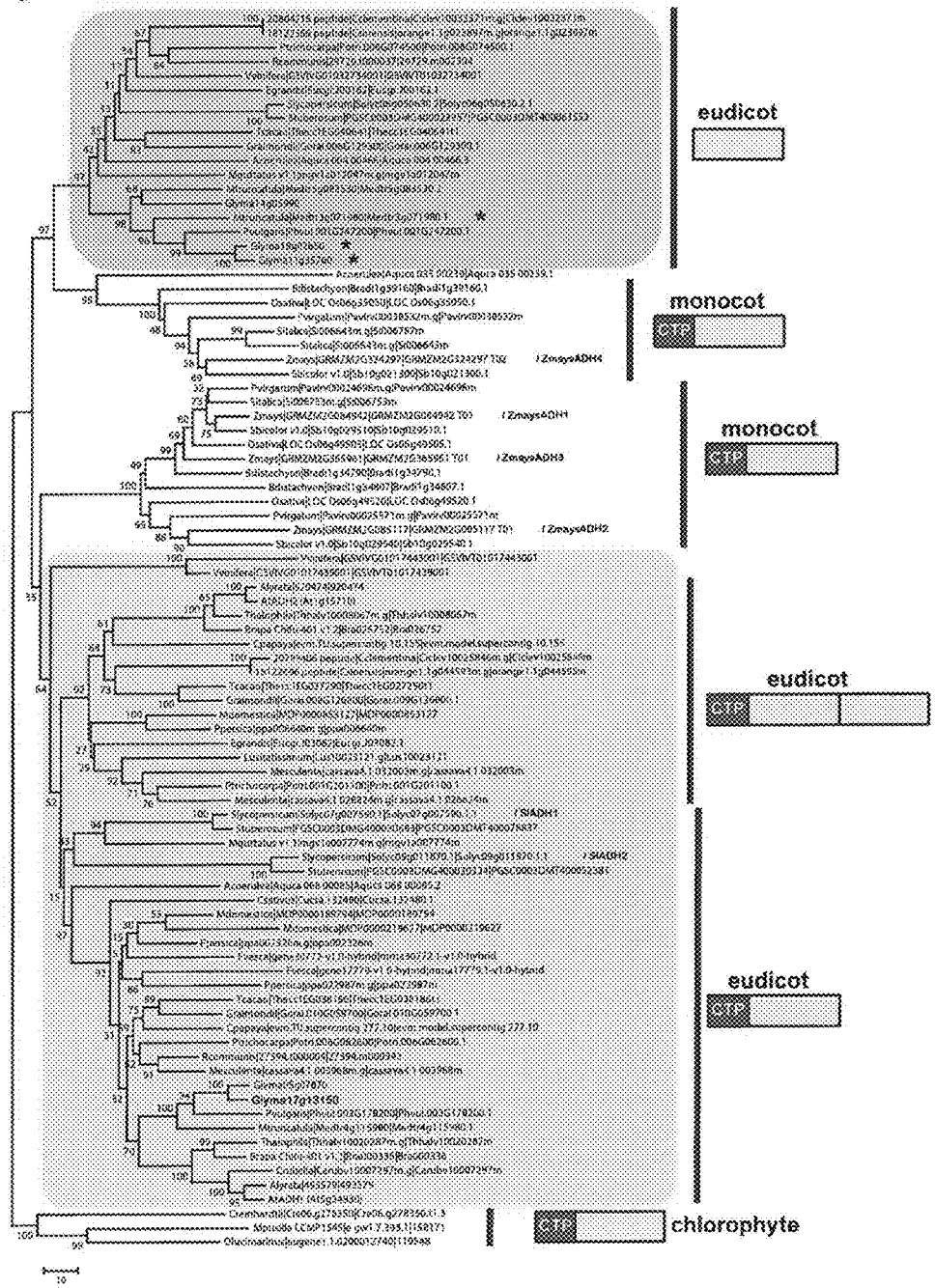
FIG. 9B is a neighbor-joining phylogeny constructed using the same sequences as above.
Figure 10:
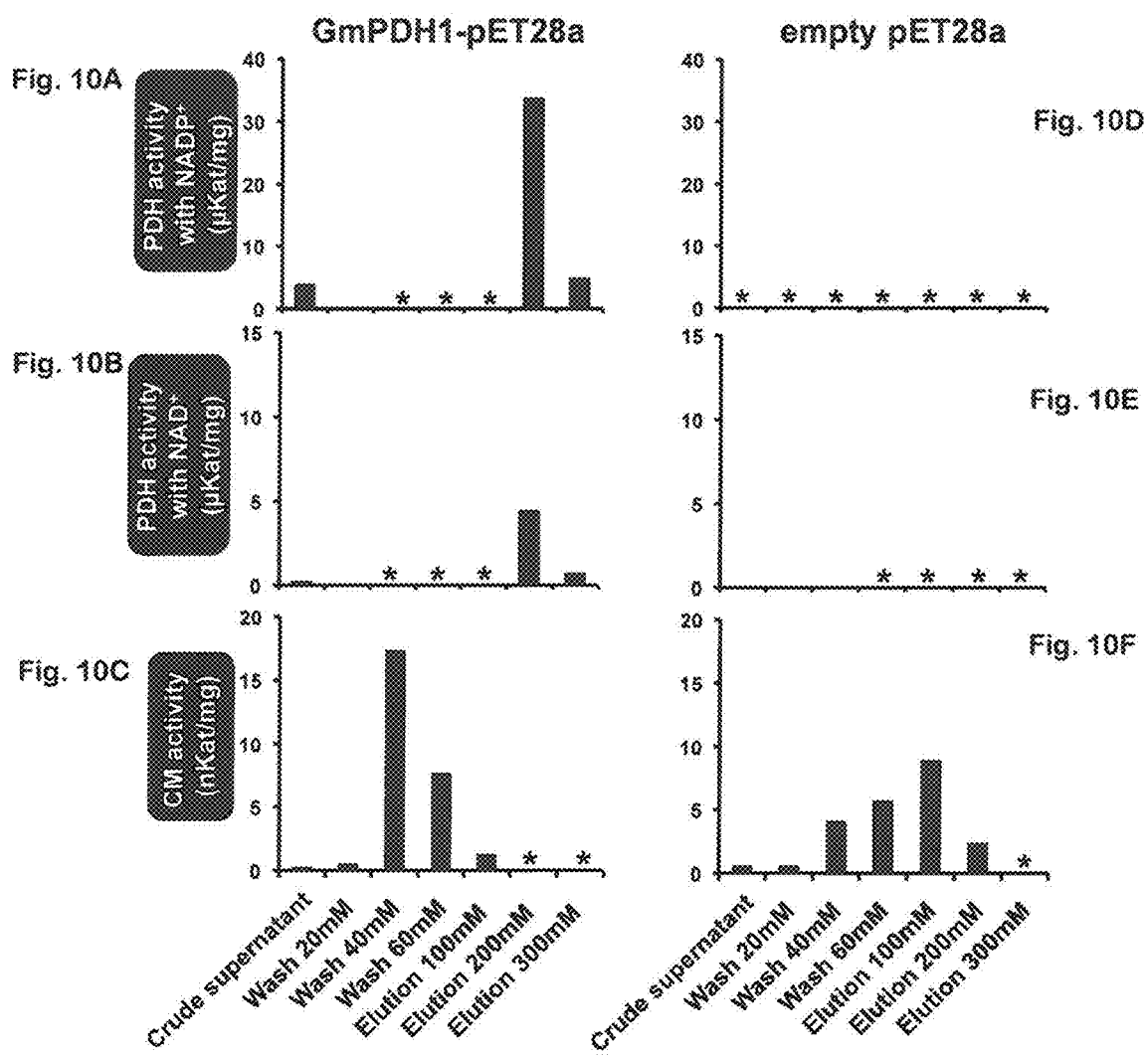
FIG. 10 is a set of graphs showing CM and PDH activity in fractions collected during recombinant enzyme purification. Elution fractions with indicated imidazole concentration (mM) were collected during enzyme purification from *E. coli* expressing pET28a-GmPDH1 (FIG. 10A-C) and empty-pET28a vector (FIG. 10D-F), side by side. The supernatant of the initial *E. coli* crude extracts and the individual fractions were tested for NADP+-dependent PDH activity (FIG. 10A and FIG. 10D), NAD+-dependent PDH activity (FIG. 10B and FIG. 10E) and chorismate mutase (CM) activity (FIG. 10C and FIG. 10F), NADP+-dependent PDH activity was detected in both the crude and elution fractions of GmPDH1 (FIG. 10A), but not in the empty vector control (FIG. 10D), consistent with the lack of endogenous NADP+-dependent PDH activity in *E. coli*. NAD+-dependent PDH activity was detected in *E. coli* crude extracts of GmPDH1 (FIG. 10B) and trace levels in the empty vector control (FIG. 10E). However, in the elution fractions, only GmPDH1 (FIG. 10B) showed NAD+-dependent PDH activity. CM activity was detected from the crude extracts of both GmPDH1 and the empty vector control but eliminated from the elution fractions (with 200 and 300 mM imidazole) of GmPDH1 (FIG. 10C), which were used for further analysis. These results indicate that the purified GmPDH1 fractions are not contaminated with endogenous CM-PDH from *E. coli*; additionally, NADP+-dependent PDH activity can not be associated with *E. coli* CM-PDH (FIG. 10D). Asterisks indicate no activity detected.

Blastp searches were performed using the protein sequences of two ADH enzymes from *A. thaliana* (AtADH1/At5g34930, NP_98343.1; AtADH2/At1g15710, NP_73023.1) and PDH enzymes from *E. coli* (*E. coli* CM-PDH, NP_755003) and *A. aeolicus* (AaPDH, NP_214202) as queries against the soybean genome (*Glycine max* Wm82 v1.1 at http://www.phytozome.net/). The same 12 candidates were identified by the blastp searches using either plant or bacterial TyaA enzymes. Putative ADH or PDH enzymes from other plant species were similarly identified by blastp from the genomes of *Brachypodium distachyon, Chlamydomonas reinhardtii, Citrus clementina, Fragaria vesca, Medicago truncatula, Ostreococcus lucimarinus, Populus trichocorpa, Solanum lycopersicum* and *Sorghum bicolor*. A multiple sequence alignment was performed by MUSCLE (Edgar, Nucleic Acids Res. 32:1792-1797 (2004)) using the identified ADH and PDH candidate enzymes from soybean, other plants and green algae, together with characterized ADH and PDH enzymes from *A. thaliana*. Evolutionary distances were inferred from a maximum likelihood phylogenetic analysis created using MEGA5 (http://www.megasoftware.net/) with 1,000 bootstrap replicates using 29 amino acid sequences (FIG. 3A). All positions with <75% site coverage were removed, leaving 274 positions in the final analysis. The tree is drawn to scale, with branch lengths measured in the number of substitutions per site. Phylogenies created using maximum parsimony and neighbor-joining methods yielded consistent results with the maximum likelihood, method (FIG. 3A). A more comprehensive maximum likelihood phylogeny was created using blastp searches similar to those above against Chlorophytes and flowering plants found in the http://www.phytozomene.net/ database (FIGS. 9 and 10).

A phylogeny was created for CM isoforms from various plant species. Blastp searches were performed to identify CM isoforms in soybean as well as *P. vulgaris, M. truncatula, S. lycapersicum, S. bicolor* and *O. sativa* using the amino acid sequence of CMs from *A. thaliana* (AtCM2/

At5g10870, NP_96648) and Petunia×hybrida cv. 'Mitchell Diploid' (PhCM2, ACI41890) as queries. Putative CMs from various species were aligned by MUSCLE, and a neighbor-joining phylogeny with 1,000 bootstrap replicates was created and rooted to CM from Saccharomyces cerevisiae (ScCM, AAB59309).

Expression Analysis of Soybean ADH and PDH Candidate Genes.

Gene expression profiles of all 12 candidate genes in various tissue types was first examined on the basis of two independent expression databases; http://www.soybase.org/ and Soybean eFpBrowser (http://bar.utoronto.ca/efpsoybean/cgi-bin/efpWeb.cgi; FIG. 7). For experimental validation (FIG. 8), RNA was extracted from soybean leaf, root, seed pod and flower tissues. RNA was converted into cDNA using reverse transcriptase (Applied Biosystems, Grand Island, N.Y.) with an oligo d(T) primer. Gene-specific primers (Table 2) were used to amplify soybean candidates that showed expression in all tissues (FIGS. 7 and 8) where PDH activity was detected (FIG. 2C). A housekeeping gene, Glyma18g8050 (eukaryotic translation initiation factor 3 subunit G, eIF), was used as a control to ensure cDNAs from all tissues were intact and loaded, at comparable amounts (FIG. 8).

Enzyme Extraction from Soybean, Medicago and Arabidopsis Tissues.

Tissues from 4-week-old plants grown under a long day regimen (16 h light/8 h dark at 22° C. in growth chambers for Arabidopsis and 14 h light/10 h dark at 24° C. in a greenhouse for Medicago and soybean) were ground to a fine powder in a prechilled mortar and pestle under liquid nitrogen. Extraction buffer (25 mM HEPES, pH 7, 50 mM KCl, 10% ethylene glycol, 1% polyvinylpyrrolidone (PVP) and 1 mM dithiothreitol (DTT)) was added in a 1:3 ratio of tissue to buffer (w/v). The slurry was centrifuged for 20 min at 4° C., at 20,000 g. The supernatant was desalted using a gel filtration column (Sephadex G50-80 resin, Sigma-Aldrich, St. Louis, Mo.) equilibrated with the extraction buffer without DTT and PVP, and then used for enzyme assays (described below). Protein concentrations were determined by a Bradford assay (Bio-Rad Protein Assay, Bio-Rad, Hercules, Calif.).

Cloning of ADH and PDH Candidates and Generation of the Purified Recombinant Enzymes.

The ADH and PDH candidate genes were PCR amplified from soybean or Medicago cDNA. Genes were amplified using corresponding gene-specific primers (Table 2) and Phusion DNA polymerase (Thermo, Waltham, Mass.) with the following conditions: an initial denaturation at 95° C. for 5 min, 35 cycles of amplification at 95° C. for 20 s, 60-65° C. for 20 s, 72° C. for 30 s, with a final extension at 72° C. for 5 min. The PCR fragments were purified using QIAquick gel extraction kit (Qiagen, Valencia, Calif.) and were inserted into the pET28a vector (Novagen, Darmstadt, Germany) at EcoRI and NdeI sites using the In-Fusion cloning method (Clontech, Mount View, Calif.). Sequencing of the cloned plasmids confirmed that no errors were introduced during PCR amplification and cloning.

TABLE 2

Primers used in this study.

| Gene | | Sequence (5'-3')(SEQ ID NO:) |
|---|---|---|
| In-fusion cloning | | |
| Glyma5g07870 | F | CGCGCGGCAGCCATATGGCCATCGACGCGGCCCAG (29) |
| Glyma5g07870 | R | GACGGAGCTCGAATTCTTATTTATCTTCAGATATCTTAGGC (30) |
| Glyma11g35760 | F | CGCGCGGCAGCCATATGACAACCATGTCAACCTC (31) |
| Glyma11g35760 | R | GACGGAGCTCGAATTCGCATCAACTTTCGGTTCTT (32) |
| Glyma14g05990 | F | GATCTAGACTCGAGGGTACCTATGTCAACATGGTCTCTGA (33) |
| Glyma14g05990 | R | CTAGTGCATGCGGCCGCACATTCAGTTTTTTCTAGACC (34) |
| Glyma17g13150 | F | CGCGCGGCAGCCATATGGCCCTCCGTATTCGC (35) |
| Glyma17g13150 | R | GACGGAGCTCGAATTCAGTCCGTGTTTGTTGAACTG (36) |
| Glyma 18g02650 | F | CGCGCGGCAGCCATATGTCAACCTCATCCTC (37) |
| Glyma 18g02650 | R | GACGGAGCTCGAATTCAATATGCATCAACTTTCAG (38) |
| Mt3g071980 | F | CGCGCGGCAGCCATATGTCATCATCTTCCAAA (39) |
| Mt3g071980 | R | GACGGAGCTCGAATTCTCAACTCTCAGTTCTTTCT (40) |
| AtIg15710 | F | CGCGCGGCAGCCATATGGCAATCGACGCCGCCCAA (41) |
| AtIg15710 | R | GCTCGAATTCGGATCCTTAAGATGATGATGATGATGATG (42) |
| GFP-fusion | | |
| Glyma 18g02650 | F | GATCTAGACTCGAGGGTACCTATGTCAACCTCATCCTCTTC (43) |
| Glyma18g02650 | R | CTAGTGCATGCGGCCGCACTTTCAGTTCTTTTATGACCC (44) |
| Mt3g071980 | F | GATCTAGACTCGAGGGTACCTATGTCATCATCTTCCAAAAG (45) |
| Mt3g071980 | R | CTAGTGCATGCGGCCGCACTCTCAGTTCTTTCTGGGT (46) |
| AtIg 15710 | F | GATCTAGACTCGAGGGTACCAATGCTACTCCATTTCTCTC (47) |
| AtIg15710 | R | CTAGTGCATGCGGCCGCAGATGATGATGATGATGATGA (48) |
| RT-PCR | | |
| Glyma5g07870 | F | CGACCACGATAAGTTCGCTG (49) |
| Glyma5g07870 | R | CTTGGTTTTGTCATCAGACTGGT (50) |
| Glyma11g35760 | F | GCATTGTTGGATTCGGCAAC (51) |
| Glyma11g35760 | R | TTTTATGACCCTGCTCCCCA (52) |
| Glyma13g01050 | F | GAACGCCCCGAAGTCATTTT (53) |
| Glyma13g01050 | R | CCACTCCACCCATCTTTTGC (54) |
| Glyma14g05990 | F | ATTGGCGTAGTTGGGTTTGG (55) |
| Glyma14g05990 | R | AGATCTTGCCACCCATCCTT (56) |

TABLE 2-continued

Primers used in this study.

| Gene | | Sequence (5'-3') (SEQ ID NO:) |
|---|---|---|
| Glyma14g 15060 | F | CAAATACCATCTCTTCTTACAAACCC (57) |
| Glyma14g15060 | R | TCACCGGAACTTATCGTGGC (58) |
| Glyma17g13150 | F | CCTCGGAATTTTCGCCAGAG (59) |
| Glyma17g13150 | R | AAGAAACTGACCAAAGTTGCCA (60) |
| Glyma18g18050 | F | AGGACGGGAACAAGGTGAAG (61) |
| Glyma18g18050 | R | GCAAATCAGGCTCTCTCG (62) |

For recombinant protein expression, the cloned pET28a vectors were introduced into Rosetta-2 *E. coli* competent cells (Novagen) and cultured overnight at 37° C., 200 r.p.m. in 10 ml LB medium containing kanamycin (100 μg/ml) and chloramphenicol (100 μg/ml). Two milliliters of the overnight culture were transferred to 50 ml LB medium with the same antibiotics and further incubated at 37° C. and 200 r.p.m. until the $OD_{600}$ reached 0.3. The temperature was then changed to 18° C. and, after 1 h, isopropyl β-D-1-thiogalactopyranoside (IPTG, 0.5 M final concentration) was added to induce recombinant protein expression. After overnight incubation at 18° C. under constant shaking at 200 r.p.m, cultures were harvested by centrifugation at 2,000 g for 30 min at 4° C. and the pellet was resuspended in an appropriate volume of lysis buffer (25 mM HEPES, pH 7, 50 mM KCl, 10% ethylene glycol, 1 mM phenylmethylsulfonyl fluoride (PMSF) and 1 mM DTT) calculated on the basis of the formula ($OD_{600}$×ml volume of culture)/30. The resuspended pellet was sonicated three times for 15 s. The cell lysate was centrifuged at 16,000 g for 10 min at 4° C. and the supernatant was applied to a column containing 500 μl PerfectPro Ni-NTA resin (5 PRIME, Hamburg, Germany). The column was washed with ten times the bed volume of wash buffer I (50 mM sodium phosphate buffer, pH 8.0, 300 mM NaCl, 20 mM imidazole) followed by ten times the bed volume of wash buffer II (50 mM sodium phosphate buffer, pH 8.0, 300 mM NaCl, 40 mM imidazole) and then wash buffer III (50 mM sodium phosphate buffer, pH 8.0, 300 mM NaCl, 60 mM imidazole). The recombinant enzymes containing an N-terminal $His_6$ tag were eluted from the resin with 1 ml of elution buffer (50 mM sodium phosphate buffer, pH. 8.0, 300 mM NaCl, 500 mM imidazole) and desalted as described above. The purity of the purified recombinant enzymes was estimated by running on SDS-PAGE gel (FIG. 12) and analyzing with ImageJ (http://imagej.nih.gov/ij/). The recombinant enzyme of Glyma11g35760 was tested for Tyr sensitivity (FIG. 5A) using crude *E. coli* extract as its purification was not successful owing to its low expression (FIG. 3B and FIG. 3C) and insolubility.

PDH and ADH Enzyme Assays.

ADH and PDH reactions contained 25 mM HEPES (pH 7.5), 50 mM KCl, 10% ethylene glycol, 1 mM $NADP^+$ (or $NAD^+$), 2 mM substrate (L-arogenate or prephenate, respectively) unless otherwise noted. Arogenate was prepared by enzymatic conversion from prephenate (Sigma-Aldrich), as previously reported. Reactions were started by addition of enzyme from various sources and incubated at 37° C. for a given amount of time, as noted below.

Figure 6:
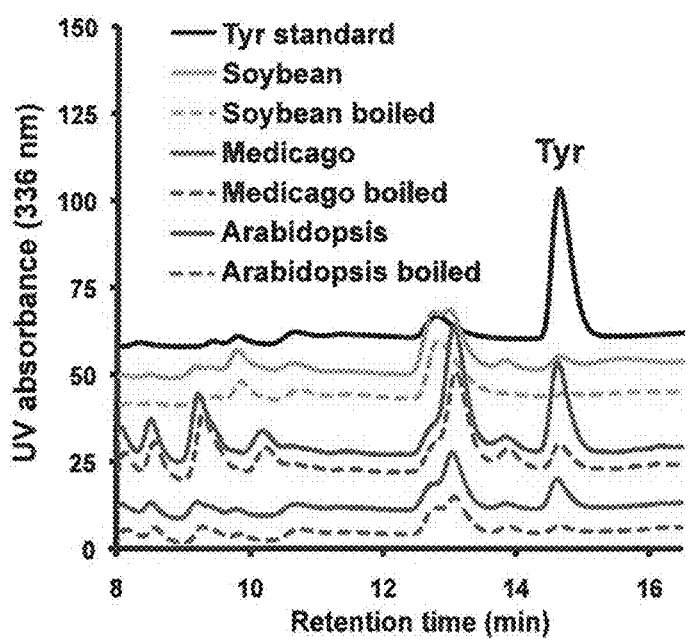
FIG. 6 is a graph showing HPLC detection of ADH activity from plant tissues. The product of ADH reactions, L-Tyr was detected as its o-phthalaldehyde derivative at 336 nm (black). Enzyme assays containing crude leaf extracts from soybean (orange), *Medicago* (green) and *Arabidopsis* (blue) were compared with their respective boiled extract control (dotted). Reactions contained 1.5 mM L-arogenate and 1 mM NADP+ and were incubated for 45 min at 37° C. ADH activity was detected in all plants.

HPLC-based methods were used to directly detect the final products of ADH and PDH assays, Tyr and HPP, respectively from crude *E. coli* extracts (FIG. 3B and FIG. 3C) and crude plant extracts (FIG. 2A and FIG. 6). For HPLC detection of PDH activity, reactions were incubated for 45 min and terminated by addition of $NaBH_4$, which converts the reaction product HPP (which produced multiple peaks; FIG. 6) into hydroxyphenyllactic acid (HPLA), followed by neutralization with 100 μl of 6 N HCl. The conversion and recovery rate was 80±1.5% s.d. which was taken into account for the calculation of specific activity from crude plant extracts (FIG. 2C). HPLA was detected as a single peak (FIG. 2A) after being separated by HPLC (Agilent 1260, Santa Clara, Calif.) equipped with a ZORBAX SB-C18 column (Agilent) using a 6-min isocratic elution at 25% methanol in 0.1% phosphoric acid, followed by a 20-min linear gradient of 25-60% methanol at a flow rate of 1.0 ml/min. HPLA was detected using UV absorbance at 270 nm and quantified by a calibration curve generated from the authentic HPLA standard (Sigma-Aldrich). For HPLC-based detection of ADH activity (FIG. 3B), reactions were incubated for 45 min and terminated by addition of methanol to a final concentration of 66% (v/v). The product, Tyr, was derivatized with OPA and separated on a ZORBAX eclipse-XDB C18 column (Agilent) using a 30-min linear gradient of 20-45% methanol in 0.1% ammonium acetate at a flow rate of 0.8 ml/min. Tyr was detected by UV absorption at 336 nm and quantified on the basis of a calibration curve generated by the authentic Tyr standard (Acros, Geel, Belgium).

To test the electron acceptor and substrate preference of purified recombinant enzymes (FIG. 12), we incubated reactions for 15 min with 1.5 mM substrate (L-arogenate or prephenate) and 1 mM cofactor ($NAD^+$ or $NADP^+$). Assays were conducted with decreasing enzyme concentrations and stopped by placing on ice, and the production of reduced cofactor, NAD(P)H, was Measured at 340 nm using a spectrophotometer (NanoDrop 2000, Thermo).

Kinetic parameters of purified recombinant GmPDH1 and MtPDH1 for ADH activity (Table 3) were determined from assays conducted using varying L-arogenate concentrations (39 μM to 5 mM). Assays were incubated for 15 min with 0.5 mM $NADP^+$, by placing on ice and quantified by measuring production of NADPH by absorbance at 340 nm. Kinetic parameters of purified recombinant GmPDH1 and MtPDH1 for PDH activity (Table 3) were determined from assays conducted using varying prephenate concentrations (29 μM to 3.5 mM). Assays with 0.5 mM $NADP^+$ were monitored continuously at 340 nm using a microplate reader (Tecan GENios, Zurich, Switzerland) for 7 min. Kinetic parameters were determined using hyperbolic regression analysis in Hyper (http://homepage.ntlworld.com/john.eastetby/software.html). Enzyme assays were carried out at a protein concentration and reaction time that were in the linear range and proportional to reaction velocity. The final enzyme concentrations of the purified recombinant GmPDH1 and MtPDH1 were 0.9 μg/ml and 0.7 μg/ml for PDH activity and 3.0 μg/ml and 1.4 μg/ml for ADH activity, respectively.

TABLE 3

Kinetic analysis of GmPDH1 and MtPDH1.

| | Substrate | $K_m$ (mM) | $k_{cat}$ (s$^{-1}$) | $k_{cat}/K_m$ (mM$^{-1}$ s$^{-1}$) | $V_{max}$ (nKat mg$^{-1}$) |
|---|---|---|---|---|---|
| GmPDH1 | Prephenate | 0.127 ± 0.02 | 26.3 ± 0.7 | 217 ± 25 | 800 ± 21 |
| MtPDH1 | Prephenate | 0.223 ± 0.02 | 21.8 ± 2.4 | 100 ± 16 | 655 ± 73 |
| GmPDH1 | Arogenate | 17.0 ± 2.8 | 10.1 ± 1.8 | 0.59 ± 0.01 | 307 ± 56 |
| MtPDH1 | Arogenate | 42.5 ± 21.8 | 5.5 ± 3.2 | 0.05 ± 0.02 | 229 ± 96 |

Kinetic parameters were obtained with reactions incubated at 37° C. using 0.5 mM NADP$^+$ and variable concentrations of prephenate (PDH activity) and L-arogenate (ADH activity) substrate. Data show mean ± s.e.m. (n ≥ 3 independent experiments).

Inhibition Analysis of PDH and ADH Enzymes and Activity.

Figure 13:
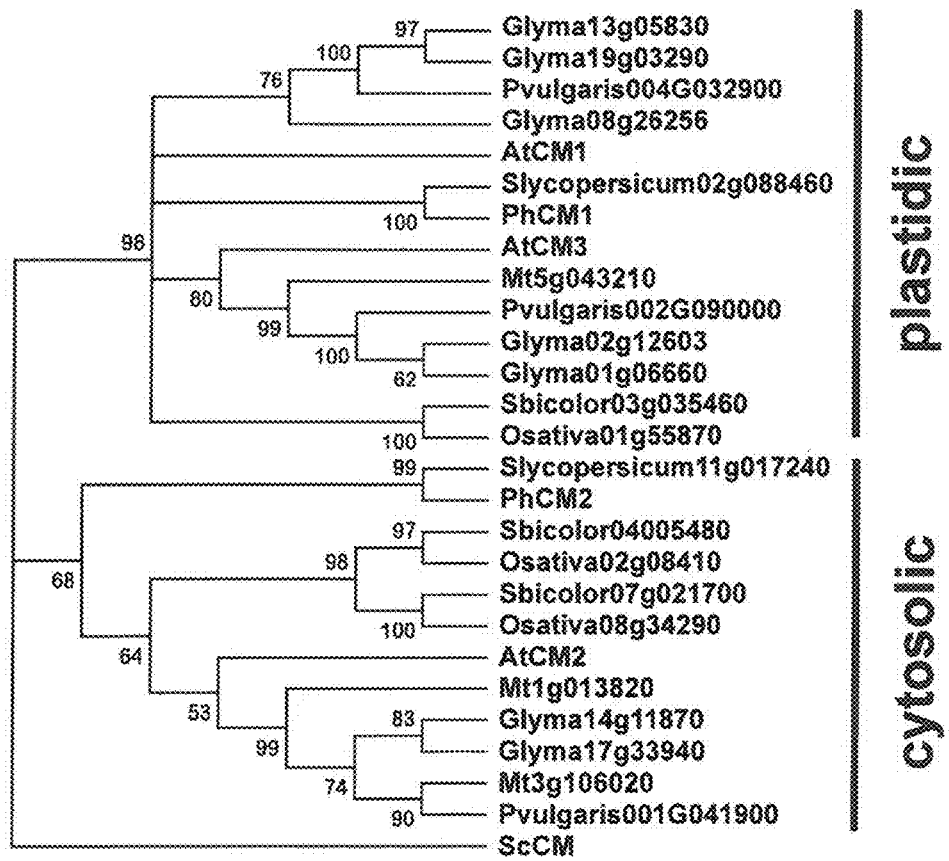
FIG. 13 shows a phylogenetic analysis of CM isoforms in soybean. Neighbor-joining phylogeny of plant CMs, which formed two distinct clades, with one containing known cytosolic CMs lacking CTPs and the other containing known plastidic CMs. The percentage of replicate trees in which the associated sequences clustered together are shown next to the branches, whereas those with less than 50% support were collapsed. The tree was rooted to *Saccharomyces cerevisiae* (ScCM). AtCM1, *Arabidopsis thaliana* CM1; AtCM2, *Arabidopsis thaliana* CM2; AtCM3, *Arabidopsis thaliana* CM3; Glyma, *Glycine max*; Mt. *Medicago truncatula*; Osativa, *Oryza sativa*; PhCM1, *Petunia×hybrida* cv. 'Mitchell Diploid' CM1; PhCM2, *Petunia×hybrida* cv. 'Mitchell Diploid' CM2; Pvulgaris, *Phaseolus vulgaris*; Sbicolor, *Sorghum bicolor*; Slycopersicum, *Solanum lycopersicum*, Gene numbers following the names are based on phytozome.net.

ADH and PDH reactions using GmPDH1, Glyma11g35760, MtPDH1 and AtADH2 (FIG. 5A) contained 200 mM HEPES (pH 7.3), 50 mM KCl, 10% ethylene glycol, 1 mM NADP$^+$ and 1 mM substrate (L-arogenate or prephenate, respectively). Reactions were started by addition of enzyme and incubated at 37° C. for 15 min in the presence of increasing concentrations of effectors: L-Tyr FIG. 5A), L-Phe, L-Trp and HPP. Tyr was dissolved in basic conditions (0.025 N NaOH) to dissolve at high concentrations (up to 10 mM), though 200 mM HEPES maintained the final reaction pH at 7.6. Tyr sensitivity of purified recombinant GmPDH1 and MtPDH1 was also tested at prephenate concentrations ranging from 15 mM to 59 µM, below the $K_m$ values for GmPDH1 and MtPDH1, while keeping the L-Tyr concentration constant at 1 mM (FIG. 13). Enzyme activity was measured for the production of reduced cofactor (NADPH) at 340 nm using a spectrophotometer, except for crude soybean extracts, which were analyzed by HPLC after 45 min incubation and reduction to HPLA as described above.

CM, PPA-AT and PEP Carboxylase Enzyme Assays.

CM activity from E. coli crude extracts and purification fractions (FIG. 11) was determined spectrophotometrically by detecting the formation of prephenate after being converted to phenylpyruvate by acid treatment (Glichrist and Connelly, Methods Enzymol 142:450-463 (1987)). Enzyme assays contained 20 mM Tris HCl (pH 8.0), 1 mM EDTA and 0.5 mM chorismate (Sigma-Aldrich) and were initiated by addition of enzyme. Reactions were incubated for 20 min at 37° C. and stopped by adding 100 µl of 1 N HCl. After a 20 min incubation, 300 µl of 2.5 N NaOH was added, and absorbance at 320 nm was measured by a spectrophotometer (Beckman DU-640, Pasadena, Calif.) to quantify phenylpyruvate formation using an extinction coefficient of 17,500 M$^{-1}$ cm$^{-1}$.

CM activity from crude plant extracts and from cytosolic and plastidic fractions (FIG. 4I) was determined in the presence and absence of 1 mM L-Tyr or L-Trp (FIG. 4I) by detecting phenylpyruvate formation using the same HPLC method for HPLA detection (see above). Assays were set up as described above but were incubated for 60 min at 37° C. before addition of 1 N HCl. Phenylpyruvate was detected by UV absorbance at 270 nm and quantified by comparison to the authentic phenylpyruvate standard (Sigma-Aldrich).

PPA-AT activity (FIG. 4E-FIG. 4H), conversion of prephenate to L-arogenate, was analyzed in crude soybean extracts as well as cytosolic and plastidic fractions. The reactions (20 µl) containing 50 mM sodium phosphate buffer (pH 8), 200 µM PLP, 5 mM L-aspartate (amino donor) and 1 mM prephenate (keto donor) were initiated by addition of enzyme and incubated at 37° C. for 15 min. After termination of the reaction by addition of 40 µl methanol, L-arogenate was derivatized with OPA and separated by HPLC equipped with a ZORBAX eclipse XDB C18 column (Agilent) using a 15-min linear gradient of 10-70% methanol in 0.1% ammonium acetate at a flow rate of 0.5 ml/min and detected at UV absorbance at 336 nm.

PEP carboxylase assays (FIG. 4E-FIG. 4H) were performed on crude soybean extracts and fractions enriched in plastidic and cytosolic proteins as previously reported by coupling, to malate dehydrogenase and monitoring the reduction of NADH at 340 nm (Schuller et al. Plant Physiol 93:1303-1311 (1990)). All enzyme assays were conducted at varied enzyme concentrations to ensure that nonsaturating reaction conditions were used.

Subcellular Fractionation of Soybean Leaf Tissue.

Ten grams of 4-week-old soybean leaves were harvested at the end of the night to deplete starch. The fresh tissues were homogenized using a Polytron (Brinkmann, Westbury, N.Y.) in 10 ml of the plastid isolation buffer (0.5 M sorbitol, 20 mM HEPES (pH 7.4), 10 mM KCl, 1 mM MgCl$_2$, 1 mM EDTA, 5 mM DTT and 1% BSA) (Kong and Rawsthorne, Plant J, 6: 795-805 (1994)). The homogenate was filtered through two layers of micracloth. The residual homogenate left on the micracloth was homogenized again in 10 ml of the isolation buffer and passed through two layers of micracloth, which was repeated once more to yield ~30 ml of homogenate. The combined homogenate was centrifuged at 2,500 g for 5 min. The pellet was washed twice with the isolation buffer, resuspended in 4 ml of lysis buffer (25 mM HEPES (pH 7.5), 50 mM KCl) and left on ice for 20 min to rapture the plastids. The plastid fraction was then desalted twice over a Sephadex G50-80 column and eluted into 1 ml of the PDH reaction buffer (described above). The supernatant, representing the cytosolic fraction, was decanted and centrifuged for 20 min at 12,000 g, and the resulting supernatant was desalted twice as described for the plastid fraction. All fractionation steps were conducted at 4° C.

Subcellular Localization of GFP-Fused PDH Enzymes.

To construct plasmids that express GFP-fusion proteins at the C-terminus of PDH and ADH enzymes, the full-length cDNA of GmPDH1 and MtPDH1 as well as AtADH2 were amplified by Phusion DNA polymerase (Thermo) using gene-specific primers (Table 2), cloned into the pML94-myc-GEP vector at the KpnI and NotI site using the In-Fusion Cloning protocol (Clontech) (Bionda, J Mol Biol 402: 510-523 (2010)). The stop codon of each gene was eliminated for continuous translation through the GFP open reading frame. Sequencing of the cloned plasmids confirmed that no errors were introduced during PCR amplification and cloning.

For protoplast isolation, Arabidopsis plants were grown for four weeks in 12 h light/12 h dark cycles at 22° C. under a light intensity of 120 µE m$^{-2}$ s$^{-1}$. Ten rosette leaves were used to isolate protoplasts following the 'Tape-Arabidopsis Sandwich' protocol, with slight modifications (Wu et al., Plant Methods 5:5-16 (2009)). The bottom epidermis layer of the leaf was removed using 3M magic tape (3M, St Paul, Minn.). The exposed bottom layer of the leaf was placed face down in the cell wall digestion solution (1% cellulase (RPI, Mount Prospect, Ill.) (w/v) and 0.25% macerozyme (RPI) (w/v)) in a petri dish and incubated at 26° C. for 90 min with constant shaking at 40 r.p.m. Protoplasts were sedimented by centrifugation and resuspended in 5 ml W5 solution (154 mM NaCl, 125 mM $CaCl_2$, 5 mM KCl, 5 mM glucose and 2 mM MES, pH 5.7) and left on ice for 30 min. Protoplasts were sedimented again by centrifugation and resuspended in MMg solution (0.4 M mannitol, 15 mM $MgCl_2$, and 4 mM MES, pH 5.7) to a final concentration of 1,000 protoplasts/µl.

Protoplasts were transfected with the plasmids carrying, GFP fusion proteins (FIG. 4A-FIG. 4D) using the polyethylene glycol method (Yoo et al., Nat Protoc 2: 1565-5172 (2007). A free GFP construct (35S-pPZP211) and AtADH2-GFP were used as controls for cytosolic and plastidic localization, respectively. GFP expression was observed 16 h after transfection using a Zeiss ISM 510 Meta confocal laser scanning microscope (Zeiss, Thornwood N.Y.). GFP and chlorophyll were excited at 488 nm using an argon laser, and the emission was detected at 494-537 nm and 601-708 nm with the Meta detector for GFP and chlorophyll respectively.

Statistical Analysis.

For data in which multiple independent replicates were analyzed, results are displayed as the mean±s.e. Student's t-tests were performed to evaluate data for statistically significant differences.

Results

Soybean and *Medicago* Exhibit PDH Activity

Although ADH activity has been detected in all plant tissues analyzed, PDH activity was detected only from plants that belong to the Leguminosae family (Table 1). To identify and characterize plant PDH enzymes in this study, we first developed HPLC-based methods to confidently detect the presence and absence of PDH and ADH activity in different plants (as compared to previous spectrophotometric detections). The products of ADH and PDH activity, Tyr and HPP, respectively, were directly measured in the ADH and PDH reactions using plant extracts from *Arabidopsis* and two legumes, soybean and *Medicago*. The production of Tyr from arogenate (ADH activity), detected as its o-phthalaldehyde (ORA) derivative, was observed in the reactions containing, crude leaf extracts from soybean, *Medicago* and *Arabidopsis* (FIG. 6), indicating that all three plants have ADH activity in leaves.

As HPP produced multiple chromatographic peaks, as reported previously, HPP was reduced to 4-hydroxyphenyllactic acid (HPLA) by sodium borohydride ($NaBH_4$), resulting in a single quantifiable peak. HPLA production was observed in reactions containing soybean and *Medicago* leaf extracts but was absent in reactions with *Arabidopsis* and heat-inactivated extracts (FIG. 2A), indicating that soybean and *Medicago* have PDH activity in leaves. Although recombinant AtADH2 has very weak PDH activity besides strong ADH activity, no PDH activity was detected in the leaf tissue extract of *Arabidopsis* (FIG. 2A). Of all of the plants analyzed to date, soybean had the highest ratio of PDH/ADH activity in leaf tissue (FIG. 2C) as well as in other tissues examined (FIG. 2C).

Identification of PDH Enzymes in Legumes

A comparative genomics approach identified 12 candidates in the soybean genome that are homologous to previously reported TyrA proteins, *Arabidopsis* ADHs and bacterial PDH enzymes (*E. coli* CM-PDH NP_755003 and *Aquifex aeolicus* PDH NP_214202, E-value<1.2 $e^{-21}$). Three out of twelve sequences lacked conserved dehydrogenase domains, showed no detectable gene expression in publically available gene expression databases (http://www.soybase.org/ and Soybean eFP Browser; FIG. 7) and thus are likely to be pseudogenes. Of nine remaining candidates, only five showed substantial expression in all tissues examined in the databases (FIG. 7), which was further confirmed by RT-PCR. (FIG. 8). Phylogenetic analysis of the five soybean candidates showed that Glyma5g07870 and Glyma17g13150 fell within an eudicot chide containing previously characterized AtADHs, all having N-terminal chloroplast transit peptides (CTPs) (FIG. 3A and FIG. 9). Notably, the remaining three soybean candidates (Glyma11g35760, Glyma14g05990 and Glyma18g02650) formed a clade distinct from canonical plant ADHs (for example, *Arabidopsis* ADHs; FIG. 3A and FIG. 9), making them promising PDH candidates. Although the canonical ADH sequences were found in all plants, the sequences from the noncanonical clade were restricted to some plant lineages, including, the Leguminosae family (they are most likely lost in Brassicales, Cucurbitales and Rosales; FIG. 10).

To determine the enzymatic activities of the five candidates, their corresponding genes were amplified from cDNA prepared from soybean leaf tissue (where strong PDH activity was detected; FIG. 2) and cloned into a pET28a expression vector, and the recombinant enzymes were expressed in *E. coli*. The crude enzyme extracts were first subjected to PDH and ADH assays using saturating conditions to screen for any detectable PDH and/or ADH activity (FIG. 3B and FIG. 3C). ADH activity was detected from all five candidates. In contrast, PDH activity was detected only in Glyma11a35760 and Glyma18g02650 as well as their closest homolog from *Medicago* (Mt3g071980) but not in Glyma5g07870, Glyma17g13150 and Glyma14g05990 (FIG. 3C). These results suggest that Glyma5g07870 and Glyma17g13150, which are grouped within the canonical plant ADHs (for example, AtADHs; FIG. 3B; FIG. 9) and have a predicted CTP, are most likely involved in the plastidic ADH pathway commonly found in all plants. The lack of detectable PDH activity in Glyma14g05990 suggests that only a subclade of the noncanonical ADH and PDH clade contains PDH enzymes (Glyma11g35760, Glyma18g02650 and Mt3g071980; FIG. 3A).

Glyma18g02650 and Mt3g071980 are Bona Fide PDH Enzymes

To further characterize legume enzymes showing strong PDH activity, we purified the recombinant enzymes of Glyma18g02650 and Mt3g071980 using affinity chromatography. The purification of Glyma11g35760, a paralog of Glyma18g02650, was not successful owing to its low expression (FIG. 3B and FIG. 3C) and insolubility. As *E. coli* contains endogenous PDH activity catalyzed by the bifunctional CM-PDH enzyme, both PDH and CM activity were monitored during purification to ensure that the purified plant enzymes were not contaminated with *E. coli* CM-PDH. (FIG. 11). When substrate and cofactor specificity of the purified recombinant enzymes were tested, strong PDH activity was detected in Glyma18g02650 and Mt3g071980 with $NADP^+$ and to a lesser extent $NAD^+$ (FIG. 12). In contrast, much weaker ADH activity was detected with $NADP^+$ or $NAD^+$ for both Glyma18g02650 and Mt3g071980 (FIG. 12).

Kinetic analyses were performed using prephenate or L-arogenate as a substrate with the preferred cofactor, NADP+. The apparent $K_m$ values of Glyma18g02650 and Mt3g071980 for prephenate were 127 μM and 223 μM, respectively (Table 3), which are similar to those of other plant and microbial PDHs ranging from 77 μM (mung bean PDH activity) to 410 μM (*M. tuberculosis* PDH). The turnover rates ($k_{cat}$) of Glyma18g02650 and Mt3g071980 for PDH activity (26 $s^{-1}$ and 22 $s^{-1}$; respectively, Table 3) were also comparable to previously reported PDHs (13 $s^{-1}$ to 132 $s^{-1}$). Although both enzymes had ADH activity, their catalytic efficiency ($k_{cat}/K_m$) for ADH activity was >350-fold lower than those for PDH activity (Table 3). Furthermore, the apparent $K_m$ of Glyma18g02650 and Mt3g071980 for L-arogenate was 17 mM and 43 mM, respectively, far exceeding that of endogenous L-arogenate concentration in plants. Thus, their ADH activity detected in in vitro (FIG. 3B and FIG. 12) is not physiologically relevant. Taken together, these results suggest that Glyma18g02650 and Mt3g071980 are bona fide PDH enzymes, and thus we designate them as GmPDH1 and MtPDH1, respectively.

Legume PDH Activity and Enzymes are Non-Plastidic

Previously characterized enzymes involved in Tyr biosynthesis (for example, ADH and PPA-AT) and other aromatic amino acid pathways have been shown to localize in the plastids. Also, feeding studies showed that isolated plastids are capable of synthesizing Tyr, suggesting that plastids contain a complete Tyr biosynthetic pathway. Unexpectedly, however, unlike AtADHs having an N-terminal CTP, legume PDH enzymes clearly lack an N-terminal presequence before highly conserved catalytic domains. We confirmed the presence of an upstream stop codon (−48 bp) in frame with the ATG start codon on the GmPDH1 cDNA. To determine the localization of GmPDH1 and MtPDH1, we fused GFP to the C-terminal of GmPDH1 and MtPDH1 and expressed it in *Arabidopsis* protoplasts. The fluorescence signals of GFP fused with GmPDH1 and MtPDH1 did not overlap with chlorophyll fluorescence, similar to free GFP and unlike AtADH2-GFP (FIG. 4A-FIG. 4D), suggesting that GmPDH1 and MtPDH1 are not targeted to the plastids.

Subcellular fractionation further showed that soybean PDH activity was detected only in the cytosolic fraction, similar to the activity of a cytosolic marker enzyme, phosphoenolpyruvate (PEP) carboxylase (FIG. 4E and FIG. 4G). In contrast, ADH activity was enriched in the plastid fraction. Residual ADH activity was still detected in the cytosolic fraction but is most likely due to plastid contamination during tissue disruption, as was also observed for a plastid marker enzyme, PPA-AT (FIG. 4F and FIG. 4H). These data show that both legume PDH enzymes and PDH activity are localized outside of the plastids.

Soybean has Tyr- and Trp-Insensitive Cytosolic CM Activity

Cytosolic CMs have been identified in some plant species, which, if present in legumes, may provide the prephenate substrate for the cytosolic PDH enzymes. A phylogenetic analysis of plant CM orthologs identified two distinct clades: one with plastid-localized CMs having a CTP and another containing cytosolic CMs lacking a CTP. Soybean and *Medicago* sequences were found in both clades, suggesting that legumes also contain both plastidic and cytosolic CM isoforms. Consistently, CM activity was further detected in both the cytosolic and plastidic fractions of soybean leaf extracts (FIG. 4I). CM activity in the plastid fraction was completely inhibited by 1 mM L-Tyr and showed approximately threefold induction by 1 mM L-Trp, in agreement with previous reports from other plant species. In contrast, CM activity in the cytosol was only slightly decreased and increased by L-Tyr and L-Tip, respectively (FIG. 4I). Given that 25% of the plastid marker enzyme. PPA-AT, was contaminated in the cytosolic fraction (FIG. 4H), the Tyr- and Trp-sensitive portion (≥25%) of the cytosolic CM activity (FIG. 4I) is most likely due to plastidic contamination. Thus, the remaining Tyr- and Trp-insensitive CM activity detected in the cytosol is derived from an insensitive cytosolic CM isoform (or isoforms) present in soybean.

Legume PDH Activity and Enzymes are Insensitive to L-Tyr

ADHs and PDHs are almost always strongly inhibited by L-Tyr. To test whether L-Tyr also inhibits GmPDH1 and MtPDH1, we analyzed their activities in the absence and presence of different concentrations of L-Tyr. Consistent with a previous report, ADH activity of recombinant. AtADH2 enzyme was reduced by ~75% in the presence of 100 μM L-Tyr and abolished at ≥1 mM L-Tyr (FIG. 5A and Table 4). Under the same conditions, however, PDH activity of GmPDH1 and MtPDH1 were not inhibited by up to 10 mM of L-Tyr (FIG. 5A and Table 4), well beyond the physiological L-Tyr concentration in plants. PDH activity of soybean leaf extract as well as the *E. coli* extract expressing Glyma11g35760 were also not inhibited by L-Tyr (FIG. 5A and Table 4). Unlike mung bean PDH activity partially inhibited by L-Tyr at nonsaturating prephenate concentrations, the presence and absence of 1 mM L-Tyr did not affect GmPDH1 and MtPDH1 activity even at low prephenate concentrations (FIG. 13). HPP, the direct product of PDH reactions, as well as the other aromatic amino acids, L-Phe and L-Trp, did not reduce PDH activity of GmPDH1 or MtPDH1. These results demonstrate that legume PDHs are insensitive to L-Tyr as well as other pathway intermediates and products examined.

TABLE 4

L-Tyr insensitivity of legume PDH enzymes and activity presented in FIG. 5A

| | L-Tyr concentration (mM) | | | | |
|---|---|---|---|---|---|
| | 0 | 0.01 | 0.1 | 1.0 | 10 |
| AtADH2[a] | 923 ± 34 | 766 ± 35 | 251 ± 45 | N.D.[d] | N.D. |
| MtPDH1[b] | 579 ± 28 | 604 ± 22 | 610 ± 7 | 641 ± 19 | 652 ± 56 |
| GmPDH1[b] | 1059 ± 69 | 1064 ± 52 | 1103 ± 55 | 1065 ± 44 | 1152 ± 101 |
| Glyma11g35760[c] | 1219 ± 76 | 1211 ± 39 | 1173 ± 16 | 1250 ± 63 | 1109 ± 79 |
| Soybean leaf[c] | 47 ± 1.5 | 52 ± 4.0 | 50 ± 4.4 | 50 ± 0.7 | 51 ± 1.3 |

[a]ADH activity (uKat/mg)
[b]PDH activity (nKat/mg)
[c]PDH activity (pKat/mg)
[d]Not detectable Previous biochemical studies suggest that plants synthesize L-Tyr mainly via the plastid-localized ADH pathway (FIG. 4F). Consistent with this notion, we also found that soybean has plastid-localized ADH activity (FIG. 4F) and enzymes (for example, Glyma5g07870 and Glyma17g13150) that are closely related to AtADHs (FIG. 3A) and have ADH but not PDH activity (FIG. 3B and FIG. 3C). The plastid-synthesized Tyr is then exported to the cytosol for synthesis of proteins. Tyr-derived natural products and HPP via crosol-localized Tyr aminotransferase (TyrAT) (FIG. 5D). This study further identified legume PDH enzymes and PDH activity, both of which are localized in the cytosol (FIG. 4A-D and FIG. 4E-H) and not inhibited by L-Tyr (FIG. 5A). Previous studies have also identified in multiple plant species cytosolic CM isoforms that are insensitive to L-Tyr (unlike plastidic CMs that are inhibited by L-Tyr), though their function remains elusive. We also detected Tyr-insensitive cytosolic CM activity in soybean FIG. 4I). Thus, the identification a Tyr-insensitive PDH enzymes in legumes revealed the presence of a cytosolic, Tyr-insensitive PDH pathway that acts redundantly to the plastidic ADH pathway (FIG. 5D). Also, the cytosolic CM may provide the prephenate substrate for the cytosolic PDH pathway, at least in legumes (FIG. 5D). This cytosolic PDH pathway provides a direct route to HPP synthesis, bypassing three enzymatic steps from prephenate to HPP via the ADH pathway (catalyzed by PPA-AT, ADH and TyrAT, FIG. 5C). The cytosolic localization of the PDH pathway also escapes competition for prephenate in the plastids where Phe biosynthesis can consume up to 30% of photosynthate, mainly for lignin biosynthesis.

REFERENCES

1. Siehl, D. in *Plant Amin. Acids Biochem. Blotechnof.* (Singh. B.) 171-204 (CRC Press, 1999).
2. Gamborg, 0. L. Aromatic metabolism in plants II. Enzymes of the shikimate pathway in suspension cultures of plant cells. *Can. J. Biochem.* 44, 791-799 (1966).
3. Gamborg, 0. & Simpson, F. Preparation of prephenic acid and its conversion to phenylalanine and tyrosine by plant enzymes, *Can. J. Biochem.* 42, 583-591 (1964).
4. Gamborg, O. L. & Keeley, F. W. Aromatic metabolism in plants I. A study of the prephenate dehydrogenase from bean plants. *Biochim. Biophys. Acta* 115, 65-72 (1966).
5. Rubin, J. L. & Jensen, R. A. Enzymology of L-tyrosine biosynthesis in Mung bean (*Vigna radiata* [L.] Wilczek). *Plant Physiol.* 64, 727-714 (1979).
6. Connelly, J. A. & Conn, E. E. Tyrosine biosynthesis in *Sorghum bicolor*: isolation and regulatory properties of arogenate dehydrogenase. *Verlag der Zeitschriftfur Natwforsch.* 41c, 69-78 (1986).
7. Byng, G., Whitaker, R., Flick, C. & Jensen, R. A. Enzymology of L-tyrosine biosynthesis in corn (*Zea mays*). *Phytochemistry* 20, 1289-1292 (1981).
8. Gains C, G., Byng, G. S., Whitaker, R. J. & Jensen, R. A L-Tyrosine regulation and biosynthesis via arogenate dehydrogenase in suspension-cultured cells of *Nicotiana silvertris* Speg. et Comes. *Planta* 156, 233-240 (1982).

---

We claim:

1. A construct comprising a heterologous promoter operably linked to an isolated polynucleotide encoding a polypeptide having at least 98% identity to SEQ ID NO: 2 (Glyma18g02650PDH1), SEQ ID NO: 8 (Mtruncatula3g071980), or one of SEQ ID NO: 13-26, wherein the polypeptide is insensitive to feedback inhibition.

2. The polynucleotide of claim 1, wherein the polypeptide has prephenate dehydrogenase activity.

3. The polynucleotide of claim 1, wherein the polypeptide has arogenate dehydrogenase activity.

4. The polynucleotide of claim 1, wherein the polypeptide is insensitive to at least one of tyrosine, tryptophan, phenylalanine and 4-hydroxyphenylpyruvate.

5. The polynucleotide of claim 1, wherein the polynucleotide is a cDNA having at least 98% identity to SEQ ID NO: 1 or SEQ ID NO: 7.

6. The construct of claim 1, wherein the promoter is a plant promoter.

7. The construct of claim 1, wherein the promoter is a constitutive promoter or an inducible promoter.

8. A transgenic cell comprising the construct of claim 1 or a homolog or functional portion thereof or combinations thereof.

9. The transgenic cell of claim 8, wherein the cell is a plant cell.

10. The transgenic cell of claim 9, wherein the plant is selected from soybean, mung bean, alfalfa, rice, wheat, corn, barley, millet, oat, rye, rapeseed, and beet.

11. The transgenic cell of claim 8, wherein the cell is a bacterial or fungal cell.

12. A seed comprising the transgenic cell of claim 8.

13. A plant grown from the seed of claim 12.

14. A transgenic plant comprising the cell of claim 8.

15. The transgenic plant of claim 14, wherein the plant expresses the polypeptide at increased levels as compared to a corresponding non-transgenic plant.

16. The transgenic plant of claim 14, wherein the polypeptide is expressed in leaf tissue from the plant.

17. A part, progeny or asexual propagate of the transgenic plant of claim 14, wherein the part and progeny comprise the polynucleotide.

18. A method of increasing resistance of a plant to a herbicide comprising: increasing expression of, altering the expression pattern of or increasing the copy number of a polynucleotide or homologs, functional variants or combinations thereof in cells of the plant, wherein the polynucleotide encodes a polypeptide having at least 95% identity to SEQ ID NO: 2 (Glyma18g02650PDH1), SEQ ID NO: 4 (Glyma11g35760PDH2), SEQ ID NO: 6 (Glyma14g05990ADH1), SEQ ID NO: 8 (Mtruncatula3g071980), or one of SEQ ID NO: 13-26, and wherein increased expression of the polynucleotide in cells of the plant increases the resistance of the plant to the herbicide as compared to a control plant.

19. The method of claim 18, wherein the herbicide is a 4-hydroxyphenylpyruvate dioxygenase inhibitor.

20. The method of claim 19, wherein the inhibitor is sulcotrione, mesotrione, nitisnone, leptospermone, Mikado, fluorochloridone, and isoxaflutole.

21. The method of claim 18, wherein the plant is selected from soybean, alfalfa, mung bean, rice, wheat, corn, barley, millet, oat, rye, rapeseed, and beet.

22. A method of increasing production of at least one product of the tyrosine or HPP pathways in a plant comprising increasing expression of a polynucleotide or homologs, functional variants or combinations thereof in cells of the plant, wherein the polynucleotide encodes a polypeptide having at least 95% identity to SEQ ID NO: 2 (Glyma18g02650PDH1), SEQ ID NO: 4 (Glyma11g35760PDH2), SEQ ID NO: 6 (Glyma14g05990ADH1), SEQ ID NO: 8 (Mtruncatula3g071980), or one of SEQ ID NO: 13-26, and wherein increased expression of the polynucleotide in cells of the plant increases the production of the at least one product of the tyrosine or HPP pathways.

23. The method of claim 22, wherein the product is selected from vitamin E, plastoquinone, a cyanogenic glycoside, an isoquinoline alkaloid, rosmarinic acid, betalain, suberin, or tyrosine.

24. The method of claim 22, wherein the plant is selected from soybean, alfalfa, mung bean, rice, wheat, corn, barley, millet, oat, rye, rapeseed, and beet.

* * * * *